(12) United States Patent
Schally et al.

(10) Patent No.: US 9,079,974 B2
(45) Date of Patent: Jul. 14, 2015

(54) GH-RH ANALOGS WITH POTENT AGONISTIC EFFECTS

(75) Inventors: Andrew V Schally, Miami Beach, FL (US); Ren Zhi Cai, Miami, FL (US); Marta Zarandi, Szeged (HU)

(73) Assignees: The University of Miami, Miami, FL (US); The United States of America, represented by the Department of Veterans Affairs, Washington, DC (US)

( * ) Notice: Subject to any disclaimer, the term of this patent is extended or adjusted under 35 U.S.C. 154(b) by 281 days.

(21) Appl. No.: 13/332,624

(22) Filed: Dec. 21, 2011

(65) Prior Publication Data
US 2014/0058068 A1    Feb. 27, 2014

(51) Int. Cl.
| | |
|---|---|
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| A61K 38/24 | (2006.01) |
| A61K 38/27 | (2006.01) |
| C07K 1/00 | (2006.01) |
| C07K 14/61 | (2006.01) |
| C07K 14/60 | (2006.01) |

(52) U.S. Cl.
CPC ............. *C07K 14/61* (2013.01); *C07K 14/60* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,622,312 A | 11/1986 | Felix et al. | |
| 4,649,131 A | 3/1987 | Felix et al. | |
| 4,689,318 A | 8/1987 | Kaiser et al. | |
| 4,784,987 A | 11/1988 | Rivier et al. | |
| 4,914,189 A | 4/1990 | Schally et al. | |
| 5,262,519 A | 11/1993 | Rivier et al. | |
| 5,792,747 A * | 8/1998 | Schally et al. | ............... 514/11.2 |
| 5,846,936 A | 12/1998 | Felix et al. | |
| 6,458,764 B1 | 10/2002 | Gravel et al. | |
| 7,241,744 B2 | 7/2007 | Draghia-Akli et al. | |
| 7,268,113 B2 | 9/2007 | Bridon et al. | |
| 7,928,063 B2 | 4/2011 | Izdebski et al. | |
| 2005/0261201 A1 | 11/2005 | Polvino et al. | |
| 2007/0042950 A1 | 2/2007 | Schally et al. | |
| 2009/0023646 A1 | 1/2009 | Gaudreau | |
| 2010/0092539 A1 | 4/2010 | Schally et al. | |

FOREIGN PATENT DOCUMENTS

| | | |
|---|---|---|
| EP | 0413839 | 2/1991 |
| WO | WO 94/11396 | 5/1994 |
| WO | WO 94/11397 * | 5/1994 |
| WO | WO 2009/009727 A2 | 1/2009 |

OTHER PUBLICATIONS

Zarandi et al, Potent agonists of growth hormone-releasing hormone, Int. J. Pepride Protein Res. 39. 1992, 211-217.*
Armann et al., "Quantification of basal and stimulated ROS levels as predictors of islet potency and function,"*Am J Transplant*, (2007), 7:38-47.
Bajusz, et al. in *Peptides*, 1982, Blaha and Melon, Eds. de Gruyter, Berlin-N.Y., 1983, pp. 643-647.
Bonner-Weir, "In vitro cultivation of human islets from expanded ductal tissue," *Proc Natl Acad Sci USA*, (Jul. 5, 2000), 97(14):7999-8004.
Cai, et al., "Synthesis of new potent agonistic analogs of growth hormone-releasing hormone (GHRH) and evaluation of their endocrine and cardiac activities,"*Peptides* (Feb. 2014), 52:104-112. Epub: Dec. 25, 2013.
Campbell, et al., "GRF analogs and fragments: Correlation between receptor binding, activity and structure," *Peptides* (May/Jun. 1991), 12(3):569-574.
Corpas, et al., "Growth Hormone (GH)-Releasing Hormone-(1-29) Twice Daily Reverses the Decreased GH and Insulin-Like Growth Factor-I Levels in Old Men," *J. Clin. Endocrin. Metabol.* (1992), 75, 530-535.
Dor et al., "Adult pancreatic B-cells are formed by self-duplication rather than stem-cell differentiation," *Nature*, (May 6, 2004), 429:41-44.
Falutz, et al., "Effects of Tesamorelin, a Growth Hormone-Releasing Factor, in HIV_Infected Patients with Abdominal Fat Accumulation: A Randomized Placebo-Controlled Trial With a Safety Extension," *Acquir Immune Defic Syndr.* (2010), 53: 311-322.
Felix, et al., "Synthesis, biological activity and conformational analysis of cyclic GRF analogs," *Int. J. Peptide Protein Res.* (Dec. 1988), 32(6): 441-454.
Ferninandi, et al., "Non-Clinical Pharmacology and Safety Evaluation of TH9507, a Human Growth Hormone-Releasing Factor Analogue," *Basic & Clin Pharmacol Toxicol.* (2007), 100: 49-58.
Fiaschi-Taesch et al., "Hepatocyte Growth Factor Enhances Engraftment and Function of Nonhuman Primate Islets," *Diabetes*, (Oct. 2008), 57:2745-2754.
Frohman, et al., "Dipeptidylpeptidase IV and Trypsin-like Enzymatic Degradation of Human Growth Hormone-releasing Hormone in Plasma," *J. Clin. Invest.* (1989), 83, 1533-1540.

(Continued)

*Primary Examiner* — Marcela M Cordero Garcia
*Assistant Examiner* — Sergio Coffa
(74) *Attorney, Agent, or Firm* — Pepper Hamilton LLP

(57) ABSTRACT

There are provided a novel series of peptide analogs of hGH-RH(1-29)NH$_2$ and hGH-RH(1-30)NH$_2$ which show high activities in stimulating the release of pituitary GH in animals. They retain their physiological activity in solution for extended periods of time and resist enzymic degradation in the body. These novel and useful properties appear to be due to novel substitution patterns ant at the 1, 15, 27 and 29 positions on the peptide.

15 Claims, No Drawings

(56) References Cited

OTHER PUBLICATIONS

Granata et al., "Obestatin promotes survival of pancreatic beta-cells and human islets and induces expression of genes involved in the regulation of beta-cell mass and function," *Diabetes*, (Apr. 2008), 57:967-979.

Granata et al., "Growth hormone-releasing hormone promotes survival of cardiac myocytes in vitro and protects against ischaemia-reperfusion injury in rat heart," *Cardiovasc Res*, (2009), 83:303-312.

Guarcello et al., "Growth hormone releasing hormone receptors on thymocytes and splenocytes from rats," *Cell Immunol*, (1991), 136:291-902.

Havt et al., "The expression of the pituitary growth hormone-releasing hormone receptor and its splice variants in normal and neoplastic human tissues," *Proc Natl Acad Sci USA* (Nov. 29, 2005), 102(48):17424-17429.

Houssay, "[Role of the hypophysis in carbohydrate metabolism and diabetes]," *Folia Endoctrinol Mens Incretologia Incretoterapia*,(1950) 3(2):127-136.

Huising et al., "CRFR1 is expressed on pancreatic B cells, promotes B cell proliferation, and potentiates insulin secretion in a glucose-dependent manner," *Proc Natl Acad Sci USA*, (Jan. 12, 2010), 107(2): 912-917.

Izdebski, et al., "Synthesis and biological evaluation of superactive agonists of growth hormone-releasing hormone," *Proc Natl Acad Sci USA*, (May 1995), 92:4872-4876.

Jabs et al., "Reduced insulin secretion and content in VEGF-a deficient mouse pancreatic islets," *Exp Clin Endoctrinol Diabetes* (2008), 116 Suppl. 1:S45-49.

Kanashiro-Takeuchi et al., "Cardioprotective effects of growth hormone-releasing hormone agonist after myocardial infarction," *Proc Natl Adac Sci USA*, (Feb. 9, 2010), 107(6):2604-2609.

Khorram et al., "Effects of [Norleucine27] Growth Hormone-Releasing Hormone (GHRH) (1-29)-NH2 Administration on the Immune System of Aging Men and Women," *J Clin Endocrinol Metab*, (1997), 82(11):3590-3596.

Kirk, et al., "Treatment with GHRH(1-29)NH2 in children with idiopathic short stature induces a sustained increase in growth velocity," *Clinical Endocrinol.* (Oct. 1994) 41(4):487-493.

Kovacs, et al., "An evaluation of intravenous, subcutaneous, and in vitro activity of new agmatine analogs of growth-hormone releasing hormone hGH-RW (1-29)NH2," *Life Science*, (1988), 42(1): 27-35.

Lehmann et al., "Has time come for new goals in human islet transplantation?," *Am J Transplant*, (2008), 8:1096-1100.

Letsch et al., "Growth hormone-releasing hormone (GHRH) antagonists inhibit the proliferation of androgen-dependent and—independent prostate cancers," *Proc Natl Adac Sci USA*, (Feb. 4, 2003), 100(3):1250-1255.

Ling et al., "Isolation, primary structure, and synthesis of human hypothalamic somatocrini: growth hormone-releasing factor," *Proc Natl Acad Sci USA*, (1984), 81:4302-4306.

Merrifield, "Solid Phase Peptide Synthesis. I. The Synthesis of a Tetrapeptide," *J.Am.Chem.Soc.*, (1963), 85:2149.

Muranishi, et al., "Lipophilic Peptides: Synthesis of Lauroyl Thyrotropin-Releasing Hormone and Its Biological Activity," *Pharm. Res.* (May 1991), 8(5)649-652.

Nielsen et al., "Beta cell proliferation and growth factors," *J. Mol. Med.* (1999), 77:62-66.

Rekasi et al., "Isolation and sequencing of cDNAs for splice variants of growth hormone-releasing hormone receptors from human cancers," *Proc Natl Acad Sci USA*, (Sep. 12, 2000), 97(19):10561-10566.

Ross, et al., "Treatment of Growth-Hormone Deficiency with Growth-Hormone-Releasing Hormone," Lancet 1 (Jan. 3, 1987), 8523:5-8.

Schally et al., "Agonistic Analogs of Growth Hormone-Releasing Hormone: Endocrine and Growth Studies," Growth Hormone Secretagogues in *Clinical Practice* (1998), eds. Bercu and Walker, (Marcel Dekker, Inc. New York), 131-143.

Shapiro et al., "International trial of the Edmonton protocol for islet transplantation,"*N. Engl J Med*, (2006), 355:1318-1330.

Takano et al., "Human growth hormone-releasing hormone (hGH-RH; hGRF) treatment of four patients with GH deficiency," *Endocrinol. Japan* (1988) 35(5); 775-781.

Thorner, et al., "Acceleration of Growth in Two Children Treated with Human Growth Hormone-Releasing Factor," *N. Engl. J. Med.* (Jan. 3, 1985), 312(1):4-9.

Vance, "Growth-Hormone-Releasing Hormone," *Clin Chem*, (1990), 36:415-420.

Vance, "Growth hormone for the elderly?," *N. Eng. J. Med* (1990), 323(1):52-54.

Vasavada et al., "Growth factors and beta cell replication," *Int J. Biochem Cell Biol, Epub 31*, (Aug. 2005), 38(5-6):931-950.

Zarandi, et al., "Synthesis and in vitro and in vivo activity of analogs of growth hormone-releasing hormone (GH-RH) with C-terminal agmatine," *Int. J. Peptide Protein Res.* (Dec. 1990), 36(6):499-505.

Ziegler et al., "Dehydroepiandrosterone induces a neuroendocrine phenotype in nerve growth factor-stimulated chromaffin pheochromocytoma PC12 cells," *Endocrinology*, (2008), 149:320-328.

Ziegler et al., "Expression of neuropeptide hormone receptors in human adrenal tumors and cell lines: Antiproliferative effects of peptide analogues," *Proc Natl Acad Sci USA*, (Sep. 15, 2009), 106(37):15879-15884.

International Search Report for PCT/US2012/067690 dated Mar. 28, 2013.

* cited by examiner

GH-RH ANALOGS WITH POTENT AGONISTIC EFFECTS

This invention was made in part with Government support. The Government has certain rights in this application.

SEQUENCE LISTING

The instant application contains a Sequence Listing which has been submitted in ASCII format via EFS-Web and is hereby incorporated by reference in its entirety. Said ASCII copy, created on Dec. 13, 2011, is named SHAL3041.txt and is 35,007 bytes in size.

FIELD OF THE INVENTION

The present invention relates to growth hormone-releasing hormone (GH-RH) analogous peptides having high binding affinity to GH-RH receptor in vitro and having influence on the function of the pituitary gland in vivo. In particular, the present invention is directed to synthetic peptides which promote the release of growth hormone by the pituitary gland. More particularly, the present invention relates to hGH-RH analogs of 29 or 30 amino acids that show much higher affinity to the GH-RH receptor than the native hGH-RH(1-29)NH$_2$.

This invention also relates to a pharmaceutical composition comprising any one of said GH-RH agonists and to the use of these agonistic peptides in the treatment or prevention of disorders.

BACKGROUND OF THE INVENTION

In 1981 human pancreatic growth hormone releasing hormone (hGH-RH) was first isolated from extracts of human pancreatic tumors and subsequently from the hypothalamus of various mammals. This peptide was found to promote the release of growth hormone (GH) by the pituitary. The human hypothalamic GH-RH was found to have the same amino acid sequence as the pancreatic one. Human GH-RH (hGH-RH) contains 44 amino acids with an amidated carboxyl terminus. The structure of hGH-RH was reproduced by synthesis. Several analogs of hGH-RH have been synthesized and their biological activity studied. These studies revealed that:

a) a fragment of GH-RH containing at least 29 amino acid residues has at least 50% of the potency of natural GH-RH; further deletion of amino acid residues results in a marked decrease in bioactivity [Cambell R M et al. Peptides 12: 569-574 (1991)];

b) replacement of Arg in position 29 by Agm (agmatine, 4-guanidino-butylamine) is said to provide resistance to enzymatic degradation from C-terminus (Bajusz S et al. in Peptides, 1982, Blaha and Melon, Eds., Walter de Gruyter, Berlin-N.Y., 1983, pp. 643-647);

c) replacement of Tyr in position 1 by des-aminotyrosine (Dat) is said to lead to analogs with increased biological activities as a result of the resistance of N-terminus to enzymatic degradation [Felix A et al. Int. J. Peptide Protein Res. 32: 441-454 (1988), Kovacs M et al. Life Sci. 42: 27-35 (1988)]. U.S. Pat. Nos. 4,622,312, 4,649,131 and 4,784,987 disclose hGH-RH(1-29) agonists with Ala at position 15, as well as Dat at position 1. Several of these agonists are said to have potency four-fold that of hGH-RH(1-29);

d) several analogs containing Dat in position 1 and Agm in position 29 are said to exhibit enhanced GH releasing ability, and hence potency greater than that of hGH-RH(1-29) and in vivo [Zarandi M et al. Int. J. Peptide Protein Res. 36: 499-505 (1990), Zarandi M et al. Int. J. Peptide Protein Res. 39: 211-217 (1992)];

e) hydrophobic groups at the C-terminal of a peptides sequence can result in significantly increased specific activity. In terms of hydrophobicity, these results are contradicted by works of other groups, e.g. Muranichi [Muranichi S et al. Pharm. Res. 8: 649-652 (1991)];

Similarly, U.S. Pat. No. 4,914,189 discloses agonists having Dat at position 1, D-Ala at position 2, Lys or Orn at position 12, Gly at position 15, Lys at position 21 and Agm at position 29. It should be noted however that those agonists said to have had greater potency in inducing GH release than hGH-RH(1-29) had Lys at position 12 and D-Ala at position 2.

In U.S. Pat. No. 4,689,318 analogs of hGH-RH(1-29) may have Lys$^{12}$ or Lys$^{21}$ replaced by Orn and in which position 8 could be Ser (rat GH-RH sequence), Asn (human GH-RH sequence), Thr (mouse GH-RH sequence) or Gln (not naturally occurring in GH-RH); and position 27 could be Nle. In these analogs, position 1 is never Dat, position 15 never Abu, position 28 never Asp, and position 29 never Agm, Arg-NH—CH$_3$, or Arg-NH—CH$_2$—CH$_3$. Those analogs said to have potency as strong as hGH-RH(1-40) had substitutions by Arg at positions 12 and 21.

Other hGH-RH(1-29) agonists are taught in PCT patent applications numbers WO 94/11396 and 94/11397, where at position 12, Lys$^{12}$ is to be replaced by D-Lys, Arg or Orn. These analogs may also contain Dat as R$^1$; Asn, D-Asn, Ser, D-Ser as R$^8$; Abu as R$^{15}$; Lys, D-Lys, Arg or D-Arg as R$^{21}$; Nle as R$^{27}$; Asp or Ser as R$^{28}$; and Agm as R$^{29}$. Those agonists which are said to induce GH at levels exceeding those induced by hGH-RH(1-29) had Lys at positions 12. The teachings of these two publications however are considered open to question since, some time after the filing of these applications, it was discovered that the compounds believed to have been synthesized could not with certainty be said to correspond with the formulae they were originally paired with. Moreover, it was further discovered after filing these applications that the compounds could not release GH at the levels originally asserted.

European Patent Application 0 413 839 discloses further hGH-RH analogs in which positions 12 and 21 may both be Lys or Orn, and where position 15 is Ala. However, those analogs tested for GH releasing ability and said to have greater potency than hGH-RH(1-29) had Lys at positions 12 and 21.

U.S. Pat. No. 5,262,519 discloses agonists having the following substitutions: N-MeTyr at position 1, Ser at position 8, Ala at position 15, Ala or Aib at positions 16, 24, and 25, Asn at position 28, and —NHR at the C-terminus with R being H or lower alkyl. It should be noted however that these agonists said to have had greater potency in inducing GH release than hGH-RH(1-29) never had Gln or Thr at position 8, Orn at positions 12 and 21, Abu at position 15, and Asp at position 28.

U.S. Pat. No. 5,792,747 discloses GH-RH agonists having Dat at position 1; Glu at position 3; Ser, Gln, or Thr at position 8; Orn at positions 12 and 21; Ile at position 13; Ala or Abu at positions 15, 22, and 23; Glu at position 25; Nle, Ile, or Leu at position 27; Asn or Asp at position 28; and Agm at position 29. It should be noted however that those agonists said to have had greater potency in inducing GH release than hGH-RH(1-29) never had N-Me-Tyr$^1$, D-Ala$^2$, and/or —NH—CH$_3$ or —NH—CH$_2$—CH$_3$ at the C-terminus.

U.S. Pat. No. 7,928,063 discloses GH-RH agonists having the following substitutions: Dat at position 1; 6-guanidino-2- caproic acid (hArg), 4-guanidine-2-aminobutyric acid (Gab), or 3-guanidino-2-aminopropionic acid (Gap) at positions 11 and 20; Orn, hArg, Gab, or Gap at positions 12 and 21; Ala at position 15, Nle at position 27; and D-Arg, hArg, Gab, or Gap at position 29. These peptides are said to exhibit high resistance to enzymatic actions and are potent and selective GH release stimulators. It should be noted however that these agonists have been tested and showed high stability only in trypsin digestion test.

Up to now, most of the GH-RH analogs described have been tested in rat models, either in vitro or in vivo. Since human and rat GRF(1-29)NH$_2$ are markedly different, the structure-activity relationships of GH-RH are different in both species. Therefore, it is not possible to extrapolate results obtained in rats to humans. (Brazeau et al. U.S. Pat. No. 6,458,764).

Other hGH-RH(1-29) analogs are taught in US published application 2009/0023646 A1 and WO 2009/009727 A2, where the most potent compound has Ala$^2$, Tyr$^{10}$, Gly$^{15}$, and Leu$^{22}$ replaced by D-Ala$^2$, D-Tyr$^{10}$, D-Ala$^{15}$, and Lys$^{22}$, respectively, showed binding to GH-RH receptor on somatotrophs in rat and dog pituitaries and was at least two times more potent in vivo than the natural GH-RH(1-44).

An analog of hGH-RH(1-44)NH$_2$ (tesamorelin) that was modified by trans-3-hexenoyl group at the N-terminus showed resistance against DPP-IV catalyzed deactivation [Ferninandi E S et al. Basic Clin Pharmacol Toxicol. 100: 49-58 (2007) and Falutz J et al. Acquir Immune Defic Syndr 53: 311-322, (2010)]. It should be mentioned however that this agonist was not protected against endopeptidases and chemical degradation in aqueous solution and was only about twice as active as GH-RH itself.

Native hGH-RH(1-44) and its analogs are subject to biological inactivation by both enzymatic and chemical routes. In plasma, hGH-RH is rapidly degraded via dipeptidylpeptidase IV (DPP-IV) cleavage between residues 2 and 3 [Frohman et al., J. Clin. Invest. 83, 1533-1540 (1989), Kubiak et al. Drug Met. Disp. 17, 393-397 (1989)]. the major cleavage site in plasma. In pituitary and hypothalamus, the major cleavage sites are between Leu$^{14}$-Gly$^{15}$ (chymotrypsin-like enzymes) and between Lys$^{21}$-Leu$^{22}$ (trypsin-like enzymes) [Boulanger et al. Brain Res. 616, 39-47 (1993)]. Other trypsin specific cleavages at basic amino acid residues are also observed. The hGH-RH(1-44) is also subject to chemical rearrangement [forming Asp$^8$ or beta-Asp$^8$ from Asn$^8$ via aminosuccinimide formation] and oxidation [Met(O)$^{27}$ from Met$^{27}$] in aqueous environment that greatly reduce its bioactivity.

It is therefore advantageous to develop long-acting GH-RH analogues using specific amino acid replacements at the amino-terminus (to prevent enzymatic degradation), at residue 8 (to reduce isomerization), and residue 27 (to prevent oxidation). Inclusion of Ala15 or Abu15 substitutions for Gly 15, previously demonstrated to enhance receptor binding affinity, also improves GH-RH potency.

It would be desirable to produce hGH-RH analogs by multiple amino acid substitutions that have elevated binding affinities to the pituitary receptors in vitro, and increased potencies in vivo as compared to the native hGH-RH(1-29) NH$_2$.

Since one change in the amino acid sequence of a peptide could cause a big change in the three dimensional structure of the peptide which has influence on the binding property as well as the biological potency of the peptide, it is impossible to predict which one or more amino acid replacements or combinations of substitutions in hGH-RH analogs might result in improved binding affinity or high in vivo potency.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the peptide chain, particularly deletions beginning at the carboxyl terminus of the peptide and extending to about position-29, can be made in accordance with the known experimental practices to date to create peptides or peptide fragments that retain all or very substantial portions of the biological potency of the peptide, and such peptides are considered as being within the scope of the invention. Moreover, additions may be made to either terminus, or to both terminals, and/or generally equivalent residues can be substituted for naturally occurring residues, as is well-known in the overall art of peptide chemistry, to produce other analogs having at least a substantial portion of the potency of the claimed polypeptide without deviating from the scope of the invention. Moreover, modifications may be made to the preferred —NH$_2$ group at the C-terminus in accordance with the state of this art today; for example, the carboxyl moiety of the amino acid residue at the C-terminus can be the radical —COOR, —CRO, —CONHNHR, —CON(R)(R') or —CH$_2$—OR, with R and R' being lower alkyl, fluoro lower alkyl or hydrogen, without deviating from the invention, for such modifications result in equivalent synthetic peptides. (Rivier U.S. Pat. No. 5,262,519).

SUMMARY OF THE INVENTION

There is provided a novel series of synthetic peptide analogs of hGH-RH(1-29)NH$_2$ or hGH-RH(1-30)NH$_2$ The novel synthetic peptides of this invention exhibit high activities in stimulating the release of pituitary GH in animals, including humans. They also show extremely high binding capacity to the hGH-RH receptor. These synthetic hGH-RH analogs also retain their physiological activity in solution for an extended period of time and resist enzymatic degradation in the body. The stronger GH releasing potencies of the new analogs in vivo, as compared to previously described ones, results from combination of replacements in hGH-RH(1-29)NH$_2$ or hGH-RH(1-30)NH$_2$ and from resistance to in vivo degradation. Without in any way limiting the invention or its scope, applicants wish to express their understanding that the retention of activity in vitro and resistance to in vivo degradation are due to multiple substitutions in the molecule: incorporation of N-Me-Tyr or des-amino-Tyr (Dat) in position 1 which protect peptides from the degradation at the N-terminus; incorporation of agmatine (Agm) or —NH—CH$_3$ or —NH—CH$_2$—CH$_3$ at position 29 or extension of the C-terminus with an omega-amino acid which protects peptides from degradation at the C-terminus; and also the replacements of both lysines in the synthetic peptides with ornithine (Orn), which is a poor substrate for trypsin-like enzymes; Gly at residue 15 by Abu. To increase chemical stability, Asn at position 8 is replaced by Gln, Thr, or Ala. And Met in position 27 is replaced by norleucine (Nle). Replacement of other residues in the peptides and the combination of these replacements also are found to promote biological activity.

Synthetic Peptides

The synthetic hGH-RH analogs which may be expressed as

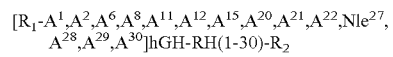

or alternatively as $$[R_1\text{-}A^1\text{-}A^2\text{-Asp-Ala-Ile } A^6 \text{ Thr-}A^8\text{-Ser-Tyr-}A^{11}\text{-}A^{12}\text{-} \\ \text{Val-Leu-}A^{15}\text{-Gln-Leu-Ser-Ala-}A^{20}, A^{21}\text{-} \\ A^{22}\text{-Leu-Gln-Asp-Ile-Nle-}A^{28}, A^{29}, A^{30}]\text{-}R_2$$ (SEQ ID NO: 1)

wherein
$R_1$ is Ac, Tfa, or is absent,
$A^1$ is Tyr, Dat, or N-Me-Tyr,
$A^2$ is Ala, D-Ala, Abu, or D-Abu,
$A^6$ is Phe or Fpa5,
$A^8$ is Asn, Ala, Gln, Thr, or N-Me-Ala,
$A^{11}$ is Arg, His, or Har,
$A^{12}$ is Orn, or Lys(Me)$_2$,
$A^{15}$ is Abu or Ala
$A^{20}$ is Arg, His, or Har,
$A^{21}$ is Orn, or Lys(Me)$_2$,
$A^{22}$ is Leu, or Orn,
$A^{28}$ is Ser, or Asp,
$A^{29}$ is Arg, Har, Agm, D-Arg, or D-Har,
$A^{30}$ is Arg, Agm, Ada, Amc, Aha, Apa, Har, D-Arg, D-Har, Gab, Gln, D-Gln, Gln-Gab, D-Gln-Gab, or is absent,
$R_2$ is —NH$_2$, —OH, —NHR$_3$, —N(R$_3$)$_2$, or —OR$_3$, in which $R_3$ is any of C$_{1-12}$ alkyl, C$_{2-12}$ alkenyl, or C$_{2-12}$ alkinyl, preferably provided that if $A^{29}$ is Agm then $A^{30}$ and $R_2$ are absent and suitably $A^1$ is N-Me-Tyr only, and further preferably provided that where $A^{30}$ is Agm then $R_2$ is absent, and pharmaceutically acceptable salts thereof.

DETAILED DESCRIPTION OF THE PREFERRED EMBODIMENTS

A. Synthetic Peptides

1. Nomenclature

The nomenclature used to define the amino acid residues and synthetic peptides is that specified by the IUPAC-IUB Commission on Biochemical Nomenclature (European J. Biochem., 1984, 138, 9-37). By natural amino acid is meant one of the common, naturally occurring amino acids found in proteins comprising Gly, Ala, Val, Leu, Ile, Ser, Thr, Lys, Arg, Asp, Asn, Glu, Gln, Cys, Met Phe, Tyr, Pro, Trp and His. By Nle is meant norleucine, by Abu is meant alpha amino butyric acid, and by Orn is meant ornithine. Other abbreviations used are:

Abbreviations

Aah alpha-amino-hexanoic acid
Aap alpha-amino-pentanoic acid
Abu alpha-aminobutyric acid
Ac acetyl
AcOH acetic acid
Ac$_2$O acetic anhydride
Ada 12-aminododecanoyl
Agm agmatine
Aha 6-aminohexanoyl
AM aminomethyl
Amc 8-Aminocaprylyl
Apa 5-Aminopentanoyl
Aib alpha-aminoisobutyroyl
Boc tert-butyloxycarbonyl
Bom benzyloxymethyl
2BrZ 2-bromo-benzyloxycarbonyl
Bu$^t$ tertiary butyl (ester)
Bzl benzyl
cHx cyclohexyl
2CIZ 2-chloro-benzyloxycarbonyl
2ClTrt 2-chlorotrityl
Cpa para-chlorophenylalanine
Dat des-amino-tyrosine
DCM dichloromethane
DIC N,N'-diisopropylcarbodiimide
DIEA diisopropylethylamine
DMF dimethylformamide
Et ethyl
Fm fluorenylmethyl
Fmoc fluorenylmethoxycarbonyl
For formyl
Fpa mono- or poly-fluorinated Phe (fluorine substitution on the aromatic ring)
Fpa5 pentafluoro-Phe
Gab gamma-amino butanoyl
GH growth hormone
GH-RH GH releasing hormone
Har homoarginine
HBTU 2-(1H-Benzotriazol-1-yl)-1,1,3,3-tetramethyluronium hexafluorophosphate
hGH-RH human GH-RH
HOBt 1-hydroxybenzotriazole
HPLC high performance liquid chromatography
Ibu isobutyryl
MBHA para-methylbenzhydrylamine
Me methyl
MeOH methanol
MeCN acetonitrile
Mmt 4-methoxytrityl
Mtr 4-methoxy-2,3,6-trimethylbenzenesulphonyl
N-Me-Ala N-methyl-Ala
N-Me-Tyr N-methyl-Tyr
Nle norleucine
NMM N-methylmorpholine
Oaa omega-amino acid
Orn ornithine
PAM phenylacetamidomethyl
Pbf 2,2,4,6,7-pentamethyl-dihydrobenzofurane-5-sulfonyl
Ph phenyl
PS polystyrene
rGH-RH rat GH-RH
RP-HPLC reversed phase HPLC
SPA para-sulfonyl-phenoxyacetyl
tBu tertiary butyl (ether)
TFA trifluoroacetic acid
Tfa trifluoroacetyl
Tos para-toluenesulfonyl
Trt trityl (triphenylmethyl)
Z benzyloxycarbonyl The amino acid sequences of the synthetic peptides are numbered in correspondence with the amino acid residues in hGH-RH(1-29); thus, for example, the Ala$^4$ and R$^8$ in the synthetic peptides occupy the same position in the sequence as the Ala$^4$ and R$^8$ residues in hGH-RH(1-29).

The convention under which the N-terminal of a peptide is placed to the left, and the C-terminal to the right is also followed herein.

2. Preferred Embodiments

The hGH-RH agonists of the present invention were designed to increase Gh release at the pituitary level. Particularly preferred embodiments of the synthetic peptides of the present invention are shown in Table 1:

P-20103 [N—Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGH-RH(1-29) (SEQ ID NO: 2)

P-20105 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$, Agm$^{29}$]hGH-RH(1-29)

P-20107 [N—Me-Tyr$^1$, Fpa5$^6$, Ala$^8$, Orn$^{12}$, Abu$^{15}$, Orn$^{21}$, Nle$^{27}$, Asp$^{28}$, Agm$^{29}$]hGH-RH(1-29) (SEQ ID NO: 3)

P-20109 [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Agm$^{29}$]hGH-RH(1-29)

P-20110 [N—Me-Tyr$^1$, D-Ala$^2$, Fpa5$^6$, Orn$^{12}$, Abu$^{15}$, Orn$^{21}$, Nle$^{27}$, Agm$^{29}$]hGH-RH(1-29)

P-20111 [N—Me-Tyr$^1$, D-Ala$^2$, Fpa5$^6$, Thr$^8$, Orn$^{12}$, Abu$^{15}$, Orn$^{21}$, Nle$^{27}$, Asp$^{28}$, Agm$^{29}$]hGH-RH(1-29)

P-20113 [N—Me-Tyr$^1$, Fpa5$^6$, Orn$^{12}$, Abu$^{15}$, Orn$^{21}$, Nle$^{27}$, Asp$^{28}$, Agm$^{29}$]hGH-RH(1-29) (SEQ ID NO: 4)

P-20115 [N—Me-Tyr$^1$, Fpa5$^6$, Thr$^8$, Orn$^{12}$, Abu$^{15}$, Orn$^{21}$, Nle$^{27}$, Asp$^{28}$, Agm$^{29}$]hGH-RH(1-29) (SEQ ID NO: 5)

P-20117 [N—Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGH-RH(1-29)

P-20350 [Dat$^1$, D-Ala$^2$, Gln$^8$, Orn$^{12}$, Abu$^{15}$, Orn$^{21}$, Nle$^{27}$, Asp$^{28}$, Agm$^{29}$]hGH-RH(1-29)

P-20351 [Ac—N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGH-RH(1-29)

P-20356 [N—Me-Tyr$^1$, Gln$^8$, Orn$^{12}$, Abu$^{15}$, Orn$^{21}$, Nle$^{27}$, Asp$^{28}$, Agm$^{29}$]hGH-RH(1-29) (SEQ ID NO: 6)

P-20357 [Dat$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGH-RH(1-29)

P-20358 [N—Me-Tyr$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGH-RH(1-29)

P-20359 [N—Me-Tyr$^1$, D-Ala$^2$, Fpa5$^6$, Orn$^{12}$, Abu$^{15}$, Orn$^{21}$, Nle$^{27}$, Asp$^{28}$, Agm$^{29}$]hGH-RH(1-29)

P-20360 [N—Me-Tyr$^1$, D-Ala$^2$, Thr$^8$, Orn$^{12}$, Abu$^{15}$, Orn$^{21}$, Nle$^{27}$, Asp$^{28}$, Agm$^{29}$]hGH-RH(1-29)

P-20361 [N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGH-RH(1-29)

P-20367 [N—Me-Tyr$^1$, D-Ala$^2$, Orn$^{12}$, Abu$^{15}$, Orn$^{21}$, Nle$^{27}$, Asp$^{28}$, Agm$^{29}$]hGH-RH(1-29)

P-20370 [N—Me-Tyr$^1$, Orn$^{12}$, Abu$^{15}$, Orn$^{21}$, Nle$^{27}$, Asp$^{28}$, Agm$^{29}$]hGH-RH(1-29) (SEQ ID NO: 7)

P-20371 [N—Me-Tyr$^1$, Thr$^8$, Orn$^{12}$, Abu$^{15}$, Orn$^{21}$, Nle$^{27}$, Asp$^{28}$, Agm$^{29}$]hGH-RH(1-29) (SEQ ID NO: 8)

P-20372 [N—Me-Tyr$^1$, Ala$^8$, Orn$^{12}$, Abu$^{15}$, Orn$^{21}$, Nle$^{27}$, Asp$^{28}$, Agm$^{29}$]hGH-RH(1-29) (SEQ ID NO: 9)

P-20373 [N—Me-Tyr$^1$, Gln$^8$, Orn$^{12}$, Abu$^{15}$, Orn$^{21}$, Nle$^{27}$, Agm$^{29}$]hGH-RH(1-29) (SEQ ID NO: 10)

P-20374 [N—Me-Tyr$^1$, Orn$^{12}$, Abu$^{15}$, Orn$^{21}$, Nle$^{27}$, Agm$^{29}$]hGH-RH(1-29) (SEQ ID NO: 11)

P-20375 [N—Me-Tyr$^1$, Thr$^8$, Orn$^{12}$, Abu$^{15}$, Orn$^{21}$, Nle$^{27}$, Agm$^{29}$]hGH-RH(1-29) (SEQ ID NO: 12)

P-20376 [N—Me-Tyr$^1$, Ala$^8$, Orn$^{12}$, Abu$^{15}$, Orn$^{21}$, Nle$^{27}$, Agm$^{29}$]hGH-RH(1-29) (SEQ ID NO: 13)

P-21300 [Dat$^1$, D-Ala$^2$, Orn$^{12}$, Abu$^{15}$, Orn$^{21}$, Nle$^{27}$, Asp$^{28}$, Amc$^{30}$]hGH-RH(1-30)NH$_2$

-continued

P-21301 [N—Me-Tyr$^1$, Orn$^{12}$, Abu$^{15}$, Orn$^{21}$, Nle$^{27}$, Asp$^{28}$, Amc$^{30}$]hGH-RH(1-30)NH$_2$ (SEQ ID NO: 14)

P-21303 [N—Me-Tyr$^1$, D-Ala$^2$, Orn$^{12}$, Abu$^{15}$, Orn$^{21}$, Nle$^{27}$, Asp$^{28}$, Amc$^{30}$]hGH-RH(1-30)NH$_2$

P-21304 [Dat$^1$, D-Ala$^2$, Gln$^8$, Orn$^{12}$, Abu$^{15}$, Orn$^{21}$, Nle$^{27}$, Asp$^{28}$, Amc$^{30}$]hGH-RH(1-30)NH$_2$

P-21305 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGH-RH(1-30)NH$_2$

P-21306 [Dat$^1$, D-Ala$^2$, Thr$^8$, Orn$^{12}$, Abu$^{15}$, Orn$^{21}$, Nle$^{27}$, Asp$^{28}$, Amc$^{30}$]hGH-RH(1-30)NH$_2$

P-21307 [N—Me-Tyr$^1$, D-Ala$^2$, Thr$^8$, Orn$^{12}$, Abu$^{15}$, Orn$^{21}$, Nle$^{27}$, Asp$^{28}$, Amc$^{30}$]hGH-RH(1-30)NH$_2$

P-21308 [Dat$^1$, D-Ala$^2$, Ala$^8$, Orn$^{12}$, Abu$^{15}$, Orn$^{21}$, Nle$^{27}$, Asp$^{28}$, Amc$^{30}$]hGH-RH(1-30)NH$_2$

P-21309 [N—Me-Tyr$^1$, D-Ala$^2$, Orn$^{12}$, Ala$^8$, Abu$^{15}$, Orn$^{21}$, Nle$^{27}$, Asp$^{28}$, Amc$^{30}$]hGH-RH(1-30)NH$_2$

P-21310 [Dat$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGH-RH(1-30)NH$_2$

P-21311 [N—Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGH-RH(1-30)NH$_2$

P-22325 [N—Me-Tyr$^1$, Gln$^8$, Orn$^{12}$, Abu$^{15}$, Orn$^{21}$, Nle$^{27}$, Asp$^{28}$, Apa$^{30}$]hGH-RH(1-30)NH$_2$ (SEQ ID NO: 15)

P-22326 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGH-RH(1-30)NH$_2$

P-22327 [Dat$^1$, Gln$^8$, Orn$^{12}$, Abu$^{15}$, Orn$^{21}$, Nle$^{27}$, Asp$^{28}$, Apa$^{30}$]hGH-RH(1-30)NH$_2$ (SEQ ID NO: 16)

P-22328 [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGH-RH(1-30)NH$_2$

P-22329 [N—Me-Tyr$^1$, D-Ala$^2$, Orn$^{12}$, Abu$^{15}$, Orn$^{21}$, Nle$^{27}$, Apa$^{30}$]hGH-RH(1-30)NH$_2$

P-22330 [N—Me-Tyr$^1$, D-Ala$^2$, Thr$^8$, Orn$^{12}$, Abu$^{15}$, Orn$^{21}$, Nle$^{27}$, Asp$^{28}$, Apa$^{30}$]hGH-RH(1-30)NH$_2$

P-22331 [N—Me-Tyr$^1$, D-Ala$^2$, Ala$^8$, Orn$^{12}$, Abu$^{15}$, Orn$^{21}$, Nle$^{27}$, Asp$^{28}$, Apa$^{30}$]hGH-RH(1-30)NH$_2$

P-22332 [N—Me-Tyr$^1$, Orn$^{12}$, Abu$^{15}$, Orn$^{21}$, Nle$^{27}$, Asp$^{28}$, Apa$^{30}$]hGH-RH(1-30)NH$_2$ (SEQ ID NO: 17)

P-22334 [N—Me-Tyr$^1$, Orn$^{12}$, Abu$^{15}$, Orn$^{21}$, Nle$^{27}$, Apa$^{30}$]hGH-RH(1-30)NH$_2$ (SEQ ID NO: 18)

P-22335 [N—Me-Tyr$^1$, Thr$^8$, Orn$^{12}$, Abu$^{15}$, Orn$^{21}$, Nle$^{27}$, Asp$^{28}$, Apa$^{30}$]hGH-RH(1-30)NH$_2$ (SEQ ID NO: 19)

P-22336 [N—Me-Tyr$^1$Ala$^8$, Orn$^{12}$, Abu$^{15}$, Orn$^{21}$, Nle$^{27}$, Asp$^{28}$, Apa$^{30}$]hGH-RH(1-30)NH$_2$ (SEQ ID NO: 20)

P-22337 [N—Me-Tyr$^1$, D-Ala$^2$, Cpa$^6$, Gln$^8$, Orn$^{12}$, Abu$^{15}$, Orn$^{21}$, Nle$^{27}$, Asp$^{28}$, Apa$^{30}$]hGH-RH(1-30)NH$_2$

P-23250 [Dat$^1$, D-Ala$^2$, Gln$^8$, Orn$^{12}$, Abu$^{15}$, Orn$^{21}$, Nle$^{27}$, Asp$^{28}$, Har$^{30}$]hGH-RH(1-30)NH$_2$

P-23251 [Dat$^1$, Gln$^8$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 21)

P-23252 [Dat$^1$, D-Ala$^2$, Orn$^{12}$, Abu$^{15}$, Orn$^{21}$, Nle$^{27}$, Asp$^{28}$, Har$^{30}$]hGH-RH(1-30)NH$_2$

P-23253 [Dat$^1$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 22)

P-23254 [Dat$^1$, D-Ala$^2$, Thr$^8$, Orn$^{12}$, Abu$^{15}$, Orn$^{21}$, Nle$^{27}$, Asp$^{28}$, Har$^{30}$]hGH-RH(1-30)NH$_2$

P-23255 [Dat$^1$, Thr$^8$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 23)

-continued

P-23256 [Dat$^1$, D-Ala$^2$, Ala$^8$, Orn$^{12}$, Abu$^{15}$, Orn$^{21}$, Nle$^{27}$, Asp$^{28}$, Har$^{30}$]hGH-RH(1-30)NH$_2$

P-23257 [Dat$^1$, Ala$^8$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 24)

P-23258 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGH-RH(1-30)NH$_2$

P-23259 [N—Me-Tyr$^1$, Gln$^8$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 25)

P-23260 [N—Me-Tyr$^1$, D-Ala$^2$, Orn$^{12}$, Abu$^{15}$, Orn$^{21}$, Nle$^{27}$, Asp$^{28}$, Har$^{30}$]hGH-RH(1-30)NH$_2$

P-23261 [N—Me-Tyr$^1$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 26)

P-23262 [N—Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGH-RH(1-30)NH$_2$

P-23263 [N—Me-Tyr$^1$, Thr$^8$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 27)

P-23264 [N—Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGH-RH(1-30)NH$_2$

P-23265 [N—Me-Tyr$^1$, Ala$^8$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 28)

P-24340 [N—Me-Tyr$^1$, Gln$^8$, Orn$^{12}$, Abu$^{15}$, Orn$^{21}$, Nle$^{27}$, Asp$^{28}$, Aha$^{30}$]hGH-RH(1-30)NH$_2$ (SEQ ID NO: 29)

P-24341 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGH-RH(1-30)NH$_2$

P-24342 [Dat$^1$, Gln$^8$, Orn$^{12}$, Abu$^{15}$, Orn$^{21}$, Nle$^{27}$, Asp$^{28}$, Aha$^{30}$]hGH-RH(1-30)NH$_2$ (SEQ ID NO: 30)

P-24344 [Dat$^1$, D-Ala$^2$, Gln$^8$, Orn$^{12}$, Abu$^{15}$, Orn$^{21}$, Nle$^{27}$, Asp$^{28}$, Aha$^{30}$]hGH-RH(1-30)NH$_2$

P-24345 [N—Me-Tyr$^1$, D-Ala$^2$, Orn$^{12}$, Abu$^{15}$, Orn$^{21}$, Nle$^{27}$, Asp$^{28}$, Aha$^{30}$]hGH-RH(1-30)NH$_2$

P-24346 [N—Me-Tyr$^1$, D-Ala$^2$, Gln$^8$, Orn$^{12}$, Abu$^{15}$, Orn$^{21}$, Nle$^{27}$, Aha$^{30}$]hGH-RH(1-30)NH$_2$

P-24347 [N—Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGH-RH(1-30)NH$_2$

P-24348 [N—Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGH-RH(1-30)NH$_2$

P-25501 [N—Me-Tyr$^1$, D-Ala$^2$, Orn$^{12}$, Abu$^{15}$, Orn$^{21}$, Nle$^{27}$, Gab$^{30}$]hGH-RH(1-30)NH$_2$

P-25502 [Dat$^1$, D-Ala$^2$, Fpa5$^6$, Orn$^{12}$, Abu$^{15}$, Orn$^{21}$, Nle$^{27}$, Gab$^{30}$]hGH-RH(1-30)NH$_2$

P-25503 [N—Me-Tyr$^1$, Abu$^2$, Orn$^{12}$, Abu$^{15}$, Orn$^{21}$, Nle$^{27}$, Gab$^{30}$]hGH-RH(1-30)NH$_2$ (SEQ ID NO: 31)

P-25504 [Dat$^1$, D-Abu$^2$, Orn$^{12}$, Abu$^{15}$, Orn$^{21}$, Nle$^{27}$, Gab$^{30}$]hGH-RH(1-30)NH$_2$

P-25506 [N—Me-Tyr$^1$, D-Abu$^2$, Orn$^{12}$, Abu$^{15}$, Orn$^{21}$, Nle$^{27}$, Gab$^{30}$]hGH-RH(1-30)NH$_2$

P-25508 [Tfa-Tyr$^1$, D-Ala$^2$, Orn$^{12}$, Abu$^{15}$, Orn$^{21}$, Nle$^{27}$, Gab$^{30}$]hGH-RH(1-30)NH$_2$

P-25516 [N—Me-Tyr$^1$, D-Ala$^2$, Orn$^{12}$, Abu$^{15}$, Orn$^{21}$, Nle$^{27}$, Asp$^{28}$, Gab$^{30}$]hGH-RH(1-30)NH$_2$

P-26802 [Dat$^1$, D-Ala$^2$, Thr$^8$, His$^{11}$, Orn$^{12}$, Abu$^{15}$, His$^{20}$, Orn$^{21}$, Nle$^{27}$, Ada$^{30}$]hGH-RH(1-30)NH$_2$

P-26803 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGH-RH(1-30)NH—CH$_3$

P-26804 [N—Me-Tyr$^1$, D-Ala$^2$, Gln$^8$, Orn$^{12}$, Abu$^{15}$, Orn$^{21}$, Nle$^{27}$, Ada$^{30}$]hGH-RH(1-30)NH$_2$

-continued

P-27400 [Dat$^1$, D-Ala$^2$, Orn$^{12}$, Abu$^{15}$, Orn$^{21}$, Nle$^{27}$, Asp$^{28}$]hGH-RH(1-29)NH—CH$_3$

P-27401 [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGH-RH(1-29)NH—CH$_3$

P-27403 [N—Me-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_3$

P-27404 [N—Me-Tyr$^1$, D-Ala$^2$, Fpa5$^6$, Orn$^{12}$, Abu$^{15}$, Orn$^{21}$, Nle$^{27}$, Asp$^{28}$]hGH-RH(1-29)NH—CH$_3$

P-27405 [N—Me-Tyr$^1$, Gln$^8$, Orn$^{12}$, Abu$^{15}$, Orn$^{21}$, Nle$^{27}$]hGH-RH(1-29)NH—CH$_3$ (SEQ ID NO: 32)

P-27406 [N—Me-Tyr$^1$, Gln$^8$, Orn$^{12}$, Abu$^{15}$, Orn$^{21}$, Nle$^{27}$, Asp$^{28}$]hGH-RH(1-29)NH—CH$_3$ (SEQ ID NO: 33)

P-27407 [Dat$^1$, Gln$^8$, Orn$^{12}$, Abu$^{15}$, Orn$^{21}$, Nle$^{27}$, Asp$^{28}$]hGH-RH(1-29)NH—CH$_3$ (SEQ ID NO: 34)

P-27408 [Dat$^1$, D-Ala$^2$, Gln$^8$, Orn$^{12}$, Abu$^{15}$, Orn$^{21}$, Nle$^{27}$, Asp$^{28}$]hGH-RH(1-30)NH—CH$_3$

P-27409 [N—Me-Tyr$^1$, D-Ala$^2$, Orn$^{12}$, Abu$^{15}$, Orn$^{21}$, Nle$^{27}$, Asp$^{28}$]hGH-RH(1-29)NH—CH$_3$

P-27410 [N—Me-Tyr$^1$, D-Ala$^2$, Thr$^8$, Orn$^{12}$, Abu$^{15}$, Orn$^{21}$, Nle$^{27}$, Asp$^{28}$]hGH-RH(1-29)NH—CH$_3$

P-27411 [N—Me-Tyr$^1$, D-Ala$^2$, Thr$^8$, Orn$^{12}$, Abu$^{15}$, Orn$^{21}$, Nle$^{27}$]hGH-RH(1-29)NH—CH$_3$

P-27412 [N—Me-Tyr$^1$, D-Ala$^2$, Ala$^8$, Orn$^{12}$, Abu$^{15}$, Orn$^{21}$, Nle$^{27}$, Asp$^{28}$]hGH-RH(1-29)NH—CH$_3$

P-27413 [Dat$^1$, Gln$^8$, His$^{11}$, Orn$^{12}$, Abu$^{15}$, His$^{20}$, Orn$^{21}$, Nle$^{27}$, Asp$^{28}$]hGH-RH(1-29)NH—CH$_3$ (SEQ ID NO: 35)

P-27414 [N—Me-Tyr$^1$, D-Ala$^2$, Fpa5$^6$, Orn$^{12}$, Abu$^{15}$, Orn$^{21}$, Nle$^{27}$, Gab$^{30}$]hGH-RH(1-30)NH—CH$_3$

P-27415 [N—Me-Tyr$^1$, Orn$^{12}$, Abu$^{15}$, Orn$^{21}$, Nle$^{27}$, Gab$^{30}$]hGH-RH(1-30)NH—CH$_3$ (SEQ ID NO: 36)

P-27416 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGH-RH(1-29)NH—CH$_3$

P-27417 [Ac-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_3$

P-27418 [Ac-Tyr$^1$, D-Ala$^2$, Fpa5$^6$, Orn$^{12}$, Abu$^{15}$, Orn$^{21}$, Nle$^{27}$, Asp$^{28}$]hGH-RH(1-29)NH—CH$_3$

P-27419 [Ac-Tyr$^1$, Thr$^8$, Orn$^{12}$, Abu$^{15}$, Orn$^{21}$, Nle$^{27}$]hGH-RH(1-29)NH—CH$_3$ (SEQ ID NO: 37)

P-27422 [N—Me-D-Tyr$^1$, Gln$^8$, Orn$^{12}$, Abu$^{15}$, Orn$^{21}$, Nle$^{27}$, Asp$^{28}$]hGH-RH(1-29)NH—CH$_3$

P-27423 [N—Me-D-Tyr$^1$, D-Ala$^2$, Orn$^{12}$, Abu$^{15}$, Orn$^{21}$, Nle$^{27}$, Asp$^{28}$]hGH-RH(1-29)NH—CH$_3$

P-27424 [Dat$^1$, Thr$^8$, Orn$^{12}$, Abu$^{15}$, Orn$^{21}$, Nle$^{27}$]hGH-RH(1-29)NH—CH$_3$ (SEQ ID NO: 38)

P-27425 [N—Me-D-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_3$

P-27440 [Dat$^1$, Gln$^8$, Orn$^{12}$, Abu$^{15}$, Orn$^{21}$, Nle$^{27}$, Asp$^{28}$, D-Arg$^{29}$]hGH-RH(1-29)NH—CH$_3$

P-27441 [N—Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGH-RH(1-29)NH—CH$_3$

P-27442 [N—Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGH-RH(1-29)NH—CH$_3$

P-27443 [N—Me-Tyr$^1$, Orn$^{12}$, Abu$^{15}$, Orn$^{21}$, Nle$^{27}$, D-Arg$^{29}$]hGH-RH(1-29)NH—CH$_3$

P-27444 [N—Me-Tyr$^1$, D-Ala$^2$, Orn$^{12}$, Abu$^{15}$, Orn$^{21}$, Nle$^{27}$, Asp$^{28}$, D-Arg$^{29}$]hGH-RH(1-29)NH—CH$_3$

P-27445 [N—Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGH-RH(1-29)NH—CH$_3$

-continued

P-27446 [N-Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGH-RH(1-29)NH—CH$_3$

P-27447 [N-Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGH-RH(1-30)NH—CH$_3$

P-27448 [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGH-RH(1-30)NH—CH$_3$

P-27449 [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGH-RH(1-30)NH—CH$_3$

P-27450 [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGH-RH(1-30)NH—CH$_3$

P-27451 [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGH-RH(1-30)NH—CH$_3$

P-28420 [N-Me-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_2$—CH$_3$

P-28421 [N-Me-Tyr$^1$, D-Ala$^2$, Orn$^{12}$, Abu$^{15}$, Orn$^{21}$, Nle$^{27}$, Asp$^{28}$]hGH-RH(1-29)NH—CH$_2$—CH$_3$

P-28430 [N-Me-Tyr$^1$, D-Ala$^2$, Gln$^8$, Orn$^{12}$, Abu$^{15}$, Orn$^{21}$, Nle$^{27}$]hGH-RH(1-29)NH—CH$_2$—CH$_3$

P-28431 [N-Me-Tyr$^1$, D-Ala$^2$, Thr$^8$, Orn$^{12}$, Abu$^{15}$, Orn$^{21}$, Nle$^{27}$, Asp$^{28}$]hGH-RH(1-29)NH—CH$_2$—CH$_3$

P-28460 [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGH-RH(1-29)NH—CH$_2$—CH$_3$

P-28461 [N-Me-Tyr$^1$, D-Ala$^2$, Gln$^8$, Orn$^{12}$, Abu$^{15}$, Orn$^{21}$, Nle$^{27}$]hGH-RH(1-29)NH—CH$_2$—CH$_3$

P-28462 [N-Me-Tyr$^1$, D-Ala$^2$, Fpa5$^6$, Orn$^{12}$, Abu$^{15}$, Orn$^{21}$, Nle$^{27}$]hGH-RH(1-29)NH—CH$_2$—CH$_3$

P-28463 [N-Me-Tyr$^1$, D-Ala$^2$, Orn$^{12}$, Abu$^{15}$, Orn$^{21}$, Nle$^{27}$]hGH-RH(1-29)NH—CH$_2$—CH$_3$

P-28464 [N-Me-Tyr$^1$, D-Ala$^2$, Fpa5$^6$, Gln$^8$, Orn$^{12}$, Abu$^{15}$, Orn$^{21}$, Nle$^{27}$]hGH-RH(1-29)NH—CH$_2$—CH$_3$

P-28465 [N-Me-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_2$—CH$_3$

P-28466 [N-Me-Tyr$^1$, D-Ala$^2$, Fpa5$^6$, Orn$^{12}$, Abu$^{15}$, Orn$^{21}$, Nle$^{27}$, Asp$^{28}$]hGH-RH(1-29)NH—CH$_2$—CH$_3$

P-28467 [N-Me-Tyr$^1$, D-Ala$^2$, Orn$^{12}$, Abu$^{15}$, Orn$^{21}$, Nle$^{27}$, Asp$^{28}$]hGH-RH(1-29)NH—CH$_2$—CH$_3$

P-28468 [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGH-RH(1-29)NH—CH$_2$—CH$_3$

P-28469 [Dat$^1$, D-Ala$^2$, Gln$^8$, Orn$^{12}$, Abu$^{15}$, Orn$^{21}$, Nle$^{27}$]hGH-RH(1-29)NH—CH$_2$—CH$_3$

P-28470 [Dat$^1$, D-Ala$^2$, Orn$^{12}$, Abu$^{15}$, Orn$^{21}$, Nle$^{27}$]hGH-RH(1-29)NH—CH$_2$—CH$_3$

P-28471 [Dat$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_2$—CH$_3$

P-28472 [Dat$^1$, D-Ala$^2$, Fpa5$^6$, Gln$^8$, Orn$^{12}$, Abu$^{15}$, Orn$^{21}$, Nle$^{27}$, Asp$^{28}$]hGH-RH(1-29)NH—CH$_2$—CH$_3$

P-28473 [Dat$^1$, D-Ala$^2$, Fpa5$^6$, Orn$^{12}$, Abu$^{15}$, Orn$^{21}$, Nle$^{27}$, Asp$^{28}$]hGH-RH(1-29)NH—CH$_2$—CH$_3$

P-28474 [Dat$^1$, D-Ala$^2$, Orn$^{12}$, Abu$^{15}$, Orn$^{21}$, Nle$^{27}$, Asp$^{28}$]hGH-RH(1-29)NH—CH$_2$—CH$_3$

P-28475 [N-Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGH-RH(1-30)NH—CH$_2$—CH$_3$

P-28476 [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGH-RH(1-30)NH—CH$_2$—CH$_3$

P-28477 [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGH-RH(1-30)NH—CH$_2$—CH$_3$

P-28478 [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGH-RH(1-30)NH—CH$_2$—CH$_3$

P-28479 [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGH-RH(1-30)NH—CH$_2$—CH$_3$

P-29701 [N-Me-Tyr$^1$, D-Ala$^2$, Gln$^8$, Orn$^{12}$, Abu$^{15}$, Orn$^{21}$, Nle$^{27}$, Asp$^{28}$, Gln-Gab$^{30}$]hGH-RH](1-30)NH$_2$

-continued

P-29702 [Dat$^1$, D-Ala$^2$, Orn$^{12}$, Abu$^{15}$, Orn$^{21}$, Nle$^{27}$, Gln-Gab$^{30}$]hGH-RH(1-30)NH$_2$

P-29703 [N—Me-Tyr$^1$, Gln$^8$, Orn$^{12}$, Abu$^{15}$, Orn$^{21}$, Nle$^{27}$, Gln-Gab$^{30}$]hGH-RH(1-30)NH$_2$ (SEQ ID NO: 39).

P-29704 [Dat$^1$, D-Ala$^2$, Gln$^8$, Orn$^{12}$, Abu$^{15}$, Orn$^{21,22}$, Nle$^{27}$, Gln-Gab$^{30}$]hGH-RH(1-30)NH$_2$

P-29706 [Tfa-Tyr$^1$, D-Abu$^2$, Gln$^8$, Orn$^{12}$, Abu$^{15}$, Orn$^{21}$, Nle$^{27}$, Gln-Gab$^{30}$]hGH-RH(1-30)NH$_2$

P-29708 [N—Me-Tyr$^1$, D-Ala$^2$, Fpa5$^6$, Orn$^{12}$, Abu$^{15}$, Orn$^{21}$, Nle$^{27}$, Gln-Gab$^{30}$]hGH-RH(1-30)NH$_2$

P-29710 [N—Me-Tyr$^1$, D-Ala$^2$, Fpa5$^6$, Ala$^8$, Orn$^{12}$, Abu$^{15}$, Orn$^{21}$, Nle$^{27}$, Gln-Gab$^{30}$]hGH-RH(1-30)NH$_2$

P-29720 [Dat$^1$, D-Ala$^2$, Orn$^{12}$, Abu$^{15}$, Orn$^{21}$, Nle$^{27}$, Asp$^{28}$, Gln-Gab$^{30}$]hGH-RH(1-30)NH$_2$

P-29721 [Dat$^1$, D-Ala$^2$, Gln$^8$, Orn$^{12}$, Abu$^{15}$, Orn$^{21,22}$, Nle$^{27}$, Asp$^{28}$, Gln-Gab$^{30}$]hGH-RH(1-30)NH$_2$

P-29722 [Tfa-Tyr$^1$, D-Abu$^2$, Gln$^8$, Orn$^{12}$, Abu$^{15}$, Orn$^{21}$, Nle$^{27}$, Asp$^{28}$, Gln-Gab$^{30}$]hGH-RH(1-30)NH$_2$

P-29723 [N—Me-Tyr$^1$, D-Ala$^2$, Fpa5$^6$, Orn$^{12}$, Abu$^{15}$, Orn$^{21}$, Nle$^{27}$, Asp$^{28}$, Gln-Gab$^{30}$]hGH-RH(1-30)NH$_2$

P-29724 [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Gln-Gab$^{30}$] hGH-RH(1-30)NH$_2$

B. Method of Preparation

1. Overview of Synthesis

The peptides are synthesized by suitable methods such as by exclusive solid phase techniques, by partial solid-phase techniques, by fragment condensation or by classical solution phase synthesis. For example, the techniques of exclusive solid-phase synthesis are set forth in the textbook "Solid Phase Peptide Synthesis", J. M. Stewart and J. D. Young, Pierce Chem. Company, Rockford, Ill., 1984 (2nd. ed.), and M. Bodanszky, "Principles of Peptide Synthesis", Springer Verlag, 1984. The hGH-RH agonist peptides are preferably prepared using solid phase synthesis, such as that generally described by Merrifield, J. Am. Chem. Soc, 85 p. 2149 (1963), although other equivalent chemical syntheses known in the art can also be used as previously mentioned.

The synthesis is carried out with amino acids that are protected at their alpha amino group. Urethane type protecting groups (Boc or Fmoc) are preferably used for the protection of the alpha amino group. In certain cases, protected omega-amino acids are also used during the synthesis. Boc or Fmoc protecting groups are also appropriate for the protection of omega-amino groups.

In solid phase synthesis, the N-alpha-protected or N-omega-protected amino acid moiety which forms the aminoacyl group of the final peptide at the C-terminus is attached to a polymeric resin support via a chemical link. After completion of the coupling reaction, the alpha (or omega) amino protecting group is selectively removed to allow subsequent coupling reactions to take place at the amino-terminus, preferably with 50% TFA in DCM when the N-alpha-(N-omega-) protecting group is Boc, or by 20% piperidine in DMF when the N-alpha-(N-omega-) protecting group is Fmoc. The remaining amino acids with similarly Boc or Fmoc-protected alpha (or omega) amino groups are coupled stepwise to the free amino group of the preceding amino acid on the resin to obtain the desired peptide sequence. Because the amino acid residues are coupled to the alpha (or omega) amino group of the C-terminus residue, growth of the synthetic hGH-RH analogue peptides begins at the C terminus and progresses toward the N-terminus. When the desired sequence has been obtained, the peptide is acylated, or the amino group is left free at the N-terminus, and the peptide is removed from the support polymer.

Each protected amino acid is used in excess (2.5 or 3 equivalents) and the coupling reactions are usually carried out in DCM, DMF or mixtures thereof. The extent of completion of the coupling reaction is monitored at each stage by the ninhydrin reaction. In cases where incomplete coupling is determined, the coupling procedure is repeated, or a capping by acetylation of unreacted amino groups is carried out, before removal of the alpha (or omega) amino protecting group prior to the coupling of the next amino acid.

Typical synthesis cycles are shown in Table 2 and Table 3.

TABLE 2

Protocol for a Typical Synthetic Cycle Using Boc-strategy

| Step | Reagent | Mixing Time (min) |
|---|---|---|
| 1. Deprotection | 50% TFA in DCM | 5 + 25 |
| | DCM wash | 1 |
| | 2-propanol wash | 1 |
| 2. Neutralization | 5% DIEA in DCM | 1 |
| | DCM wash | 1 |
| | MeOH wash | 1 |
| | 5% DIEA in DCM | 3 |
| | MeOH wash | 1 |
| | DCM wash (3 times) | 1 |
| 3. Coupling | 3 eq. Boc-amino acid in DCM or DMF + 3 eq. DIC or the preformed HOBt ester of the Boc-amino acid | 60 |
| | MeOH wash (3 times) | 1 |
| | DCM wash (3 times) | 1 |
| 4. Acetylation (if appropriate) | Ac$_2$O in pyridine (30%) | 10 + 20 |
| | MeOH wash (3 times) | 1 |
| | DCM wash (3 times) | 1 |

TABLE 3

Protocol for a Typical Synthetic Cycle Using Fmoc-strategy

| Step | Reagent | Mixing Time (min) |
|---|---|---|
| 1. Deprotection | 20% piperidine in DMF | 5 + 15 |
|  | DMF wash (3 times) | 1 |
| 2. Coupling | 3 eq. Fmoc-amino acid in DMF + 3 eq. DIC or + 3 eq. HBTU + 3 eq. HOBt + 6 eq. DIEA DMF wash (3 times) | 60 1 |
| 3. Acetylation (if appropriate) | 3 eq. 1-acetylimidazole in DMF DMF wash (3 times) | 30 1 |

After completion of the synthesis, the cleavage of the peptide from the resin can be effected using procedures well known in peptide chemistry.

2. Choice of the Support Polymer

The hGH-RH agonist peptides may be synthesized on a variety of support polymers, i.e. MBHA, Merrifield, PAM, Rink amide or Wang resins. The peptides can also be synthesized on aminomethyl, MBHA, or other resins that have been previously derivatized with suitable linkers. Examples of such linkers are the base-labile 4-hydroxymethyl benzoic acid (HMBA) linker for the attachment of C-terminal carboxyl groups, the acid-labile para-sulfonyl-phenoxyacetyl (SPA) linker which permits the attachment of agmatine through its guanidino group, or the acid-labile [3-[(Methyl-Fmoc-amino)methyl]-indol-1-yl]-acetyl linker which allows the synthesis of peptides with C-terminal methylamide (—NH—CH$_3$).

When peptides with an amidated C-terminus are synthesized by using Boc strategy, the preferred resin is MBHA. Attachment of the C-terminal amino acid to this resin can be accomplished by the standard DIC-mediated coupling method described in Table 2.

In order to prepare peptides with C-terminal methylamide (—NH—CH$_3$) or ethylamide (—NH—CH$_2$—CH$_3$) modification, two methods can be used: a) the Merrifield resin is loaded with the Boc-protected C-terminal amino acid by coupling mediated by potassium fluoride (KF) or cesium salt at elevated temperature; a) [3-[(Methyl-Fmoc-amino)methyl]-indol-1-yl]-acetylAm or b) 3-[(Ethyl-Fmoc-amino)methyl]-indol-1-yl]-acetyl Am resins are used, respectively for the synthesis of peptides having C-terminal methylamide (—NH—CH$_3$) or ethylamide (—NH—CH$_2$—CH$_3$) modification. Using these resins, the Fmoc protecting group has to be removed from the resin with the method described in Table 3 before the synthesis.

For the synthesis of peptides having Agm at the C-terminus, two methods have been used. In one case, the support phase is MBHA resin or an aminomethyl resin, and the guanidino group of Boc-Agm is joined to the support polymer through a stable, but readily cleavable linker such as the para-sulfonyl-phenoxyacetyl (SPA) moiety. The alpha-amino-Boc-protected Agm is reacted with the chlorosulfonyl phenoxyacetic acid Cl—SO$_2$—C$_6$H$_4$—O—CH$_2$—COOH to form Boc-Agm-SO$_2$—C$_6$H$_4$—O—CH$_2$—COOH. This compound is then coupled to the support polymer e.g. to MBHA resin using DIC or HBTU-HOBt-DIEA as activating reagent to yield Boc-Agm-SPA-MBHA. In another case, Agm-SO$_2$-PS resin is used for the synthesis (1% DVB, 100-200 mesh, 2.5 mmol/g, Advanced ChemTech (Louisville, Ky.)) at pH 10-13 to from Boc-Agm-SO$_2$-resin

3. Amino Acid Derivatives Used

Bifunctional amino acids, i.e. those not having side chain functional groups, are mostly used in the form of their N-alpha Boc- or Fmoc-derivatives for synthesis. Bifunctional omega-amino acids are also typically used in the form of their N-omega Boc- or Fmoc-derivatives. Thus, Boc-Gly-OH or Fmoc-Gly-OH is typically used for incorporating the Gly residue. The naturally occurring bifunctional amino acids are Gly, Ala, Val, Leu, Ile, Phe, and Pro, and some well-known non-coded bifunctional amino acids used in this invention are Abu, Aib, Gab, Nle, Aah, and Aap.

Some of the amino acid residues of the peptides have side chain functional groups which are reactive with reagents used in coupling or deprotection. When such side chain groups are present, suitable protecting groups are joined to these functional groups to prevent undesirable chemical reactions occurring during the coupling reactions.

The following general rules are followed in selecting a particular side chain protecting group: (a) the protecting group preferably retains its protecting properties and is not split off under coupling conditions, (b) the protecting group should be stable under conditions for removing the alpha amino protecting group at each step of the synthesis, (c) the side chain protecting group must be removable upon the completion of the synthesis of the desired amino acid sequence, under reaction conditions that will not undesirably alter the peptide chain.

When Boc-amino acids are used in the synthesis, the reactive side chain functional groups can be protected as follows: Tos or nitro (NO$_2$) for Arg and Har; cHx or Fm for Asp and Glu; Bom for His; 2ClZ or Fmoc for Lys and Orn; Bzl for Ser and Thr; and 2BrZ for Tyr. The side chains of Asn and Gln are unprotected.

In the case of Fmoc synthesis, the reactive side chain functional groups can be protected by other appropriate protective groups as follows: 2,2,4,6,7-pentamethyl-dihydrobenzofurane-5-sulfonyl (Pbf), 4-methoxy-2,3,6-trimethylbenzene-sulphonyl (Mtr), or bis-Boc for Arg and Har; tert-butyl (Bu$^t$) for Asp and Glu; no protective group or trityl (Trt) protection for Asn and Gln; Trt for His; Boc or 4-methoxytrityl (Mmt) for Lys and Orn; tBu or Trt for Ser and Thr; and tBu or 2-chlorotrityl (2ClTrt) for Tyr. In addition to the widely known coded and non-coded amino acids mentioned above, some of the peptides of this application contain less common non-coded amino acids such as homoarginine (Har); ornithine (Orn); lM-methyl-alanine [N-Me-Ala]; N-methyl-tyrosine [N-Me-Tyr]; pentafluoro-phenylalanine [Phe(F)$_5$, Fpa5]. These amino acid residues are incorporated into the peptides by coupling the suitable protected amino acid derivatives. A non-exclusive list of such protected amino acid derivatives that can be used is as follows: Boc-Har(Tos)-OH, Boc-Orn(2ClZ)-OH, Boc-N-Me-Ala-OH, Boc-N-Me-Tyr (2BrZ)-OH, Boc-Fpa5-OH, Fmoc-Har(Pbf)-OH, Fmoc-Orn (Boc)-OH, Fmoc-N-Me-Ala-OH, and Fmoc-N-Me-Tyr (2ClTrt)-OH. The protected derivatives of noncoded amino acids mentioned above are commonly available from several commercial suppliers, including Novabiochem (San Diego, Calif.), Advanced ChemTech (Louisville, Ky.), Bachem (King of Prussia, Pa.), Peptides International (Louisville, Ky.), RSP Amino Acid Analogues DBA (Worcester, Mass.), and AnaSpec (San Jose, Calif.).

4. Stepwise Coupling of Amino Acid Residues

Utilizing the above mentioned support polymers and after loading of the protected C-terminal amino acid or Agm residue, the peptide itself may suitably be built up by solid phase synthesis in the conventional manner. Each protected amino acid is coupled in about a three-fold molar excess, with respect to resin-bound free amino residues, and the coupling may be carried out in a medium such as DMF-DCM (1:1) or in DMF or DCM alone. The selection of an appropriate coupling reagent is within the skill of the art. Particularly suitable as coupling reagents are N,N'-diisopropyl carbodiimide (DIC), or HBTU combined with HOBt in the presence of DIEA. The success of the coupling reaction at each stage of the synthesis is preferably monitored by the ninhydrin reaction. In cases where incomplete coupling occurs, either the coupling procedure is repeated, or the resin-bound unreacted amino residues are acetylated using a capping reagent, before removal of the alpha (or omega) amino protecting group. Suitable capping reagents are 1-acetylimidazole and $Ac_2O$ in pyridine

5. Cleavage of the Peptide from the Support Polymer and Removal of the Side-Chain Protecting Groups When the synthesis is complete, the peptide is cleaved from the support phase and its side-chain protecting groups are removed.

In cases where peptides with an amidated C-terminus ($—CONH_2$) or with a C-terminal carboxyl group (—COOH) are prepared by Boc strategy on an MBHA, Merrifield, or PAM resin, the removal of the peptide from the resin is performed by treatment with a reagent such as liquid hydrogen fluoride (HF). This is also the case for peptides synthesized on the Boc-Agm-SPA-MBHA or Bos-Agm-tosyl-resin. In some instances, the liquid HF also cleaves all the remaining side chain protecting groups. However, if side chain protecting groups resistant to HF treatment are present on the peptide, additional cleavage steps should be performed in order to remove these protecting groups. Thus, Fm and Fmoc protecting groups are removed by treatment with 20% piperidine in DMF, prior to or after the HF treatment.

Suitably, the dried and protected peptide-resin is treated with a mixture consisting of 1.0 mL m-cresol and 10 mL anhydrous hydrogen fluoride per gram of peptide-resin for 60-120 min at 0° C. to cleave the peptide from the resin as well as to remove the HF-labile side chain protecting groups. After the removal of the hydrogen fluoride under a stream of nitrogen and vacuum, the free peptides are precipitated with ether, filtered, washed with ether and ethyl acetate, extracted with 50% acetic acid, and lyophilized.

In cases where peptides with a methyl-($—NH—CH_3$), or ethyl-amide ($—NH—CH_2—CH_3$) C-terminus are prepared by Boc strategy on the Merrifield or HMBA-MBHA resin, the protected peptides are first cleaved from the resin by methylamine ($CH_3NH_2$) or ethylamine ($CH_3CH_2NH_2$) mediated aminolysis. Suitably, liquid $CH_3NH_2$ or $CH_3CH_2NH_2$ is transferred into a cooled, heavy-walled glass flask that contains the dried and protected peptide-resin. The quantity of liquid $CH_3NH_2$ or $CH_3CH_2NH_2$ should be sufficient to cover the peptide-resin. The flask is stoppered, and shaken with the liquid $CH_3NH_2$ or $CH_3CH_2NH_2$ for 3.5 hours at room temperature in order to allow for the reaction to take place. After this, the flask is cooled in a dry ice bath, opened, and the liquid $CH_3NH_2$ or $CH_3CH_2NH_2$ is filtered off the solid residue that contains a mixture of resin and cleaved peptide, the peptide still having the protecting groups attached.

The solid residue is dried and subjected to HF treatment as described above, in order to remove the side chain protecting groups of the peptide.

In cases when peptides with a methyl-($—NH—CH_3$), or ethyl-amide ($—NH—CH_2—CH_3$) C-terminus are prepared by Fmoc strategy on [3-[(Methyl-Fmoc-amino)methyl]-indol-1-yl]-acetyl AM or 3-[(Ethyl-Fmoc-amino)methyl]-indol-1-yl]-acetyl AM resins, respectively, the protected peptides are cleaved from the resin with a cleavage cocktail. Since no single cleavage and deprotection procedure is optimal for all peptides due to the nature of the linker and the amino acid composition of the peptide, the following cleavage cocktail proved to be the most suitable for cleavage and deprotection of GHRH agonists: 94% TFA, 3% $H_2O$, 1.5% m-cresol, and 1.5% phenol. Cleavage cocktail must be prepared fresh and have to use high quality TFA and scavengers. The amount of cleavage cocktail used depends on both the amount of the peptide-resin and its properties. Enough cocktail solution should be used to saturate and swell the resin during the reaction, with about 2-3 mm of clear solution below the floating beads. Generally 5 mL of cleavage cocktail is used for 0.5 g of resin. The choice of reaction time depends on the linker and the side-chain protecting groups of the peptide. Preferably, 3-hour reaction time is used for the cleavage and deprotection of GHRH agonists. To induce peptide precipitation, the cleavage mixture is added dropwise to cold (preferably −20° C.) ether. The non-peptide products remain in the ether solution. The precipitated material is collected by filtration or centrifugation and is washed three times with cold ether to remove any residual scavengers. The cleaved and deprotected peptide is dissolved in 50% acetic acid and separated from the resin by filtration and, after dilution with water, the solution is lyophilized.

6. Purification

The purification of the crude peptides can be effected using procedures well known in peptide chemistry. For example, purification may be performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0 using an XBridge Prep OBD™ reversed phase column (4.6×250 mm, packed with $C_{18}$ silica gel, 300 Å pore size, 5 µm particle size) (Waters Co., Milford, Mass.). The column is eluted with a solvent system consisting of (A) 0.1% aqueous TFA and (B) 0.1% TFA in 70% aqueous MeCN in a linear gradient mode (e.g., 30-55% B in 120 min); flow rate of 12 mL/min. The eluent is monitored at 220 nm, and fractions are examined by analytical HPLC using a Hewlett-Packard Model HP-1090 liquid chromatograph and pooled to give maximum purity. Analytical HPLC is carried out on a Supeico Discovery HS C18 reversed-phase column (2.1×50 mm, C18, 300 Å pore size, 3 µm particle size) (Supeico, Bellefonte, Pa.) using isocratic elution with a solvent system consisting of (A) and (B) defined above with a flow rate of 0.2 mL/min. The peaks are monitored at 220 and 280 nm. The peptides are judged to be substantially (>95%) pure by analytical HPLC. Molecular masses are checked by electrospray mass spectrometry (Agilent Technologies 6210 Time-of-Light LC/MS, Santa Clara, Calif.) and the expected amino acid compositions are confirmed by amino acid analysis

C. Pharmaceutical Compositions and Mode of Administration

The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, trifluoroacetate, citrate, benzoate, succinate, alginate, pamoate, malate, ascorbate, tartarate, and the like. Particularly preferred agonists are salts of low solubility, e.g., pamoate salts and the like. These exhibit long duration of activity.

The compounds of the present invention are suitably administered to subject humans or animals subcutaneously (s.c), intramuscularly (i.m.), or intravenously (i.v); intranasally or by pulmonary inhalation; by transdermal delivery; or in a depot form (e.g., microcapsules, microgranules, or cylindrical rod like implants) formulated from a biodegradable suitable polymer (such as D,L-lactide-coglycolide), the former two depot modes being preferred. Other equivalent modes of administration are also within the scope of this invention, i.e., continuous drip, cutaneous patches, depot injections, infusion pump and time release modes such as microcapsules and the like. Administration is in any physiologically acceptable injectable carrier, physiological saline being acceptable, though other carriers known to the art may also be used.

The peptides are preferably administered parenterally, intramuscularly, subcutaneously or intravenously with a pharmaceutically acceptable carrier such as isotonic saline. Alternatively, the peptides may be administered as an intranasal spray with an appropriate carrier or by pulmonary inhalation. One suitable route of administration is a depot form formulated from a biodegradable suitable polymer, e.g., poly-D,L-lactide-coglycolide as microcapsules, microgranules or cylindrical implants containing dispersed antagonistic compounds.

The amount of peptide needed depends on the type of pharmaceutical composition and on the mode of administration. In cases where human subjects receive solutions of GH-RH agonists, administered by i.m. or s.c. injection, or in the form of intranasal spray or pulmonary inhalation, the typical doses are between 2-20 mg/day/patient, given once a day or divided into 2-4 administrations/day. When the GH-RH agonists are administered intravenously to human patients, typical doses are in the range of 8-80 µg/kg of body weight/day, divided into 1-4 bolus injections/day or given as a continuous infusion. When depot preparations of the GH-RH agonists are used, e.g. by i.m. injection of pamoate salts or other salts of low solubility, or by i.m. or s.c. administration of microcapsules, microgranules, or implants containing the antagonistic compounds dispersed in a biodegradable polymer, the typical doses are between 1-10 mg agonist/day/patient

D. Medical Applications of hGH-RH Agonists

The products of the present invention may be utilized to promote the growth of warm-blooded animals (e.g., humans) and also enhance the milk production of females of milk producing mammals, suitably but not exclusively goats and cows, preferably cows.

The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, citrate, benzoate, succinate, alginate, pamoate, malate, ascorbate, tartarate, and the like.

The compounds of the present invention are suitably administered to the subject humans or animals s.c, i.m., or i.v; intranasally or by pulmonary inhalation; or in a depot form (e.g., microcapsules, microgranules, or cylindrical rod like implants) formulated from a biodegradable suitable polymer (such as D,L-lactide-co-glycolide), the former two depot modes being preferred. Other equivalent modes of administration are also within the scope of this invention, i.e., continuous drip, depot injections, infusion pump and time release modes such as microcapsules and the like. Administration is in any physiologically acceptable injectable carrier, physiological saline being acceptable, though other carriers known to the art may also be used.

The dosage level is suitably between 0.01 µg and 2 µg/kg body weight per injection, except for depot form where the amount injected would be calculated to last from about 15 to about 30 days or longer. These dosage ranges are merely preferred. Administration of non-depot forms may be between 1 and 4 times per day, or in the case of lactating mammals, after each milking.

Until the production of growth hormone by recombinant-DNA methods began, the small supply of pituitary-derived human growth hormone limited its use to the treatment of children with growth hormone deficiency. The wide availability of synthetic human growth hormone has made possible long-term studies of other potentially beneficial uses of growth hormone and its more physiologic actions. Although synthetic GH is currently approved in the USA only for treatment of growth failure due to lack of endogenous growth hormone, this therapy has also been used to treat short children not classically GH deficient. However the cost of long-term treatment with hGH and the need of daily s.c. administration are important considerations. Currently, the cost of growth hormone therapy for a child with growth deficiency ranges from $10,000 to 30,000 a year depending on body weight. Treatment of a 70-kg adult with hGH three times a week costs $13,800 a year. Vance, M. L, N. Eng. J. Med 323:52-54 (1990). Thus, long-term growth hormone treatment in elderly adults with diminished growth hormone secretion would require a considerable personal and financial investment. In addition there are many children all over the world with growth retardation due to the lack of GH who cannot be treated with hGH because of the cost of this therapy. Consequently there is an urgent need to develop a drug that releases GH and with an affordable price. This alternative method to increase endogenous growth hormone secretion is through the administration of agonistic analogs of growth hormone-releasing hormone. The therapy with GH-RH agonistic analogs should be much less expensive than that utilizing hGH. In addition, the development of long-acting delivery systems for these analogs can make this new modality of treatment more practical and convenient.

The ability to produce synthetic growth hormone by recombinant DNA technology has enabled the manufacture of GH in potentially unlimited quantities. This greatly facilitated the treatment of GH-deficient children. As stated above, synthetic hGH is currently approved only for the treatment of growth failure due to a lack of adequate endogenous growth hormone, but hGH has also been used to treat short children who are not classically GH-deficient such as girls with Turner's syndrome; prepubertal children with chronic renal insufficiency and severe growth retardation; and children with non-GH deficient short stature.

The production of GH by genetic engineering is very expensive for clinical use. In particular, there are risks of contamination of these commercial preparations with material from the bacterial strain used. These bacterial contaminants may be pyrogens or may result in immunogenic reactions in patients. The purification of the recombinant product is carried out by following a plurality of successive chromatography steps. The drastic purity criteria imposed by regulatory agencies necessitate multiple quality control steps. U.S. Pat. No. 6,458,764.

Of the 3 million children born in the USA annually, 90,000 will be below the third percentile for height. These children may be labeled as having short stature and may be candidates for GH treatment. Therapy with human growth hormone currently costs about $20,000 per year and the average length of treatment is about 10 years. The treatment will usually be stopped when the patient reaches an acceptable adult size (a height of well over five feet) or when the patient matures sexually and the epiphyses close, at which time linear growth eases, or if the patient fails to respond to the treatment. If all children who are less than the third percentile for height receive a five year course of hGH therapy, hGH for height augmentation therapy will cost at least $8 billion to 10 billion per year. Lantos J. et al., JAMA 261:1020-1024, (1989).

It is desirable to ascertain the endogenous physiological ability of children having short stature to produce hGH. This may be done with a diagnostic test using a 50-100 μg dose of GH-RH; a 50-100 μg dose of a GH-RH analog which is a synthetic peptide of Formula I; and assaying the GH response evoked by each dose.

The assay means may be any conventional means which will indicate the quantitative amount of hGH present in a blood sample drawn from the patient. The concentration of GH in serum is determined using standard radioimmunoassay ("RIA") procedures as set forth in e.g., Miles I. E. M. et al., Lancet ii, 492-493 (1968) or O'Dell W et al., J. Lab. Clin. Med. 70, 973-80 (1967).

The test is used as follows. First, the GH-RH dose is administered. Thirty minutes later, a blood sample is taken for RIA of GH. Various commercially available kits (e.g., Nichols Institute of Diagnostics, San Juan Capistrano, Calif.) or reference preparations of hGH (e.g., NIAMDD-hGH-RP-1) can be used for RIA of GH. After waiting 6-24 hours for the effect of GH-RH to wear off, the dose of the synthetic peptide GH-RH analog is administered. Blood again is drawn for radioimmunoassay of GH.

The presence of a normal hGH response in the first assay reveals that endogenous hGH producing ability is present. This result also suggests a short, mild course of GH-RH therapy, if any, may be suitable. A low GH response, or no response, to the first dose reveals only that GH-RH must be evaluated in view of the second test result. If a good hGH response follows the second dose, there is clear physiological hGH producing ability which is not evoked by GH-RH. This indicates that a therapy with the GH-RH analog may be desirable. Finally, no or low response to both tests reliably reveals lack of physiological ability to produce hGH, and so suggests therapy with hGH is probably needed.

As indicated above, short stature in children may result from many causes, none of which are immediately apparent. Use of the diagnostic test on all children with this condition would greatly clarify the cause of short stature. Such a widespread screening test would also provide earlier indications for desirable treatment.

Glucocorticoids are potent inhibitors of linear growth in man and growth suppression is a well known risk of long term treatment of asthmatic children with steroids. Thus stunted growth is an important consequence of chronic administration of glucocorticoids in childhood. The inhibition of GH secretion is due in some extent to the fact that chronic administration of glucocorticoids suppresses GHRH. This inhibition occurs at the level of the hypothalamus or above and in this situation only the treatment with GH-RH agonists will stimulate linear growth.

Growth hormone tends to decline with the aging process and may lead to decrease in muscle mass and adiposity. Studies have shown that healthy older men and women with growth hormone deficiency had increases in lean body mass and decreases in the mass of adipose tissue after six months of hGH administration. Other effects of long-term administration of hGH on body composition included increase in vertebral-bone density and increase in skin-fold thickness. In addition, it has been reported that daily GH-RH injection to menopausal women, for 8 days augments GH responses and IGF-I levels and raises serum osteocalcin levels. Thus the therapy with GH-RH agonistic analogs reduces the loss of muscle, bone and skin mass and lessen the increase of body fat that normally accompanies the aging process.

Growth hormone is a potent anabolic hormone that enhances protein synthesis and nitrogen retention. Chronic administration of agonistic analogs of GH-RH increases the endogenous growth hormone secretion. The therapy with GH-RH agonistic analogs has uses in other areas of medicine such as catabolic states causing accelerated weight loss; tissue repair in patients with severe body surface burn, accelerating healing of nonunion fractures; and in some cases of cardiac failure.

Although long term follow-up is necessary before all treatment responses can be ascribed to GH, there has been improvement in cardiac mass and an increase in both cardiac mass and contractility. The therapy with hGH interrupts the cardiac-cachexia cycle. This response is in keeping with other observations that the therapy with GH has a major role in catabolic states in adults. An alternative method to increase endogenous growth hormone secretion in these conditions is the administration of GH-RH agonistic analogs [Korpas et al., J. Clin. Endoc. Metabol. 75, 530-535, (1992)].

These agonistic analogs of GH-RH can replace hGH for many applications. GH-deficient children respond to GH-RH (1-40), GH-RH(1-29) or GH-RH(1-44), with an increase in growth. Thorner M. O. et al., supra; Ross et al., supra; Takano K et al., supra; and Kirk et al., supra. Most children who respond to hGH, will respond to GH-RH. This is because most GH-deficient children have a hypothalamic defect in GH release, and will show a GH response after the administration of analogs of the hypothalamic hormone GH-RH. Thus repeated administration of GH-RH promotes linear growth. GH-RH(1-29)NH.sub.2 given subcutaneously twice a day promoted linear growth in approximately 50% of a group of GH-deficient children (Ross et al, cited above). A small group of severely GH-deficient children will respond to GH-RH after 6 (six) months of treatment.

Further Clinical Applications of Agonistic Analogs of GH-RH in Children with Growth Retardation 1. As a screening test for growth hormone deficiency.
2. Treatment of Hypothalamic GH-RH deficiency.
3. Constitutional growth delay.
4. Turner Syndrome.
5. Familial short stature.
6. Prepubertal children with chronic renal insufficiency and severe growth retardation.
7. Infants and children with intrauterine growth retardation.
8. Children with GH deficiency following radiotherapy for pituitary or hypothalamic lesions.
9. Children on long-term treatment with glucocorticoids and growing at subnormal rate.

Further Clinical Applications of Agonistic Analogs of GH-RH in Adults

1. Geriatric Patients: To reduce the loss of muscle, bone and skin mass and lessen the increase of body fat that normally accompanies the aging process.

2. Catabolic states
3. Wound healing
4. Delayed healing of fractures
5. Osteoporosis
6. Obesity
7. As an adjunct to total parenteral nutrition in malnourished patients with chronic obstructive pulmonary disease
8. Cardiac failure
9. GH-RH agonists could be used during and after space flights to counteract the decrease in GH secretion. Weightlessness of space flight significantly decreases the release of growth hormone, which could explain the bone loss and muscle weakness many astronauts experience after prolonged space flights.

Therapeutic Uses of GH-RH Agonists

Successful treatment of growth hormone deficiency using hGH-RH and hGH-RH(1-40) has been reported in Takano K et al., Endocrinol. Japan 35; 775-781 (1988) and Thorner M. O. et al., N. Engl. J. Med., 312, 4-9 (1985) respectively. Therapeutic treatments using hGH-RH(1-29) have also been reported against human growth hormone deficiency, Ross R. J. M. et al., Lancet 1:5-8, (1987); decreased GH in elderly males, Corpas et al., J. Clin. Endocrin. Metabol. 75, 530-535 (1992); and idiopathic short stature, Kirk J. M. W. et al., Clinical Endocrinol. 41, 487-493 (1994). Since earlier analogs of hGH-RH have successfully treated conditions associated with low levels of GH, it is not surprising that the novel synthetic hGH-RH peptides described herein also induce release of GH and are novel therapeutic treatments for these conditions.

Indeed, this suitability as a therapeutic agent is confirmed by the in vivo testing reported below. This testing is considered reasonably predictive of the results which one could expect in treating higher mammals, including humans. From the results below, one would expect that the novel synthetic hGH-RH analogs to be useful in therapeutically treating humans for growth hormone deficiency, as well as for a number of other conditions growing out of very low levels of GH. Thus, the invention further comprises a method of treating human growth hormone deficiency comprising administering from 0.01 .mu.g to 2 .mu.g of a peptide per day per kg body weight.

The synthetic peptides may be formulated in a pharmaceutical dosage form with an excipient and administered to humans or animals for therapeutic or diagnostic purposes. More particularly, the synthetic peptides may be used to promote the growth of warm-blooded animals, as, in humans, to treat human growth deficiency by stimulating in vivo synthesis and/or release of endogenous GH; to treat certain physiological conditions such as severe growth retardation due to chronic renal in-sufficiency; to offset certain effects of aging, e.g., reducing loss of muscle and bone loss; to accelerate healing and tissue repair; to improve feed utilization, thereby increasing lean/fat ratio favoring muscle gain at the cost of fat; and also to enhance milk production in lactating cattle. Further, the synthetic peptides may be used in a method to ascertain endogenous physiological ability to produce hGH.

EXAMPLES

The present invention is described in connection with the following examples which are set forth for the purposes of illustration only. In the examples, optically active protected amino acids in the L-configuration are used except where specifically noted. The following Examples set forth suitable methods of synthesizing the novel GH-RH antagonists by the solid-phase technique.

Example I

N-Me-Tyr$^1$-Ala$^2$-Asp$^3$-Ala$^4$-Ile$^5$-Fpa5$^6$-Thr$^7$-Gln$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-Agm$^{29}$ (Peptide 20103)

(SEQ ID NO: 2)
[N-Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGH-RH(1-29)

The synthesis is conducted in a stepwise manner using manual solid phase peptide synthesis equipment. Two methods have been used for the synthesis of peptides having Agm at the C-terminus. In one case, the starting material of the synthesis is Boc-agmatine-N$^G$-sulfonyl-phenoxyacetyl-MBHA (Boc-Agm-SPA-MBHA) resin with a substitution of 0.3 mmol/g, which was obtained commercially from California Peptide Research, Inc. (Napa, Calif.). The synthesis of this resin has been described in U.S. Pat. No. 4,914,189 and in the scientific literature (Zarandi M, Serfozo P, Zsigo J, Bokser L, Janaky T, Olsen D B, Bajusz S, Schally A V, Int. J. Peptide Protein Res. 39: 211-217, 1992), hereby incorporated by reference. Briefly, Boc-Agm-SPA-MBHA resin (1.67 g, 0.50 mmol) is pre-swollen in DCM and then the deprotection and neutralization protocols described in Table 2 are performed in order to remove the Boc protecting group and prepare the peptide-resin for coupling of the next amino acid. In another case, Agm-sulfonyl-polystyrene (PS) resin is used [1% DVB, 100-200 mesh, 0.74 mmol/g, American Peptide Company (Sunnyvale, Calif.)]. Briefly, Agm-sulfonyl-PS resin (680 mg, 0.50 mmol) is neutralized with 5% DIEA in DCM and washed according to the protocol described in Table 2. The solution of Boc-Asp(OcHx)-OH (475 mg, 1.5 mmol) in DMF-DCM (1:1) is shaken with the neutralized resin and DIC (235 μL, 1.5 mmol) in a manual solid phase peptide synthesis apparatus for 1 hour. Then, the deprotection and neutralization protocols described in Table 2 are performed in order to remove the Boc protecting group and prepare the peptide-resin for coupling of the next amino acid. The synthesis is continued in a stepwise manner using manual solid phase peptide synthesis equipment in both cases, and the peptide chain is built stepwise by coupling the following protected amino acids in the indicated order on the resin to obtain the desired peptide sequence: Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-Ala-OH, Boc-N-Me-Tyr(2BrZ)-OH.

These protected amino acid residues (also commonly available from NovaBiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 μL, 1.5 mmol) with the exceptions of Boc-Asn-OH and Boc-Gln-OH which are coupled with their pre-formed HOBt esters.

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 68 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 Å pore size, 3 μm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 68 mg of crude peptide is dissolved in $AcOH/H_2O$, stirred, filtered and applied on an XBridge Prep OBD™ reversed phase column (4.6×250 mm, packed with $C_{18}$ silica gel, 300 Å pore size, 5 μm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 18 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 20105, Peptide 20107, Peptide 20109, Peptide 20110, Peptide 20111, Peptide 20113, Peptide 20115, Peptide 20350, Peptide 20351, Peptide 20356, Peptide 20357, Peptide 20358, Peptide 20359, Peptide 20360, Peptide 20361, Peptide 20363, Peptide 20367, Peptide 20370, Peptide 20371, Peptide 20372, Peptide 20373, Peptide 20374, Peptide 20375, Peptide 20376, are synthesized in the same manner as Peptide 20103, except that these peptides also contain other amino acid substitutions in the peptide sequence, and acyl moieties at their N-termini. The details for these syntheses are set forth below.

For the synthesis of Peptide 20105, the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$, Agm$^{29}$]hGH-RH(1-29), the following protected amino acids are coupled in the indicated order on the Agm-$SO_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20107, the chemical structure of which is [[N-Me-Tyr$^1$, Fpa5$^6$, Ala$^8$, Orn$^{12}$, Abu$^{15}$, Orn$^{21}$, Nle$^{27}$, Asp$^{28}$, Agm$^{29}$]hGH-RH(1-29) (SEQ ID NO: 3), the following protected amino acids are coupled in the indicated order on the Agm-$SO_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20109, the chemical structure of which is [N-Me-Tyr\D-Ala$^2$, Fpa5$^6$, Ala$^8$, Orn$^{12}$, Abu$^{15}$, Orn$^{21}$, Nle$^{27}$, Asp$^{28}$, Agm$^{29}$]hGH-RH(1-29), the following protected amino acids are coupled in the indicated order on the Agm-$SO_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20110, the chemical structure of which is [N-Me-Tyr$^1$, D-Ala$^2$, Fpa5$^6$, Orn$^{12}$, Abu$^{15}$, Orn$^{21}$, Nle$^{27}$, Agm$^{29}$]hGH-RH(1-29), the following protected amino acids are coupled in the indicated order on the Agm-$SO_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20111, the chemical structure of which is [N-Me-Tyr$^1$, D-Ala$^2$, Fpa5$^6$, Thr$^8$, Orn$^{12}$, Abu$^{15}$, Orn$^{21}$, Nle$^{27}$, Asp$^{28}$, Agm$^{29}$]hGH-RH(1-29), the following protected amino acids are coupled in the indicated order on the resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20113, the chemical structure of which is [N-Me-Tyr$^1$, Fpa5$^6$, Orn$^{12}$, Abu$^{15}$, Orn$^{21}$, Nle$^{27}$, Asp$^{28}$, Agm$^{29}$]hGH-RH(1-29) (SEQ ID NO: 4), the following protected amino acids are coupled in the indicated order on the Agm-$SO_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc- Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20115, the chemical structure of which is [N-Me-Tyr$^1$, Fpa5$^6$, Thr$^8$, Orn$^{12}$, Abu$^{15}$, Orn$^{21}$, Nle$^{27}$, Asp$^{28}$, Agm$^{29}$]hGH-RH(1-29) (SEQ ID NO: 5), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Fpa5-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20117 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGH-RH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20350 the chemical structure of which [Dat$^1$, D-Ala$^2$, Gln$^8$, Orn$^{12}$, Abu$^{15}$, Orn$^{21}$, Nle$^{27}$, Asp$^{28}$, Agm$^{29}$]hGH-RH(1-29), the following protected amino acids are coupled in the indicated order on the resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Dat-OH.

For the synthesis of Peptide 20351 the chemical structure of which [Ac—N-Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGH-RH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Ac—N-Me-Tyr(2BrZ)-OH.

For the synthesis of Peptide 20356, the chemical structure of which [N-Me-Tyr$^1$, Gln$^8$, Orn$^{12}$, Abu$^{15}$, Orn$^{21}$, Nle$^{27}$, Asp$^{28}$, Agm$^{29}$]hGH-RH(1-29) (SEQ ID NO: 6), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20357 the chemical structure of which [Dat$^1$, D-Ala$^2$, N-Me-Ala$^8$, Orn$^{12}$, Abu$^{15}$, Orn$^{21}$, Nle$^{27}$, Asp$^{28}$, Agm$^{29}$]hGH-RH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-N-Me-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Dat-OH.

For the synthesis of Peptide 20358 the chemical structure of which [Dat$^1$, D-Ala$^2$, N-Me-Ala$^8$, Orn$^{12}$, Abu$^{15}$, Orn$^{21}$, Nle$^{27}$, Asp$^{28}$, Agm$^{29}$]hGH-RH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-N-Me-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20359, the chemical structure of which is [N-Me-Tyr$^1$, D-Ala$^2$, Fpa5$^6$, Orn$^{12}$, Abu$^{15}$, Orn$^{21}$, Nle$^{27}$, Asp$^{28}$, Agm]hGH-RH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20360, the chemical structure of which is [N-Me-Tyr$^1$, D-Ala$^2$, Thr$^8$, Orn$^{12}$, Abu$^{15}$, Orn$^{21}$, Nle$^{27}$, Asp$^{28}$, Agm$^{29}$]hGH-RH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20361, the chemical structure of which is [N-Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGH-RH(1-29), the following protected amino acids are coupled in the indicated order on the Agm-SO$_2$—PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20367, the chemical structure of which is [N-Me-Tyr$^1$, D-Ala$^2$, Orn$^{12}$, Abu$^{15}$, Orn$^{21}$, Nle$^{27}$, Asp²⁸, Agm²⁹]hGH-RH(1-29), the following protected amino acids are coupled in the indicated order on the Agm-SO₂—PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20370, the chemical structure of which is [N-Me-Tyr¹, Orn¹², Abu¹⁵, Orn²¹, Nle²⁷, Asp²⁸, Agm²⁹]hGH-RH(1-29) (SEQ ID NO: 7), the following protected amino acids are coupled in the indicated order on the Agm-SO₂-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20371, the chemical structure of which is [N-Me-Tyr¹, Thr⁸, Orn¹², Abu¹⁵, Orn²¹, Nle²⁷, Asp²⁸, Agm²⁹]hGH-RH(1-29) (SEQ ID NO: 8), the following protected amino acids are coupled in the indicated order on the Agm-SO₂-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20372, the chemical structure of which is [N-Me-Tyr¹, Orn¹², Abu¹⁵, Orn²¹, Nle²⁷, Asp²⁸Agm²⁹]hGH-RH(1-29) (SEQ ID NO: 9), the following protected amino acids are coupled in the indicated order on the Agm-SO₂-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20373, the chemical structure of which is [N-Me-Tyr¹, Gln⁸, Orn¹², Abu¹⁵, Orn²¹, Nle²⁷, Agm²⁹]hGH-RH(1-29) (SEQ ID NO: 10), the following protected amino acids are coupled in the indicated order on the Agm-SO₂-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20374, the chemical structure of which is [N-Me-Tyr¹, Orn¹², Abu¹⁵, Orn²¹, Nle²⁷, Agm²⁹]hGH-RH(1-29) (SEQ ID NO: 11), the following protected amino acids are coupled in the indicated order on the Agm-SO₂-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20375, the chemical structure of which is [N-Me-Tyr¹, Thr⁸, Orn¹², Abu¹⁵, Orn²¹, Nle²⁷, Agm²⁹]hGH-RH(1-29) (SEQ ID NO: 12), the following protected amino acids are coupled in the indicated order on the Agm-SO₂-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20376, the chemical structure of which is [N-Me-Tyr¹, Orn¹², Abu¹⁵, Orn²¹, Nle²⁷, Agm²⁹]hGH-RH(1-29) (SEQ ID NO: 13), the following protected amino acids are coupled in the indicated order on the Agm-SO₂-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

HF cleavage and deprotection, and subsequent purification by semipreparative HPLC of Peptide 20105, Peptide 20107, Peptide 20109, Peptide 20110, Peptide 20111, Peptide 20113, Peptide 20115, Peptide 20350, Peptide 20351, Peptide 20356, Peptide 357, Peptide 20358, Peptide 20359, Peptide 20360, Peptide 20361, Peptide 20363, Peptide 20367, Peptide 20370, Peptide 20371, Peptide 20372, Peptide 20373, Peptide 20374, Peptide 20375, Peptide 20376 are done as described in the case of Peptide 20103. The purified compounds are judged to be substantially (>95%) pure by analytical HPLC. Their molecular masses are checked by electrospray mass spectrometry, and the expected amino acid compositions are confirmed by amino acid analysis.

Example II

Dat¹-D-Ala²-Asp³-Ala⁴-Ile⁵-Phe⁶-Thr⁷-Asn⁸-Ser⁹-Tyr¹⁰-Arg¹¹-Orn¹²-Val¹³-Leu¹⁴-Abu¹⁵-Gln¹⁶-Leu¹⁷-Ser¹⁸-Ala¹⁹-Arg²⁰Orn²¹-Leu²²-Leu²³-Gln²⁴-Asp²⁵-Ile²⁶-Nle²⁷-Asp²⁸-Arg²⁹-Amc³⁰-NH₂ (Peptide 21300)

[Dat¹, D-Ala², Orn¹², Abu¹⁵, Orn²¹, Nle²⁷, Asp²⁸, Amc³⁰]hGH-RH(1-30)NH₂.

The synthesis is conducted in a stepwise manner using manual solid phase peptide synthesis equipment. Briefly, para-methylbenzhydrylamine (MBHA) resin (100-200 mesh, 1% DVB, 0.7 mmol/g, Advanced Chemtech, Louisville, Ky.)

(350 mg, 0.50 mmol) is neutralized with 5% DIEA in DCM and washed according to the protocol described in Table 2. The solution of Boc-Amc-OH (390 mg, 1.5 mmol) in DMF-DCM (1:1) is shaken with the neutralized MBHA resin and DIC (235 µL, 1.5 mmol) in a manual solid phase peptide synthesis apparatus for 1 hour. After the completion of the coupling reaction is proved by negative ninhydrin test, the deprotection and neutralization protocols described in Table 2 are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg (Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH. These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free. The protected amino acids (1.5 mmol each) are coupled with DIC (235 µL, 1.5 mmol) with the exceptions of Boc-Asn-OH and Boc-Gln-OH which are coupled with their preformed HOBt esters.

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 130 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 Å pore size, 3 µm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 130 mg of crude peptide is dissolved in AcOH/H$_2$O, stirred, filtered and applied on an XBridge Prep OBD™ reversed phase column (4.6×250 mm, packed with C$_{18}$ silica gel, 300 Å pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 28 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 21301, Peptide, Peptide 21304, Peptide 21305, Peptide 21306, Peptide 21307, Peptide 21308, Peptide 21309, Peptide 21310, Peptide 21311, Peptide 22325, Peptide 22326, Peptide 22327, Peptide 22328, Peptide 22329, Peptide 22330, Peptide 22331, Peptide 22332, Peptide 22334, Peptide 22335, Peptide 22336, Peptide 22337, Peptide 23250, Peptide 23251, Peptide 23252, Peptide 23253, Peptide 23254, Peptide 23255, Peptide 23256, Peptide 23257, Peptide 23258, Peptide 23259, Peptide 23260, Peptide 23261, Peptide 23262, Peptide 23263, Peptide 23264, Peptide 23265, Peptide 24340, Peptide 24341, Peptide 24342, Peptide 24344, Peptide 24345, Peptide 24346, Peptide 24347, Peptide 24348, Peptide 25501, Peptide 25502, Peptide 25503, Peptide 25504, Peptide 25506, Peptide 25508, Peptide 25516, Peptide 26802, Peptide 26803, Peptide 2680, are synthesized in the same manner as Peptide 20300, except that these peptides also contain other amino acid substitutions in the peptide sequence, and/or different alpha- or omega-amino acid moieties at their C-termini. The details for these syntheses are set forth below.

For the synthesis of Peptide 21301, the chemical structure of which [N-Me-Tyr$^1$, Orn$^{12}$, Abu$^{15}$, Orn$^{21}$, Nle$^{27}$, Asp$^{28}$, Amc$^{30}$]hGH-RH(1-30)NH$_2$ (SEQ ID NO: 14), the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp (OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg (Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr (2BrZ)-OH.

For the synthesis of Peptide 21303, the chemical structure of which [N-Me-Tyr$^1$, D-Ala$^2$, Orn$^{12}$, Abu$^{15}$, Orn$^{21}$, Nle$^{27}$, Asp$^{28}$, Amc$^{30}$]hGH-RH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr (2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp (OcHx)-OH, Boc-D-Ala-OH, Boc-N-Me-Tyr(2BrZ)-OH.

For the synthesis of Peptide 21304, the chemical structure of which [Dat$^1$, D-Ala$^2$, Gln$^8$, Orn$^{12}$, Abu$^{15}$, Orn$^{21}$, Nle$^{27}$, Asp$^{28}$, Amc$^{30}$]hGH-RH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr (2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp (OcHx)-OH, Boc-D-Ala-OH, Dat-OH.

For the synthesis of Peptide 21305, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGH-RH(1-30)NH$_2$, the following protected amino acids are coupled in the indicated order on the MBHA resin: Boc-Amc-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 21306, the chemical structure of which [Dat$^1$, D-Ala$^2$, Thr$^8$, Orn$^{12}$, Abu$^{15}$, Orn$^{21}$, Nle$^{27}$, Asp$^{28}$, Amc$^{30}$]hGH-RH(1-30)NH), the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21307, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Amc$^{30}$]hGH-RH(1-30)NH$_2$, the following protected amino acids are coupled in the indicated order on the MBHA resin: Boc-Amc-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 21308, the chemical structure of which [Dat$^1$, D-Ala$^2$, Ala$^8$, Orn$^{12}$, Abu$^{15}$, Orn$^{21}$, Nle$^{27}$, Asp$^{28}$, Amc$^{30}$]hGH-RH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21309, the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Amc$^{30}$]hGH-RH(1-30)NH$_2$, the following protected amino acids are coupled in the indicated order on the MBHA resin: Boc-Amc-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 21310, the chemical structure of which [Dat$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGH-RH(1-30)NH$_2$, the following protected amino acids are coupled in the indicated order on the MBHA resin: Boc-Amc-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)-OH, Boc-His(Bom)-OH, Boc-Ala-OH, Boc-Ser (Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21311, the chemical structure of which [N-Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGH-RH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp (OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22325, the chemical structure of which [N-Me-Tyr$^1$, Gln$^8$, Orn$^{12}$, Abu$^{15}$, Orn$^{21}$, Nle$^{27}$, Asp$^{28}$, Apa$^{30}$]hGH-RH(1-30)NH$_2$(SEQ ID NO: 15), the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp (OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg (Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22326, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGH-RH(1-30)NH$_2$ the following protected amino acids are coupled in the indicated order on the MBHA resin: Boc-Apa-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22327, the chemical structure of which [Dat$^1$, Gln$^8$, Orn$^{12}$, Abu$^{15}$, Orn$^{21}$, Nle$^{27}$, Asp$^{28}$, Apa$^{30}$]hGH-RH(1-30)NH$_2$ (SEQ ID NO: 16), the following protected amino acids are coupled in the indicated order on the MBHA resin: Boc-Apa-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu- OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 22328, the chemical structure of which [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGH-RH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Ac-Tyr(2BrZ)-OH.

For the synthesis of Peptide 22329, the chemical structure of which [N-Me-Tyr$^1$, D-Ala$^2$, Orn$^{12}$, Abu$^{15}$, Orn$^{21}$, Nle$^{27}$, Asp$^{28}$, Apa$^{30}$]hGH-RH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22330, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Apa$^{30}$]hGH-RH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22331, the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Apa$^{30}$]hGH-RH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22332, the chemical structure of which [N-Me-Tyr$^1$, Orn$^{12}$, Abu$^{15}$, Orn$^{21}$, Nle$^{27}$, Asp$^{28}$, Apa$^{30}$]hGH-RH(1-30)NH$_2$ (SEQ ID NO: 17), the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 22334, the chemical structure of which [N-Me-Tyr$^1$, Orn$^{12}$, Abu$^{15}$, Orn$^{21}$, Nle$^{27}$, Apa$^{30}$]hGH-RH(1-30)NH$_2$ (SEQ ID NO: 18), the following protected amino acids are coupled in the indicated order on the MBHA resin: Boc-Apa-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 22335 the chemical structure of which [N-Me-Tyr$^1$, Thr$^8$, Orn$^{12}$, Abu$^{15}$, Orn$^{21}$, Nle$^{27}$, Asp$^{28}$, Apa$^{30}$]hGH-RH(1-30)NH$_2$ (SEQ ID NO: 19), the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 22336 the chemical structure of which [N-Me-Tyr$^1$, Ala$^8$, Orn$^{12}$, Abu$^{15}$, Orn$^{21}$, Nle$^{27}$, Asp$^{28}$, Apa$^+$]hGH-RH(1-30)NH$_2$ (SEQ ID NO: 20), the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 22337 the chemical structure of which [N-Me-Tyr$^1$, D-Ala$^2$, Cpa$^6$, Orn$^{12}$, Abu$^{15}$, Orn$^{21}$, Nle$^{27}$, Asp$^{28}$, Apa$^+$]hGH-RH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Cpa-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23250, the chemical structure of which [Dat$^1$, D-Ala$^2$, Gln$^8$, Orn$^{12}$, Abu$^{15}$, Orn$^{21}$, Nle$^{27}$, Asp$^{28}$, Har$^{30}$]hGH-RH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-

OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23251, the chemical structure of which [Dat$^1$, Gln$^8$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 21), the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23252, the chemical structure of which [Dat$^1$, D-Ala$^2$, Orn$^{12}$, Abu$^{15}$, Orn$^{21}$, Nile$^{27}$, Asp$^{28}$, Har$^{30}$]hGH-RH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23253, the chemical structure of which [Dat$^1$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 22), the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23254, the chemical structure of which [Dat$^1$, D-Ala$^2$, Thr$^8$, Orn$^{12}$, Abu$^{15}$, Orn$^{21}$, Nle$^{27}$, Asp$^{28}$, Har$^{30}$]hGH-RH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23255, the chemical structure of which [Dat$^1$ Thr$^8$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 23), the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23256, the chemical structure of which [Dat$^1$, D-Ala$^2$, Ala$^8$, Orn$^{12}$, Abu$^{15}$, Orn$^{21}$, Nle$^{27}$, Asp$^{28}$, Har$^{30}$]hGH-RH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23257, the chemical structure of which [Dat$^1$, Ala$^8$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 24), the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23258, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGH-RH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23259, the chemical structure of which [N-Me-Tyr$^1$, Gln$^8$, Orn$^{12}$, Abu$^{15}$, Orn$^{21}$, Nle$^{27}$, Asp$^{28}$, Har$^{30}$]hGH-RH(1-30)NH$_2$(SEQ ID NO: 25), the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 23260, the chemical structure of which [N-Me-Tyr$^1$, D-Ala$^2$, Orn$^{12}$, Abu$^{15}$, Orn$^{21}$, Nle$^{27}$, Asp$^{28}$, Har$^{30}$]hGH-RH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23261, the chemical structure of which [N-Me-Tyr$^1$, Orn$^{12}$, Abu$^{15}$, Orn$^{21}$, Nle$^{27}$, Asp$^{28}$, Har$^{30}$]hGH-RH(1-30)NH$_2$ (SEQ ID NO: 26), the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 23262, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGH-RH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23263, the chemical structure of which [N-Me-Tyr$^1$, Thr$^8$, Orn$^{12}$, Abu$^{15}$, Orn$^{21}$, Nle$^{27}$, Asp$^{28}$, Har$^{30}$]hGH-RH(1-30)NH$_2$(SEQ ID NO: 27), the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 23264, the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGH-RH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23265, the chemical structure of which [N-Me-Tyr$^1$, Ala$^8$, Orn$^{12}$, Abu$^{15}$, Orn$^{21}$, Asp$^{28}$, Har$^{30}$]hGH-RH(1-30)NH$_2$(SEQ ID NO: 28), the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 24340 the chemical structure of which [N-Me-Tyr$^1$, Gln$^8$, Orn$^{12}$, Abu$^{15}$, Orn$^{21}$, Nle$^{27}$, Asp$^{28}$, Aha$^{30}$]hGH-RH(1-30)NH$_2$(SEQ ID NO: 29), the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 24341 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGH-RH(1-30)NH$_2$) the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 24342 the chemical structure of which [Dat$^1$, Gln$^8$, Orn$^{12}$, Abu$^{15}$, Orn$^{21}$, Nle$^{27}$, Asp$^{28}$, Aha$^{30}$]hGH-RH(1-30)NH$_2$ (SEQ ID NO: 30), the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 24344 the chemical structure of which [Dat$^1$, D-Ala$^2$, Gln$^8$, Orn$^{12}$, Abu$^{15}$, Orn$^{21}$, Nle$^{27}$, Asp$^{28}$, Aha$^{30}$]hGH-RH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 24345 the chemical structure of which [N-Me-Tyr$^1$, D-Ala$^2$, Orn$^{12}$, Abu$^{15}$, Orn$^{21}$, Nle$^{27}$, Asp$^{28}$, Aha$^{30}$]hGH-RH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc- Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 24346 the chemical structure of which [N-Me-Tyr$^1$, D-Ala$^2$, Gln$^8$, Orn$^{12}$, Abu$^{15}$, Orn$^{21}$, Nle$^{27}$, Aha$^3$]hGH-RH(1-30)NH$_2$, the following protected amino acids are coupled in the indicated order on the MBHA resin: Boc-Aha-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 24347 the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGH-RH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 24348 the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGH-RH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 25501 the chemical structure of which [N-Me-Tyr$^1$, D-Ala$^2$, Orn$^{12}$, Abu$^{15}$, Orn$^{21}$, Nle$^{27}$, Gab$^{30}$]hGH-RH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 25502 the chemical structure of which [Dat$^1$, D-Ala$^2$, Fpa5$^6$, Orn$^{12}$, Abu$^{15}$, Orn$^{21}$, Nle$^{27}$, Gab$^{30}$]hGH-RH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Dat-OH.

For the synthesis of Peptide 25503 the chemical structure of which [N-Me-Tyr$^1$, Abu$^2$, Orn$^{12}$, Abu$^{15}$, Orn$^{21}$, Nle$^{27}$, Gab$^{30}$]hGH-RH(1-30)NH$_2$ (SEQ ID NO: 31), the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Abu-OH, Boc-N-Me-Tyr(2BrZ)-OH.

For the synthesis of Peptide 25504 the chemical structure of which [Dat$^1$, D-Abu$^2$, Orn$^{12}$, Abu$^{15}$, Orn$^{21}$, Nle$^{27}$, Gab$^{30}$]hGH-RH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Abu-OH, Dat-OH.

For the synthesis of Peptide 25506 the chemical structure of which [N-Me-Tyr$^1$, D-Abu$^2$, Orn$^{12}$, Abu$^{15}$, Orn$^{21}$, Nle$^{27}$, Gab$^{30}$]hGH-RH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Abu-OH, Boc-N-Me-Tyr(2BrZ)-OH.

For the synthesis of Peptide 25508 the chemical structure of which [Tfa-Tyr$^1$, D-Ala$^2$, Orn$^{12}$, Abu$^{15}$, Orn$^{21}$, Nle$^{27}$, Gab$^{30}$]hGH-RH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 25516 the chemical structure of which [N-Me-Tyr$^1$, D-Ala$^2$, Orn$^{12}$, Abu$^{15}$, Orn$^{21}$, Nle$^{27}$, Asp$^{28}$, Gab$^{30}$]hGH-RH(1-30)NH$_2$, the following protected amino acids are coupled in the indicated order on the MBHA resin: Boc-Gab-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc- Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 26802 the chemical structure of which [Dat$^1$, D-Ala$^2$, Thr$^8$, His$^{11}$, Orn$^{12}$, Abu$^{15}$, His$^{20}$, Orn$^{21}$, Nle$^{27}$, Ada$^{30}$]hGH-RH(1-30)NH$_2$, the following protected amino acids are coupled in the indicated order on the MBHA resin: Boc-Ada-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 26803 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGH-RH(1-30)NH$_2$, the following protected amino acids are coupled in the indicated order on the MBHA resin: Boc-Ada-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 26804 the chemical structure of which [N-Me-Tyr$^1$, D-Ala$^2$, Gln$^8$, Orn$^{12}$, Abu$^{15}$, Orn$^{21}$, Nle$^{27}$, Ada$^{30}$]hGH-RH(1-30)NH$_2$, the following protected amino acids are coupled in the indicated order on the MBHA resin: Boc-Ada-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

HF cleavage and deprotection, and subsequent purification by semipreparative HPLC of Peptide 21301, Peptide 21303, Peptide 21304, Peptide 21305, Peptide 21306, Peptide 21307, Peptide 21308, Peptide 21309, Peptide 21310, Peptide 21311, Peptide 22325, Peptide 22326, Peptide 22327, Peptide 22328, Peptide 22329, Peptide 22330, Peptide 22331, Peptide 22332, Peptide 22334, Peptide 22335, Peptide 22336, Peptide 22337, Peptide 23250, Peptide 23251, Peptide 23252, Peptide 23253, Peptide 23254, Peptide 23255, Peptide 23256, Peptide 23257, Peptide 23258, Peptide 23259, Peptide 23260, Peptide 23261, Peptide 23262, Peptide 23263, Peptide 23264, Peptide 23265, Peptide 24340, Peptide 24341, Peptide 24342, Peptide 24344, Peptide 24345, Peptide 24346, Peptide 24347, Peptide 24348, Peptide 25501, Peptide 25502, Peptide 25503, Peptide 25504, Peptide 25506, Peptide 25508, Peptide 25516, Peptide 26802, Peptide 26803, Peptide 2680 are done as described in the case of Peptide 21300. The purified compounds are judged to be substantially (>95%) pure by analytical HPLC. Their molecular masses are checked by electrospray mass spectrometry, and the expected amino acid compositions are confirmed by amino acid analysis Example III Dat$^1$-D-Ala$^2$-Asp$^3$-Ala$^4$-Ile$^5$-Phe$^6$-Thr$^7$-Asn$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-Arg$^{29}$-NH-CH$_3$ (Peptide 27400)

[Dat$^1$, D-Ala$^2$, Orn$^{12}$, Abu$^{15}$, Orn$^{21}$, Nle$^{27}$, Asp$^{28}$]hGH-RH(1-29)NH—CH$_3$ The synthesis is conducted in a stepwise manner using manual solid phase peptide synthesis equipment. Briefly, [3-[(Methyl-Fmoc-amino)methyl]-indol-1-yl]-acetyl AM resin (Nova Biochem, La Jolla, Calif.) (750 mg, 0.50 mmol) is deprotected with 20% piperidine in DMF for 5 and 15 minutes and washed according to the protocol described in Table 3. The solution of Fmoc-Arg(Pbf)-OH (975 mg, 1.5 mmol) in DMF is shaken with the washed resin and DIC (235 µL, 1.5 mmol) in a manual solid phase peptide synthesis apparatus for 1 hour. After washing the resin three times with DMF, the coupling reaction was repeated as described above. After the repeated coupling and after the completion of the reaction is proved by negative ninhydrin test, the deprotection and neutralization protocols described in Table 3 are performed in order to remove the Fmoc protecting group and prepare the peptide-resin for coupling of the next amino acid. The synthesis is continued and the peptide chain is built stepwise by coupling the following protected amino acids in the indicated order on the resin to obtain the desired peptide sequence: Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Dat-OH.

These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 µL, 1.5 mmol) with the exceptions of Fmoc-Asn(Trt)-OH and Fmoc-Gln(Trt)-OH which are coupled with HBTU reagent.

In order to cleave the peptide from the resin and deprotect it, a portion of 250 mg of the dried peptide resin is stirred with 2.5 mL cleavage cocktail (94% TFA, 3% H$_2$O, 1.5% m-cresol, and 1.5% phenol) at room temperature for 3 hours. To induce peptide precipitation, the cleavage mixture is added dropwise to cold (preferably −20° C.) ether. The precipitated material is collected by filtration or centrifugation and is washed three times with cold ether. The cleaved and deprotected peptide is dissolved in 50% acetic acid and separated from the resin by filtration. After dilution with water and lyophilization, 118 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 Å pore size, 3 µm particle size) (Supeico, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 118 mg of crude peptide is dissolved in AcOH/$H_2$O, stirred, filtered and applied on an XBridge Prep OBD™ reversed phase column (4.6×250 mm, packed with $C_{18}$ silica gel, 300 Å pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 19 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 27401, Peptide 27403, Peptide 27404, Peptide 27405, Peptide 27406, Peptide 27407, Peptide 27408, Peptide 27409, Peptide 27410, Peptide 27411, Peptide 412, Peptide 27413, Peptide 27414, Peptide 27415, Peptide 27416, Peptide 27417, Peptide 27418, Peptide 27419, Peptide 27422, Peptide 27423, Peptide 27424, Peptide 27425, Peptide 27440, Peptide 27441, Peptide 27442, Peptide 27443, Peptide 27444, Peptide 27445, Peptide 27446, Peptide 27447, Peptide 27448, Peptide 27449, Peptide 27450, Peptide 27451 are synthesized in the same manner as Peptide 27400, except that these peptides also contain other amino acid substitutions in the peptide sequence. The details for these syntheses are set forth below.

For the synthesis of Peptide 27401, the chemical structure of which [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGH-RH(1-29)NH—CH$_3$, the following protected amino acids are coupled in the indicated order on the deprotected [3-[(Methyl-Fmoc-amino)methyl]-indol-1-yl]-acetyl Am resin: Fmoc-D-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Dat-OH.

For the synthesis of Peptide 27403, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27404, the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27405, the chemical structure of which [N-Me-Tyr$^1$, Orn$^{12}$, Abu$^{15}$, Orn$^{21}$, Nle$^{27}$]hGH-RH (1-29)NH—CH$_3$ (SEQ ID NO: 32), the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Fmoc-N-Me-Tyr(tBu)-OH.

For the synthesis of Peptide 27406, the chemical structure of which [N-Me-Tyr$^1$, Gln$^8$, Orn$^{12}$, Abu$^{15}$, Orn$^{21}$, Nle$^{27}$, Asp$^{28}$]hGH-RH(1-29)NH—CH$_3$ (SEQ ID NO: 33), the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Fmoc-N-Me-Tyr(tBu)-OH.

For the synthesis of Peptide 27407, the chemical structure of which [Dat$^1$, Gln$^8$, Orn$^{12}$, Abu$^{15}$, Orn$^{21}$, Nle$^{27}$, Asp$^{28}$]hGH-RH(1-29)NH—CH$_3$ (SEQ ID NO: 34), the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Dat-OH.

For the synthesis of Peptide 27408, the chemical structure of which [Dat$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Dat-OH.

For the synthesis of Peptide 27409, the chemical structure of which [N-Me-Tyr$^1$, D-Ala$^2$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27410, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27411 the chemical structure of which [N-Me-Tyr$^1$, D-Ala$^2$, Thr$^8$, Orn$^{12}$, Abu$^{15}$, Orn$^{21}$, Nle$^{27}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27412 the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Ala-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27413 the chemical structure of which [Dat$^1$, Gln$^8$, His$^{11}$, Orn$^{12}$, Abu$^{15}$, His$^{20}$, Orn$^{21}$, Nle$^{27}$, Asp$^{28}$]hGH-RH(1-29)NH—CH$_3$ (SEQ ID NO: 35), the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-His(Trt)-OH, Fmoc-Tyr(tBu)-OH, Fmoc-Ser(Trt)-OH, Fmoc-Gln-OH, Fmoc-Thr(tBu)-OH, Fmoc-Phe-OH, Fmoc-Ile-OH, Fmoc-Ala-OH, Fmoc-Asp(OBu$^t$)—OH, Fmoc-D-Ala-OH, Dat-OH.

For the synthesis of Peptide 27414 the chemical structure of which [N-Me-Tyr$^1$, D-Ala$^2$, Fpa5$^6$, Orn$^{12}$, Abu$^{15}$, Orn$^{21}$, Nle$^{27}$, Gab$^{30}$]hGH-RH(1-30)NH—CH$_3$, the following protected amino acids are coupled in the indicated order on the deprotected [3-[(Methyl-Fmoc-amino)methyl]-indol-1-yl]-acetyl AM resin: Fmoc-Gab-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27415 the chemical structure of which [N-Me-Tyr$^1$, Orn$^{12}$, Abu$^{15}$, Orn$^{21}$, Nle$^{27}$, Gab$^{30}$]hGH-RH(1-30)NH—CH$_3$ (SEQ ID NO: 36), the following protected amino acids are coupled in the indicated order on the deprotected [3-[(Methyl-Fmoc-amino)methyl]-indol-1-yl]-acetyl AM resin: Fmoc-Gab-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Fmoc-N-Me-Tyr(tBu)-OH.

For the synthesis of Peptide 27416 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-His(Trt)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27417 the chemical structure of which [Ac-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Ac-Tyr(tBu)-OH.

For the synthesis of Peptide 27418 the chemical structure of which [Ac-Tyr$^1$, D-Ala$^2$, Fpa5$^6$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Ac-Tyr(tBu)-OH.

For the synthesis of Peptide 27419 the chemical structure of which [Ac-Tyr$^1$, Thr$^8$, Orn$^{12}$, Abu$^{15}$, Orn$^{21}$, Nle$^{27}$]hGH-RH(1-29)NH—CH$_3$ (SEQ ID NO: 37), the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Ac-Tyr(tBu)-OH.

For the synthesis of Peptide 27422 the chemical structure of which [N-Me-D-Tyr$^1$, Gln$^8$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Fmoc-N-Me-Tyr(tBu)-OH.

For the synthesis of Peptide 27423 the chemical structure of which [N-Me-D-Tyr$^1$, D-Ala$^2$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 2742.4 the chemical structure of which [Dat$^1$, Thr$^8$, Orn$^{12}$, Abu$^{15}$, Orn$^{21}$, Nle$^{27}$]hGH-RH(1-29)NH—CH$_3$ (SEQ ID NO: 38), the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Dat-OH.

For the synthesis of Peptide 27425 the chemical structure of which [N-Me-D-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27440 the chemical structure of which [Dat$^1$ Gln$^8$, Orn$^{12}$, Abu$^{15}$, Orn$^{21}$, Nle$^{27}$, Asp$^{28}$, D-Arg$^{29}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Dat-OH.

For the synthesis of Peptide 27441 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-

OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27442 the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27443 the chemical structure of which [N-Me-Tyr$^1$, Orn$^{12}$, Abu$^{15}$, Orn$^{21}$, Nle$^{27}$, D-Arg$^{29}$] hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tfiu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Fmoc-N-Me-Tyr(tBu)-OH.

For the synthesis of Peptide 27444 the chemical structure of which [N-Me-Tyr$^1$, D-Ala$^2$, Orn$^{12}$, Abu$^{15}$, Orn$^{21}$, Nle$^{27}$, Asp$^{28}$, D-Arg$^{29}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27445 the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27446 the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGH-RH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Ala-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27447 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Apa$^+$]hGH-RH(1-30)NH—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27448 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGH-RH(1-30)NH—CH$_3$, the following protected amino acids are coupled in the indicated order on the deprotected [3-[(Methyl-Fmoc-amino)methyl]-indol-1-yl]-acetyl AM resin: Fmoc-Aha-OH, Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27449 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGH-RH(1-30)NH—CH$_3$, the following protected amino acids are coupled in the indicated order on the deprotected [3-[(Methyl-Fmoc-amino)methyl]-indol-1-yl]-acetyl AM resin: Fmoc-Amc-OH, Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27450 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGH-RH(1-30)NH—CH$_3$, the following protected amino acids are coupled in the indicated order on the deprotected [3-[(Methyl-Fmoc-amino)methyl]-indol-1-yl]-acetyl AM resin: Fmoc-Har(Pbf)-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27451 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Aha$^3$]hGH-RH(1-30)NH—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH Fmoc-His(Trt)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

TFA cleavage and deprotection with the cleavage cocktail, and subsequent purification by semipreparative HPLC of Peptide 27401, Peptide 27403, Peptide 27404, Peptide 27405, Peptide 27406, Peptide 27407, Peptide 27408, Peptide 27409, Peptide 27410, Peptide 27411, Peptide 27412, Peptide 27413, Peptide 27414, Peptide 27415, Peptide 27416, Peptide 27417, Peptide 27418, Peptide 27419, Peptide 27422, Peptide 27423, Peptide 27424, Peptide 27425, Peptide 27440, Peptide 27441, Peptide 27442, Peptide 27443, Peptide 27444, Peptide 27445, Peptide 27446, Peptide 27447, Peptide 27448, Peptide 27449, Peptide 27450, Peptide 27451 are done as described in the case of Peptide 27400. The purified compounds are judged to be substantially (>95%) pure by analytical HPLC. Their molecular masses are checked by electrospray mass spectrometry, and the expected amino acid compositions are confirmed by amino acid analysis.

Example IV

N-Me-Tyr$^1$-D-Ala$^2$-Asp$^3$-Ala$^4$-Ile$^5$-Phe$^6$-Thr$^7$-Gln$^8$-

Ser$^9$-Tyr$^{10}$-Arg$^{11}$-Orn$^{12}$-Val$^{13}$-Leu$^{14}$-Abu$^{15}$-Gln$^{16}$-

Leu$^{17}$-Ser$^{18}$-Ala$^{19}$-Arg$^{20}$-Orn$^{21}$-Leu$^{22}$-Leu$^{23}$-Gln$^{24}$-

Asp$^{25}$-Ile$^{26}$-Nle$^{27}$-Asp$^{28}$-Arg$^{29}$-NH-CH$_2$-CH$_3$ (Peptide 28420)

N-Me-Tyr$^1$, D-Ala$^2$, Gln$^8$, Orn$^{12}$, Abu$^{15}$, Orn$^{21}$,

Nle$^{27}$, Asp$^{28}$]hGH-RH(1-29)NH-CH$_2$-CH$_3$

The synthesis is conducted in a stepwise manner using manual solid phase peptide synthesis equipment. Briefly, 3-[(Ethyl-Fmoc-amino)methyl]-indol-1-A-acetyl AM resin (Nova Biochem, La Jolla, Calif.) (610 mg, 0.50 mmol) is deprotected with 20% piperidine in DMF for 5 and 15 minutes and washed according to the protocol described in Table 3. The solution of Fmoc-Arg(Pbf)-OH (975 mg, 1.5 mmol) in DMF is shaken with the washed resin and DIC (235 μL, 1.5 mmol) in a manual solid phase peptide synthesis apparatus for 1 hour. After washing the resin three times with DMF, the coupling reaction was repeated as described above. After the repeated coupling and after the completion of the reaction is proved by negative ninhydrin test, the deprotection and neutralization protocols described in Table 3 are performed in order to remove the Fmoc protecting group and prepare the peptide-resin for coupling of the next amino acid. The synthesis is continued and the peptide chain is built stepwise by coupling the following protected amino acids in the indicated order on the resin to obtain the desired peptide sequence: Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxy-terminus of each residue is free.

The protected amino acids (1.5 mmol each) are coupled with DIC (235 μL, 1.5 mmol) with the exceptions of Fmoc-Asn(Trt)-OH and Fmoc-Gln(Trt)-OH which are coupled with HBTU reagent.

In order to cleave the peptide from the resin and deprotect it, a portion of 250 mg of the dried peptide resin is stirred with 2.5 mL of cleavage cocktail (94% TFA, 3% H$_2$O, 1.5% m-cresol, and 1.5% phenol) at room temperature for 3 hours. To induce peptide precipitation, the cleavage mixture is added dropwise to cold (preferably −20° C.) ether. The precipitated material is collected by filtration or centrifugation and is washed three times with cold ether. The cleaved and deprotected peptide is dissolved in 50% acetic acid and separated from the resin by filtration. After dilution with water and lyophilization, 110 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 Å pore size, 3 μm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 110 mg of crude peptide is dissolved in AcOH/H$_2$O, stirred, filtered and applied on an XBridge Prep OBD™ reversed phase column (4.6×250 mm, packed with C$_{i8}$ silica gel, 300 Å pore size, 5 μm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 16 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 28421, Peptide 28430, Peptide 28431, Peptide 28460, Peptide 28461, Peptide 28462, Peptide 28463, Peptide 28464, Peptide 28465, Peptide 28466, Peptide 28467, Peptide 28468, Peptide 28469, Peptide 28470, Peptide 28471, Peptide 28472, Peptide 28473, Peptide 28474, Peptide 28475, Peptide 28476, Peptide 28477, Peptide 28478, Peptide 28479 are synthesized in the same manner as Peptide 28460, except that these peptides also contain other amino acid substitutions in the peptide sequence. The details for these syntheses are set forth below.

For the synthesis of Peptide 28421 the chemical structure of which [N-Me-Tyr$^1$, D-Ala$^2$, Orn$^{12}$, Abu$^{15}$, Orn$^{21}$, Nle$^{27}$, Asp$^{28}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28430 the chemical structure of which [N-Me-Tyr$^1$, D-Ala$^2$, Gln$^8$, Orn$^{12}$, Abu$^{15}$, Orn$^{21}$, Nle$^{27}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(tBu)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28431 the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(tBu)-OH, Fmoc-D-Ala-OH, Fmoc-N-Me-Tyr(tBu)-OH.

For the synthesis of Peptide 28460 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28462 the chemical structure of which [N-Me-Tyr$^1$, D-Ala$^2$, Fpa5$^6$, Orn$^{12}$, Abu$^{15}$, Orn$^{21}$, Nle$^{27}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28463 the chemical structure of which [N-Me-Tyr$^1$, D-Ala$^2$, Orn$^{12}$, Abu$^{15}$, Orn$^{21}$, Nle$^{27}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28464 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28465 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$]hGH-RH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28466 the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$]hGH-RH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28467 the chemical structure of which [N-Me-Tyr$^1$, D-Ala$^2$, Orn$^{12}$, Abu$^{15}$, Orn$^{21}$, Nle$^{27}$, Asp$^{28}$]hGH-RH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28468 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGH-RH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28469 the chemical structure of which [Dat$^1$, D-Ala$^2$, Gln$^8$, Orn$^{12}$, Abu$^{15}$, Orn$^{21}$, Nle$^{27}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Dat-OH.

For the synthesis of Peptide 28470 the chemical structure of which [Dat$^1$, D-Ala$^2$, Orn$^{12}$, Abu$^{15}$, Orn$^{21}$, Nle$^{27}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Ser(Trt)-OH, Fmoc-Nle-OH, Fmoc-Ile-OH, Fmoc-AspfOBuyOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Dat-OH.

For the synthesis of Peptide 28471 the chemical structure of which [Dat$^1$, D-Ala$^2$, Gln$^8$, Orn$^{12}$, Abu$^{15}$, Orn$^{21}$, Nle$^{27}$, Asp$^{28}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)—H, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Dat-OH.

For the synthesis of Peptide 28472 the chemical structure of which [Dat$^1$, D-Ala$^2$, Fpa5$^6$, Gln$^8$, Orn$^{12}$, Abu$^{15}$, Orn$^{21}$, Nle$^{27}$, Asp$^{28}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Dat-OH.

For the synthesis of Peptide 28473 the chemical structure of which [Dat$^1$, D-Ala$^2$, Fpa5$^6$, Orn$^{12}$, Abu$^{15}$, Orn$^{21}$, Nle$^{27}$, Asp$^{28}$]hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc- Fpa5-OH, Fmoc-Ile-OH, Fmoc-Ala-OH, Fmoc-Asp(OBu$^t$)-OH, Fmoc-D-Ala-OH, Dat-OH.

For the synthesis of Peptide 28474 the chemical structure of which [Dat$^1$, D-Ala$^2$, Orn$^{12}$, Abu$^{15}$, Orn$^{21}$, Nle$^{27}$, Asp$^{28}$] hGH-RH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Dat-OH.

For the synthesis of Peptide 28475 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Apa$^+$]hGH-RH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28476 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGH-RH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Aha-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28477 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGH-RH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Amc-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28478 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGH-RH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Har(Pbf)-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28479 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^+$]hGH-RH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-His(Trt)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

TFA cleavage and deprotection with the cleavage cocktail, and subsequent purification by semipreparative HPLC of Peptide 28421, Peptide 28430, Peptide 28431, Peptide 28460, Peptide 28461, Peptide 28462, Peptide 28463, Peptide 28464, Peptide 28465, Peptide 28466, Peptide 28467, Peptide 28468, Peptide 28469, Peptide 28470, Peptide 28471, Peptide 28472, Peptide 28473, Peptide 28474, Peptide 28475, Peptide 28476, Peptide 28477, Peptide 28478, Peptide 28479 are done as described in the case of Peptide 28420. The purified compounds are judged to be substantially (>95%) pure by analytical HPLC. Their molecular masses are checked by electrospray mass spectrometry, and the expected amino acid compositions are confirmed by amino acid analysis Example V Dat$^1$-D-Ala$^2$-Asp$^3$-Ala$^4$-Ile$^5$-Phe$^6$-Thr$^7$-Asn$^s$-Ser$^9$-

Tyr$^{10}$-Arg$^{11}$-Orn$^{12}$-Val$^{13}$-Leu$^{14}$-Abu$^{15}$-Gln$^{16}$-Leu$^{17}$-

Ser$^{18}$-Ala$^{19}$-Arg$^{20}$-Orn$^{21}$-Leu$^{22}$-Leu$^{23}$-Gln$^{24}$-Asp$^{25}$-

Ile$^{26}$-Nle$^{27}$-Ser$^{28}$-Arg$^{29}$-Gln-Gab$^{30}$-NH$_2$ (Peptide 29702)

Dat$^1$, D-Ala$^2$, Orn$^{12}$, Abu$^{15}$, Orn$^{21}$, Nle$^{27}$,

Gln-Gab$^{30}$]hGH-RH(1-30)-NH$_2$

The synthesis is conducted in a stepwise manner using manual solid phase peptide synthesis equipment. Briefly, para-methylbenzhydrylamine (MBHA) resin (Bachem, King of Prussia, Pa.) (720 mg, 0.50 mmol) is pre-swollen in DCM and neutralized with 5% DIEA in DCM and washed according to the protocol described in Table I. The solution of Boc-Gab-OH (265 mg, 1.5 mmol) in DMF-DCM (1:1) is shaken with the neutralized resin and DIC (235 μL, 1.5 mmol) in a manual solid phase peptide synthesis apparatus for 1 hour. After the completion of the coupling reaction is proved by negative ninhydrin test, the deprotection and neutralization protocols described in Table 2 are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 μL, 1.5 mmol) with the exceptions of Boc-Asn-OH and Boc-Gln-OH which are coupled with their preformed HOBt esters.

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 109 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 Å pore size, 3 μm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 109 mg of crude peptide is dissolved in AcOH/H$_2$O, stirred, filtered and applied on an XBridge Prep OBD™ reversed phase column (4.6×250 mm, packed with C$_{18}$ silica gel, 300 Å pore size, 5 μm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 27 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 29701, Peptide 29703, Peptide 29704, Peptide 29706, Peptide 29708, Peptide 29710, Peptide 29720, Peptide 29721, Peptide 29722, Peptide 29723, Peptide 29724 are synthesized in the same manner as Peptide 29702, except that these peptides also contain other amino acid substitutions in the peptide sequence, and acyl moieties at their N-termini. The details for these syntheses are set forth below.

For the synthesis of Peptide 29701 the chemical structure of which is [N-Me-Tyr$^1$, D-Ala$^2$, Gln$^8$, Orn$^{12}$, Abu$^{15}$, Orn$^{21}$, Nle$^{27}$, Asp$^{28}$, Gln-Gab$^{30}$]hGH-RH(1-30)NH$_2$; the following protected amino acids are coupled in the indicated order on the MBHA resin: Boc-Gab-OH, Boc-Gln-OH, Boc-Arg(Tos)-OH, Boc-Asp(OcHx)-OH, Boc-NLe-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(Bzl)-OH.

For the synthesis of peptide 29703 the chemical structure of which is N-Me-Tyr$^1$, Gln$^8$, Orn$^{12}$, Abu$^{15}$, Orn$^{21}$, Nle$^{27}$, Asp$^{28}$, Gln-Gab$^{30}$]hGH-RH(1-30)NH$_2$ (SEQ ID NO: 39) the following protected amino acids are coupled in the indicated order on the MBHA resin: Boc-Gab-OH, Boc-Gln-OH, Boc-Arg(Tos)-OH, Boc-Asp(OcHx)-OH, Boc-NLe-OH, Boc-Ile-OH, Boc-Asp(OcHx), Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2ClZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(Bzl)-OH.

For the synthesis of peptide 29704 the chemical structure of which is [Dat$^1$, D-Ala$^2$, Gln$^s$, Orn$^{12}$, Abu$^{15}$, Orn$^{21,22}$, Nle$^{27}$, Gln-Gab$^{30}$]hGH-RH(1-30)NH$_2$ the following protected amino acids are coupled in the indicated order on the MBHA resin: Boc-Gab-OH, Boc-Gln-OH, Boc-Arg(Tos)-OH, Boc-Asp(OcHx)-OH, Boc-NLe-OH, Boc-Asp(OcHx), Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2ClZ)-OH, Boc-Ser(Bzl)-OH, Boc-Gln-OH, Boc-Thr(Bzl)-OH, Boc-Phe-OH, Boc-Ala-OH, Boc-Asp(OcHx)-OH, Boc-Ala-OH, Boc-N-Me-Tyr(Bzl)-OH.

For the synthesis of Peptide 29706 the chemical structure of which [Tfa-Tyr$^1$, D-Abu$^2$, Gln$^8$, Orn$^{12}$, Abu$^{15}$, Orn$^{21}$, Nle$^{27}$, Gln-Gab$^{30}$]hGH-RH(1-30)NH$_2$, the following protected amino acids are coupled in the indicated order on the MBHA resin: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ala-OH, Boc-Asp(OcHx)-OH, Boc-D-Abu-OH, Tfa-Tyr-OH.

For the synthesis of Peptide 29708 the chemical structure of which [N-Me-Tyr$^1$, D-Ala$^2$, Fpa5$^6$, Orn$^{12}$, Abu$^{15}$, Orn$^{21}$, Nle$^{27}$, Gln-Gab$^{30}$]hGH-RH(1-30)NH$_2$, the following protected amino acids are coupled in the indicated order on the MBHA resin: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ala-OH, Boc-Asp(OcHx)-OH, Boc-D-Ala-OH, Boc-N-Me-Tyr(2BrZ)-OH.

For the synthesis of Peptide 29710 the chemical structure of which [N-Me-Tyr$^1$, D-Ala$^2$, Fpa5$^6$, Ala$^8$, Orn$^{12}$, Abu$^{15}$, Orn$^{21}$, Nle$^{27}$, Gln-Gab$^{30}$]hGH-RH(1-30)NH$_2$, the following protected amino acids are coupled in the indicated order on the MBHA resin: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 29720 the chemical structure of which [Dat$^1$, D-Ala$^2$, Orn$^{12}$, Abu$^{15}$, Orn$^{21}$, Nle$^{27}$, Asp$^{28}$, Gln-Gab$^{30}$]hGH-RH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 29721 the chemical structure of which [Dat$^1$, D-Ala$^2$, Gln$^8$, Orn$^{12}$, Abu$^{15}$, Orn$^{21}$, Nle$^{27}$, Asp$^{28}$, Gln-Gab$^{30}$]hGH-RH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-0rn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 29722 the chemical structure of which [Tfa-Tyr$^a$, D-Abu$^2$, Gln$^8$, Orn$^{12}$, Abu$^{15}$, Orn$^{21}$, Nle$^{27}$, Asp$^{28}$, Gln-Gab$^{30}$]hGH-RH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Abu-OH, Tfa-Tyr-OH.

For the synthesis of Peptide 29723 the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$, Gln-Gab$^{30}$]hGH-RH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 29724 the chemical structure of which [N-Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Gln-Gab$^{30}$]hGH-RH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

HF cleavage and deprotection, and subsequent purification by semipreparative HPLC of Peptide 29701, Peptide 29703, Peptide 29704, Peptide 29706, Peptide 29708, Peptide 29710, Peptide 29720, Peptide 29721, Peptide 29722, Peptide 29723, Peptide 29724 are done as described in the case of Peptide 21300. The purified compounds are judged to be substantially (>95%) pure by analytical HPLC. Their molecular masses are checked by electrospray mass spectrometry, and the expected amino acid compositions are confirmed by amino acid analysis.

Example VI

Aqueous Solution for Intramuscular Injection

| | |
|---|---|
| N—Me-Tyr$^1$, Gln$^8$, Orn$^{12}$, Abu$^{15}$, Orn$^{21}$, Nle$^{27}$, Asp$^{28}$, Agm$^{29}$]hGH-RH(1-29) (Peptide 20356) (SEQ ID NO: 6) | 500.0 mg |
| Gelatin, nonantigenic | 5.0 mg |
| Water for injection q.s. | ad 100.0 mL |

The gelatin and GH-RH antagonist Peptide 11602 are dissolved in water for injection, and then the solution is sterile filtered.

Example VII

Long Acting Intramuscular Injectable Formulation

Sesame Oil Gel

| | |
|---|---|
| [N—Me-Tyr$^1$, Gln$^8$, Orn$^{12}$, Abu$^{15}$, Orn$^{21}$, Nle$^{27}$, Asp$^{28}$, Agm$^{29}$]hGH-RH(1-29) (Peptide 20356) (SEQ ID NO: 6) | 10.0 mg |
| Aluminum monostearate, USP | 20.0 mg |
| Sesame oil q.s. | ad 1.0 mL |

The aluminum monostearate is combined with the sesame oil and heated to 125° C. with stirring until a clear yellow solution forms. This mixture is then autoclaved for sterility and allowed to cool. The GH-RH antagonist Peptide 11604 is then added aseptically with trituration. Particularly preferred antagonists are salts of low solubility, e.g., pamoate salts and the like. These exhibit long duration of activity.

Example VIII

Long Acting Intramuscular (IM) Injectable-Biodearadable Polymer Microcapsules

Microcapsules are Made from the Following:

| | |
|---|---|
| 25/75 glycolide/lactide copolymer (0.5 intrinsic viscosity) | 99% |
| [N—Me-Tyr$^1$, Gln$^8$, Orn$^{12}$, Abu$^{15}$, Orn$^{21}$, Nle$^{27}$, Asp$^{28}$, Agm$^{29}$]hGH-RH(1-29) (Peptide 20356) (SEQ ID NO: 6) | 1% |

25 mg of the above microcapsules are suspended in 1.0 mL of the following vehicle:

| | |
|---|---|
| Dextrose | 5.0% |
| CMC, sodium | 0.5% |
| Benzyl alcohol | 0.9% |
| Tween 80 | 0.1% |
| Water, purified q.s. | ad 100% |

Example IX

Growth Hormone Releasing Activity

Growth hormone releasing is assayed by using a superfused rat pituitary cell system as described in S. Vigh and A. V. Schally, Peptides 5, Suppl: 241-347, 1984, which is incorporated by reference herein. The new synthetic peptide analogs of hGH-RH P20356 and JI-38 as control are administered for 3 minutes (1 mL perfusate) at 1 nM concentration as shown below. Fractions of 1 ml are collected and the GH content in each is determined by ELISA. Peptide P20356 was about 3 times more potent in vitro than JI-38. Effect of hGH-RH analogs (1 nM) on the GH release in superfused rat pituitary cell system

TABLE 4

GH-releasing effects of GHRH agonists P20356 (MR-356) and JI-38 in superfused rat pituitary cells
GH Response P-20356 vs JI-38
Basal GH (ng/ml) 42.51

| GH Response (ng/ml) | 1 | 2 | 3 | Average |
|---|---|---|---|---|
| P-20356 - 1 nM for 3 min | | | | |
| 1 | 49.98 | 54.99 | 52.37 | 52.45 |
| 2 | 310.58 | 325.76 | 376.11 | 337.48 |
| 3 | 491.01 | 602.1 | 576.26 | 556.46 |
| 4 | 399.95 | 270.02 | — | 334.99 |
| 5 | 200.64 | 195.18 | — | 197.91 |
| JI-38 - 1 nM for 3 min | | | | |
| 21 | 42.46 | 56.07 | — | 49.27 |
| 22 | 143.58 | 119.83 | — | 131.71 |
| 23 | 222.13 | 167.23 | — | 194.68 |
| 24 | 142.96 | 131.93 | — | 137.45 |
| 25 | 96.34 | 97.05 | — | 96.70 |

Conclusions:
P-20356 is 2-3 times more potent than JI-38

Pituitary cells from 2 male rates were used for each channel of the superfusion system. The cells were exposed to 3-min pulses of the new GHRH agonists or to JI-38 as standard every 30 min. Outflowing samples of each channel (1 ml) were collected every 3 min, and GH levels were determined by ELISA.

Example X

Receptor binding assay Ligand competition assay with $^{125}$I-labeled [His$^1$, Nle$^{27}$]hGH-RH(1-32)-NH$_2$ was used to determine the binding affinities of the novel hGH-RH agonists to membrane receptors of rat anterior pituitary cells. The methods used have been described in detail (Halmos G, et al. Receptor 3: 87-97, 1993), here by incorporated by reference. Briefly, radioidonated [His$^1$, Nle$^{27}$]hGH-RH(1-32)-NH$_2$ is prepared by the chloramines-T method. In competitive binding analyses, $^{125}$I-labeled [His$^1$, Nle$^{27}$]hGH-RH(1-32)-NH$_2$ (0.2 nM) was displaced by the GH-RH analogs at $10^{-6}$-$10^{-12}$ M. The final binding affinities were calculated using the LIGAND-PC computerized curve-fitting program. Relative affinities were compared to hGH-RH(1-29) and/or analog JI-38 (Izdebski J, et al. Proc. Natl. Acad. Sci. 92: 4872-4876, 1995) and calculated as the ratio of IC$_{50}$ of the tested peptide to the IC$_{50}$ of the standard. IC$_{50}$ is the dose of the tested peptides causing 50% inhibition of specific binding to receptors.
GHRH Receptor Binding Studies
Binding Affinities
Materials and Methods Preparation of human pituitary membrane fraction and receptor binding of GHRH agonists were performed as previously described, by using a sensitive in vitro ligand competition assay based on binding of $^{125}$I-labeled JV-1-42 to human pituitary membrane homogenates. Normal human pituitaries were purchased from the National Hormone and Peptide Program (A. F. Parlow, Los Angeles, County Harbor-UCLA Medical Center, Torrance, Calif.). Briefly, in competitive binding analysis, $^{125}$I-labeled JV-1-42 (~0.2 nM) was displaced by GHRH agonists at $10^{-6}$ to $10^{-12}$ M.

The final binding affinities were expressed as IC$_{50}$ values and were calculated by using the LIGAND PC computerized curve-fitting program of Munson and Rodbard as modified by McPherson.
Results The results of these experiments are given in the Table 5. IC$_{50}$ values of the best agonists were in the 0.01-0.09 nM range. Based on the receptor binding results all these new GHRH agonists exceeded the binding affinity of our reference peptide JI-38. Some of these new GHRH agonists tested showed the highest GHRH receptor binding affinity, their IC$_{50}$ values being 45-406 times lower than that of GHRH(1-29). Based on its IC$_{50}$ value, GHRH agonist P20356 showed 171 times higher binding affinity than our reference compound JI-38.

TABLE 5

IC$_{50}$w values and binding activities of new GHRH agonistic analogs

| | | Relative affinity (Binding potency) | |
|---|---|---|---|
| GHRH agonists | IC$_{50}$ (nM) | vs GHRH | vs JI-38 |
| GHRH (1-29) | 4.06 | 1 | |
| JI-38 | 1.71 | 2.4 | 1 |
| P20303 | 0.09 | 45.1 | 19.0 |

TABLE 5-continued

IC$_{50}$w values and binding activities of new GHRH agonistic analogs

| GHRH agonists | IC$_{50}$ (nM) | Relative affinity (Binding potency) | |
|---|---|---|---|
| | | vs GHRH | vs JI-38 |
| P20350 | 0.04 | 101.5 | 42.7 |
| P20356 | 0.01 | 406.0 | 171.0 |
| P25502 | 0.07 | 58.0 | 24.4 |
| P29702 | 0.05 | 81.2 | 34.2 |

*Expressed relative to GHRH(1-29) = 1 or JI-38 (GHRH agonist) = 1,
Values were calculated from duplicate tubes.

GH-RH Receptor Binding Studies
Binding Affinities
Materials and Methods

Preparation of human pituitary membrane fraction and receptor binding of GHRH agonists were performed as previously described, by using a sensitive in vitro ligand competition assay based on binding of $^{125}$I-labeled [His$^1$, Nle$^{27}$]hGHRH(1-32)NH$_2$ to human pituitary membrane homogenates. Normal human pituitaries were purchased from the National Hormone and Peptide Program (A. F. Parlow, Los Angeles, County Harbor—UCLA Medical Center, Torrance, Calif.).

Briefly, in competitive binding analysis, [His$^1$,$^{125}$I-Tyr$^{10}$, Nle$^{27}$]hGHRH(1-32)NH$_2$ (0.2 nM) was displaced by GHRH agonists at $10^{-6}$ to $10^{-12}$ M. The final binding affinities were expressed as IC$_{50}$ values and were calculated by using the LIGAND PC computerized curve-fitting program of Munson and Rodbard as modified by McPherson.

Results

The results of these experiments are given in the Table enclosed. IC$_{50}$ values of the best agonists were in the 0.04-0.09 nM range. Based on the receptor binding results all new GHRH agonists exceeded the binding affinity of reference peptides JI-34, JI-36 and JI-38. Some of these new GHRH agonists showed the highest GHRH receptor binding affinity, their IC$_{50}$ values being 21-48 times lower than that of the GHRH agonist JI-38.

TABLE 6

IC$_{M}$ values and binding activities of new GHRH agonistic analogs

| GHRH agonists | IC$_{50}$ (nM) | Relative affinity (Binding potency) | |
|---|---|---|---|
| | | vs GHRH | vs JI-38 |
| GH-RH(1-29) | 5.92 | 1 | |
| JI-34 | 1.37 | 4.32 | |
| JI-36 | 1.82 | 3.25 | |
| JI-38 | 1.95 | 3.03 | 1 |
| P-23252 | 0.14 | 42.3 | 13.9 |
| P-23254 | 0.07 | 84.5 | 27.8 |
| P-23256 | 0.04 | 148.0 | 48.7 |
| P-21304 | 0.08 | 74.0 | 24.4 |
| P-20352 | 0.07 | 84.5 | 27.8 |

*Expressed relative to GHRH(1-29) = 1 or JI-38 (GHRH agonist) = 1
Values were calculated from duplicate or triplicate tubes.

GH-RH Receptor Binding Studies
Binding Affinities
Materials and Methods

Preparation of human pituitary membrane fraction and receptor binding of GHRH agonists were performed as previously described, by using a sensitive in vitro ligand competition assay based on binding of $^{125}$I-labeled JV-1-42 to human pituitary membrane homogenates. Normal human pituitaries were purchased from the National Hormone and Peptide Program (A. F. Parlow, Los Angeles, County Harbor-UCLA Medical Center, Torrance, Calif.).

Briefly, in competitive binding analysis, $^{125}$I-labeled JV-1-42 (~0.2 nM) was displaced by GHRH agonists at $10^{-6}$ to $10^{-12}$ M. The final binding affinities were expressed as IC$_{50}$ values and were calculated by using the LIGAND PC computerized curve-fitting program of Munson and Rodbard as modified by McPherson Results The results of these experiments are given in the Table enclosed. IC$_{50}$ values of the best agonists were in the 0.16-0.87 nM range. Based on the receptor binding results most of the new GHRH agonists exceeded the binding affinity of reference peptides JI-38. Some of these new GHRH agonists showed 5-27 times higher binding potency than GHRH agonist JI-38. See Table 7.

TABLE 7

IC$_{50}$ values and binding activities of new GHRH agonistic analogs

| GHRH agonists | IC$_{50}$ (nM) | Relative affinity (Binding potency) vs JI-38 |
|---|---|---|
| JI-38 | 4.35 | 1 |
| P-21300 | 3.61 | 1.20 |
| P-21301 | 2.99 | 1.45 |
| P-21303 | 1.87 | 2.32 |
| P-22325 | 3.80 | 1.14 |
| P-22326 | 0.71 | 6.12 |
| P-22327 | 1.99 | 2.18 |
| P-20357 | 0.86 | 5.06 |
| P-20350 | 0.52 | 8.37 |
| P-20351 | 3.44 | 1.26 |
| P-20356 | 0.27 | 16.11 |
| P-20359 | 3.05 | 1.43 |
| P-20361 | 0.82 | 5.30 |
| P-20367 | 1.70 | 2.56 |
| P-25501 | 1.07 | 4.07 |
| P-25502 | 0.33 | 13.18 |
| P-25503 | 1.18 | 3.67 |
| P-25504 | 1.44 | 3.02 |
| P-27413 | 2.45 | 1.78 |
| P-27414 | 1.56 | 2.79 |
| P-27415 | 3.02 | 1.44 |
| P-29702 | 0.86 | 5.06 |
| P-29703 | 1.22 | 3.57 |
| P-27400 | 3.35 | 1.30 |
| P-27401 | 2.74 | 1.59 |
| P-27403 | 0.16 | 27.19 |
| P-27404 | 0.87 | 5.00 |
| P-27405 | 1.08 | 4.03 |
| P-27406 | 0.30 | 14.5 |
| P-27407 | 3.00 | 1.45 |
| P-27408 | 0.55 | 7.91 |
| P-27409 | 1.06 | 4.10 |
| P-27410 | 0.83 | 5.24 |
| P-28420 | 0.52 | 8.37 |
| P-28421 | 1.47 | 2.96 |

Expressed relative to JI-38 (GHRH agonist) = 1
Values were calculated from duplicate tubes
*reference compound Example XI In vivo tests on endocrine activity of new GHRH agonists.
Intravenous Administration.

For in vivo tests based on intravenous administration, adult male Sprague-Dawley rats are anesthetized with pentobarbital (6 mg/100/g, b.w.), injected i.p.; 20 minutes after the injection of pentobarbital, blood samples are taken from the jugular vein (pretreated level) and immediately thereafter hGH-RH(1-29)NH$_2$ (as a control) or hGH-RH analogs are injected i.v. Blood samples are taken from the jugular vein 5, 15 and 30 minutes after the injection. The blood samples are centrifuged, plasma is removed and the GH level is measured by ELISA. The results expressed as potency relative to hGH-RH(1-29)NH$_2$ appear in Table 8

TABLE 8

GH releasing potencies of hGH-RH analogs in vivo relative to JI-38 (=1) in the rat after i.v. injection

| hGH-RH Analog | After (min) | Potency |
|---|---|---|
| P-20356 | 5 | 1.07 |
|  | 15 | 0.91 |
|  | 30 | 1.22 |
| P-21300 | 5 | 0.39 |
|  | 15 | 0.51 |
|  | 30 | 0.81 |
| P-21301 | 5 | 0.79 |
|  | 15 | 0.92 |
|  | 30 | 1.00 |
| P-21303 | 5 | 0.79 |
|  | 15 | 1.14 |
|  | 30 | 0.81 |
| P-22326 | 15 | 0.28 |
|  | 30 | 0.94 |
| P-25502 | 5 | 6.76 |
|  | 15 | 5.40 |
|  | 30 | 5.83 |
| P-25504 | 5 | 1.66 |
|  | 15 | 1.65 |
|  | 30 | 1.37 |
| P-27403 | 15 | 5.01 |
|  | 30 | 4.01 |
| P-27450 | 5 | 0.07 |
|  | 15 | 0.11 |
|  | 30 | 0.49 |
| P-28475 | 5 | 0.19 |
|  | 15 | 0.36 |
|  | 30 | 0.92 |
| P-29702 | 5 | 0.98 |
|  | 15 | 0.99 |
|  | 30 | 1.22 |

Example XI

Subcutaneous Administration

Adult male rats are used and are anesthetized with pentobarbital (6 mg/100 g, b.w.), injected i.p.; 20 minutes after the injection of pentobarbital, blood samples are taken from the jugular vein (pretreated level) and immediately thereafter hGH-RH(1-29)NH$_2$ (as a control) or hGH-RH analogs are injected subcutaneously (s.c.). Blood samples are taken from the jugular vein; 5, 15 and 30 minutes or only 15 and 30 minutes after the injection. The blood samples are centrifuged, plasma is removed and the GH level is measured by ELISA. The results are summarized in terms of potency in Table 9.

TABLE 9

GH releasing potencies of hGH-RH analogs after subcutaneous (s.c.) injection relative to JI-38 (=1)

| hGH-RH analog | After (min) | Potency |
|---|---|---|
| P-20350 | 15 | 1.53 |
|  | 30 | 1.17 |
| P-20351 | 15 | 0.38 |
|  | 30 | 0.44 |

TABLE 9-continued

GH releasing potencies of hGH-RH analogs after subcutaneous (s.c.) injection relative to JI-38 (=1)

| hGH-RH analog | After (min) | Potency |
|---|---|---|
| P-20353 | 15 | 0.26 |
|  | 30 | 0.31 |
| P-20356 | 15 | 1.72 |
|  | 30 | 1.09 |
| P-20357 | 5 | 0.63 |
|  | 15 | 1.07 |
|  | 30 | 1.41 |
| P-20360 | 15 | 0.24 |
|  | 30 | 0.39 |
| P-20361 | 15 | 1.18 |
|  | 30 | 1.50 |
| P-20367 | 15 | 1.12 |
|  | 30 | 2.01 |
| P-20373 | 15 | 0.23 |
|  | 30 | 0.88 |
| P-21301 | 15 | 0.41 |
|  | 30 | 0.74 |
| P-221303 | 15 | 0.95 |
|  | 30 | 1.45 |
| P-22325 | 5 | 0.33 |
|  | 15 | 0.68 |
|  | 30 | 1.03 |
| P-22326 | 15 | 1.76 |
|  | 30 | 2.31 |
| P-22327 | 15 | 1.15 |
|  | 30 | 1.30 |
| P-25501 | 5 | 1.40 |
|  | 15 | 1.36 |
|  | 30 | 1.63 |
| P-25502 | 15 | 1.10 |
|  | 30 | 0.94 |
| P-25503 | 5 | 0.55 |
|  | 15 | 0.64 |
|  | 30 | 0.63 |
| P-25504 | 15 | 0.78 |
|  | 30 | 0.98 |
| P-27400 | 15 | 0.47 |
|  | 30 | 0.38 |
| P-27401 | 15 | 0.61 |
|  | 30 | 0.73 |
| P-27403 | 15 | 3.60 |
|  | 30 | 2.57 |
| P-27404 | 15 | 2.07 |
|  | 30 | 1.47 |
| P-27405 | 15 | 1.60 |
|  | 30 | 1.13 |
| P-27406 | 15 | 0.47 |
|  | 30 | 0.50 |
| P-27409 | 15 | 1.47 |
|  | 30 | 1.31 |
| P-27412 | 15 | 1.10 |
|  | 30 | 1.29 |
| P-27413 | 15 | 0.36 |
|  | 30 | 0.57 |
| P-27414 | 15 | 1.30 |
|  | 30 | 1.23 |
| P-27415 | 15 | 0.45 |
|  | 30 | 0.41 |
| P-27425 | 15 | 0.49 |
|  | 30 | 0.31 |
| P-29701 | 5 | 0.92 |
|  | 15 | 1.30 |
|  | 30 | 1.55 |
| P-29702 | 15 | 0.53 |
|  | 30 | 0.73 |
| P-29703 | 5 | 1.18 |
|  | 15 | 0.96 |
|  | 30 | 1.04 |

Analysis of Endocrine Tests

Following intravenous administration, the new analogs give growth hormone levels greater than those from hGH-RH(1-29)NH$_2$ or JI-38. The effect is longer lasting which indicates that the analogs have not only higher receptor affinity but also increased peptidase resistance. The most potent analogs i.v. were P-27403 and P-25502. Following subcutaneous administration, the analogs give that greater growth hormone levels than hGH-RH or JI-38. Here the analogs P-22326, P-20350, P-20356, P-27403, P-27404, P-27409, P-25501, P-25502 produce unusually high responses.

Results of i.v. and s.c. administration results show different biological activity pattern. Analogs given i.v. are subject to degradation in the blood stream. Analogs given s.c. can be degraded by peptidase at the site of injection. It is believed that activity depends primarily on binding capacity of the peptide to its receptor, and from favorable transport properties, suitable binding to plasma proteins and metabolic stability. The above findings therefore indicate that the analogs showing better activity when given subcutaneously are resistant to local degradation at the injection site and they may also be less susceptible to enzyme degradation in the blood stream and/or have more affinity for GH-RH receptors than hGH-RH(1-29)NH$_2$.

In conclusion, the most potent analogs i.v. were P-27403 and P-25502. Following subcutaneous administration, the analogs that give especially greater growth hormone levels than hGH-RH or JI-38 are P-22326, P-20350, P-20356, P-27403, P-27404, P-27409, P-25501, P-25502.

SEQUENCE LISTING

```
<160> NUMBER OF SEQ ID NOS: 42

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be Ac or Tfa
<220> FEATURE:
<221> NAME/KEY: MOD_RES
<222> LOCATION: (1)..(1)
<223> OTHER INFORMATION: Tyr, Dat, or N-Me-Tyr
<220> FEATURE:
<221> NAME/KEY: MOD_RES
<222> LOCATION: (2)..(2)
<223> OTHER INFORMATION: Ala, D-Ala, Abu, or D-Abu
<220> FEATURE:
<221> NAME/KEY: MOD_RES
<222> LOCATION: (6)..(6)
<223> OTHER INFORMATION: Phe or Fpa5
<220> FEATURE:
<221> NAME/KEY: MOD_RES
<222> LOCATION: (8)..(8)
<223> OTHER INFORMATION: Asn, Ala, Gln, Thr, or N-Me-Ala
<220> FEATURE:
<221> NAME/KEY: MOD_RES
<222> LOCATION: (11)..(11)
<223> OTHER INFORMATION: Arg, His, or Har
<220> FEATURE:
<221> NAME/KEY: MOD_RES
<222> LOCATION: (12)..(12)
<223> OTHER INFORMATION: Orn or Lys(Me)2
<220> FEATURE:
<221> NAME/KEY: MOD_RES
<222> LOCATION: (15)..(15)
<223> OTHER INFORMATION: Abu or Ala
<220> FEATURE:
<221> NAME/KEY: MOD_RES
<222> LOCATION: (20)..(20)
<223> OTHER INFORMATION: Arg, His, or Har
<220> FEATURE:
<221> NAME/KEY: MOD_RES
<222> LOCATION: (21)..(21)
<223> OTHER INFORMATION: Orn or Lys(Me)2
<220> FEATURE:
<221> NAME/KEY: MOD_RES
<222> LOCATION: (22)..(22)
<223> OTHER INFORMATION: Leu or Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (28)..(28)
<223> OTHER INFORMATION: Ser or Asp
<220> FEATURE:
<221> NAME/KEY: MOD_RES
<222> LOCATION: (29)..(29)
```

```
<223> OTHER INFORMATION: Arg, Har, Agm, D-Arg, or D-Har
<220> FEATURE:
<221> NAME/KEY: MOD_RES
<222> LOCATION: (30)..(30)
<223> OTHER INFORMATION: Arg, Agm, Ada, Amc, Aha, Apa, Har, D-Arg,
      D-Har, Gab, Gln, D-Gln, or is absent
<220> FEATURE:
<223> OTHER INFORMATION: C-term -NH2, -OH, -NHR3, -N(R3)2, or -OR3, in
      which R3 is any of C1-12 alkyl, C2-12 alkenyl, or C2-12 alkinyl
      preferably provided that if A29 is Agm then A30 and R2 are absent
      and suitably A1 is N-Me-Tyr only, and further preferably provided
      that where A30 is
<220> FEATURE:
<223> OTHER INFORMATION: cont'd from above: Agm then R2 is absent, and
      pharmaceutically acceptable salts thereof

<400> SEQUENCE: 1

Xaa Xaa Asp Ala Ile Xaa Thr Xaa Ser Tyr Xaa Xaa Val Leu Xaa Gln
1               5                   10                  15

Leu Ser Ala Xaa Xaa Xaa Leu Gln Asp Ile Xaa Xaa Xaa Xaa
            20                  25                  30

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide- P20103
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (6)..(6)
<223> OTHER INFORMATION: Fpa5
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 2

Xaa Ala Asp Ala Ile Xaa Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide-P20107
<220> FEATURE:
<221> NAME/KEY: MOD_RES
```

```
<222> LOCATION: (1)..(1)
<223> OTHER INFORMATION: N-Me-Tyr
<220> FEATURE:
<221> NAME/KEY: MOD_RES
<222> LOCATION: (6)..(6)
<223> OTHER INFORMATION: Fpa5
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 3

Xaa Ala Asp Ala Ile Xaa Thr Ala Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P20113
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (6)..(6)
<223> OTHER INFORMATION: Fpa5
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 4

Xaa Ala Asp Ala Ile Xaa Thr Asn Ser Tyr Arg Xaa Val Leu Xaa Gln
1               5                   10                  15

Leu Ser Ala Arg Xaa Leu Leu Gln Asp Ile Xaa Asp Xaa
            20                  25
```

```
<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P20115
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (6)..(6)
<223> OTHER INFORMATION: Fpa5
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 5

Xaa Ala Asp Ala Ile Xaa Thr Thr Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide -P20356
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm
```

```
<400> SEQUENCE: 6

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P20370
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 7

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P20371
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
```

<222> LOCATION: (29)..(29)
<223> OTHER INFORMATION: Agm

<400> SEQUENCE: 8

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P20372
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 9

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P20373
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)

```
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 10

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P20374
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 11

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P20375
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
```

```
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 12

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P20376
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: Agm

<400> SEQUENCE: 13

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P21301
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
```

```
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Amc
<220> FEATURE:
<223> OTHER INFORMATION: C-term NH2

<400> SEQUENCE: 14

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P22325
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Apa
<220> FEATURE:
<223> OTHER INFORMATION: C-term NH2

<400> SEQUENCE: 15

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P22327
<220> FEATURE:
<221> NAME/KEY: MOD_RES
<222> LOCATION: (1)..(1)
<223> OTHER INFORMATION: Dat
<220> FEATURE:
<221> NAME/KEY: MOD_RES
```

```
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Apa
<220> FEATURE:
<223> OTHER INFORMATION: C-term NH2

<400> SEQUENCE: 16

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P22332
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Apa
<220> FEATURE:
<223> OTHER INFORMATION: C-term NH2

<400> SEQUENCE: 17

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
```

```
      polypeptide - P22334
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Apa
<220> FEATURE:
<223> OTHER INFORMATION: C-term NH2

<400> SEQUENCE: 18

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P22335
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Apa
<220> FEATURE:
<223> OTHER INFORMATION: C-term NH2

<400> SEQUENCE: 19

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30
```

```
<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P22336
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Apa
<220> FEATURE:
<223> OTHER INFORMATION: C-term NH2

<400> SEQUENCE: 20

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P23251
<220> FEATURE:
<221> NAME/KEY: MOD_RES
<222> LOCATION: (1)..(1)
<223> OTHER INFORMATION: Dat
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Har
<220> FEATURE:
<223> OTHER INFORMATION: C-term NH2

<400> SEQUENCE: 21
```

```
Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30
```

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P23253
<220> FEATURE:
<221> NAME/KEY: MOD_RES
<222> LOCATION: (1)..(1)
<223> OTHER INFORMATION: Dat
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Har
<220> FEATURE:
<223> OTHER INFORMATION: C-term NH2

<400> SEQUENCE: 22

```
Tyr Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Leu Asp Arg Arg
            20                  25                  30
```

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P23255
<220> FEATURE:
<221> NAME/KEY: MOD_RES
<222> LOCATION: (1)..(1)
<223> OTHER INFORMATION: Dat
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:

<221> NAME/KEY: MOD_RES
<222> LOCATION: (30)..(30)
<223> OTHER INFORMATION: Har
<220> FEATURE:
<223> OTHER INFORMATION: C-term NH2

<400> SEQUENCE: 23

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P23257
<220> FEATURE:
<221> NAME/KEY: MOD_RES
<222> LOCATION: (1)..(1)
<223> OTHER INFORMATION: Dat
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Har
<220> FEATURE:
<223> OTHER INFORMATION: C-term NH2

<400> SEQUENCE: 24

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P23259
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Har
<220> FEATURE:
<223> OTHER INFORMATION: C-term NH2

<400> SEQUENCE: 25

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P23261
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Har
<220> FEATURE:
<223> OTHER INFORMATION: C-term NH2

<400> SEQUENCE: 26

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P23263
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)

<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Har
<220> FEATURE:
<223> OTHER INFORMATION: C-term NH2

<400> SEQUENCE: 27

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P23265
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Har
<220> FEATURE:
<223> OTHER INFORMATION: C-term NH2

<400> SEQUENCE: 28

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P24340

```
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Aha
<220> FEATURE:
<223> OTHER INFORMATION: C-term NH2

<400> SEQUENCE: 29

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P24342
<220> FEATURE:
<221> NAME/KEY: MOD_RES
<222> LOCATION: (1)..(1)
<223> OTHER INFORMATION: Dat
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Aha
<220> FEATURE:
<223> OTHER INFORMATION: C-term NH2

<400> SEQUENCE: 30

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30
```

-continued

```
<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P25503
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (2)..(2)
<223> OTHER INFORMATION: Abu
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Gab
<220> FEATURE:
<223> OTHER INFORMATION: C-term NH2

<400> SEQUENCE: 31

Xaa Xaa Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30

<210> SEQ ID NO 32
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P27405
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH-CH3

<400> SEQUENCE: 32
```

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Ser Arg
            20                  25

<210> SEQ ID NO 33
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P27406
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH-CH3

<400> SEQUENCE: 33

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg
            20                  25

<210> SEQ ID NO 34
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P27407
<220> FEATURE:
<221> NAME/KEY: MOD_RES
<222> LOCATION: (1)..(1)
<223> OTHER INFORMATION: Dat
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH-CH3

<400> SEQUENCE: 34

Xaa Ala Asp Ala Ile Phe Thr Gln Ser Tyr Arg Xaa Val Leu Xaa Gln

```
                1               5                  10                  15
Leu Ser Ala Arg Xaa Leu Leu Gln Asp Ile Xaa Asp Arg
                20                  25

<210> SEQ ID NO 35
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P27413
<220> FEATURE:
<221> NAME/KEY: MOD_RES
<222> LOCATION: (1)..(1)
<223> OTHER INFORMATION: Dat
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH-CH3

<400> SEQUENCE: 35

Xaa Ala Asp Ala Ile Phe Thr Gln Ser Tyr His Xaa Val Leu Xaa Gln
1               5                   10                  15
Leu Ser Ala His Xaa Leu Leu Gln Asp Ile Xaa Asp Arg
                20                  25

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide - P27415
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (30)..(30)
<223> OTHER INFORMATION: Gab
<220> FEATURE:
<223> OTHER INFORMATION: C-term NH-CH3
```

-continued

```
<400> SEQUENCE: 36

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30

<210> SEQ ID NO 37
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P27419
<220> FEATURE:
<223> OTHER INFORMATION: N-term Ac
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH-CH3

<400> SEQUENCE: 37

Tyr Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Ser Arg
            20                  25

<210> SEQ ID NO 38
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide - P27424
<220> FEATURE:
<221> NAME/KEY: MOD_RES
<222> LOCATION: (1)..(1)
<223> OTHER INFORMATION: Dat
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH-CH3

<400> SEQUENCE: 38

Xaa Ala Asp Ala Ile Phe Thr Thr Ser Tyr Arg Xaa Val Leu Xaa Gln
```

```
                1               5                  10                  15
Leu Ser Ala Arg Xaa Leu Leu Gln Asp Ile Xaa Ser Arg
                20                  25
```

<210> SEQ ID NO 39
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide - P29703
<220> FEATURE:
<221> NAME/KEY: MOD_RES
<222> LOCATION: (1)..(1)
<223> OTHER INFORMATION: N-Me-Tyr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (31)..(31)
<223> OTHER INFORMATION: Gab
<220> FEATURE:
<223> OTHER INFORMATION: C-term NH2

<400> SEQUENCE: 39

```
Xaa Ala Asp Ala Ile Phe Thr Gln Ser Tyr Arg Xaa Val Leu Xaa Gln
1               5                  10                  15
Leu Ser Ala Arg Xaa Leu Leu Gln Asp Ile Xaa Ser Arg Gln Xaa
                20                  25                  30
```

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be Ac or Tfa
<220> FEATURE:
<221> NAME/KEY: MOD_RES
<222> LOCATION: (1)..(1)
<223> OTHER INFORMATION: Tyr, Dat, or N-Me-Tyr
<220> FEATURE:
<221> NAME/KEY: MOD_RES
<222> LOCATION: (2)..(2)
<223> OTHER INFORMATION: Ala, D-Ala, Abu, or D-Abu
<220> FEATURE:
<221> NAME/KEY: MOD_RES
<222> LOCATION: (6)..(6)
<223> OTHER INFORMATION: Phe or Fpa5
<220> FEATURE:
<221> NAME/KEY: MOD_RES
<222> LOCATION: (8)..(8)
<223> OTHER INFORMATION: Asn, Ala, Gln, Thr, or N-Me-Ala
<220> FEATURE:
<221> NAME/KEY: MOD_RES
<222> LOCATION: (11)..(11)
<223> OTHER INFORMATION: Arg, His, or Har
<220> FEATURE:

```
<221> NAME/KEY: MOD_RES
<222> LOCATION: (12)..(12)
<223> OTHER INFORMATION: Orn or Lys(Me)2
<220> FEATURE:
<221> NAME/KEY: MOD_RES
<222> LOCATION: (15)..(15)
<223> OTHER INFORMATION: His, Abu, Aib, Aah, Aap, Ala, or D-Ala
<220> FEATURE:
<221> NAME/KEY: MOD_RES
<222> LOCATION: (20)..(20)
<223> OTHER INFORMATION: Arg, His, or Har
<220> FEATURE:
<221> NAME/KEY: MOD_RES
<222> LOCATION: (21)..(21)
<223> OTHER INFORMATION: Orn or Lys(Me)2
<220> FEATURE:
<221> NAME/KEY: MOD_RES
<222> LOCATION: (22)..(22)
<223> OTHER INFORMATION: Leu or Orn
<220> FEATURE:
<221> NAME/KEY: MOD_RES
<222> LOCATION: (27)..(27)
<223> OTHER INFORMATION: Nle or Met
<220> FEATURE:
<221> NAME/KEY: MOD_RES
<222> LOCATION: (28)..(28)
<223> OTHER INFORMATION: Ser or Asp
<220> FEATURE:
<221> NAME/KEY: MOD_RES
<222> LOCATION: (29)..(29)
<223> OTHER INFORMATION: Arg, Har, Agm, D-Arg, or D-Har
<220> FEATURE:
<221> NAME/KEY: MOD_RES
<222> LOCATION: (30)..(30)
<223> OTHER INFORMATION: Arg, Agm, Ada, Amc, Aha, Apa, Har, D-Arg,
      D-Har, Gab, Gln, D-Gln, Gln-Gab, D-Gln-Gab, or is absent
<220> FEATURE:
<223> OTHER INFORMATION: C-term NH2, -OH, -NHR3, -N(R3)2, or -OR3, in
      which R3 is any of C1-12 alkyl, C2-12 alkenyl, or C2-12 alkinyl,
      provided that if A29 is Agm then A30 and R2 are absent, A1 is
      N-Me-Tyr only, and pharmaceutically acceptable salts thereof

<400> SEQUENCE: 40

Xaa Xaa Asp Ala Ile Xaa Thr Xaa Ser Tyr Xaa Xaa Val Leu Xaa Gln
1               5                   10                  15

Leu Ser Ala Xaa Xaa Xaa Leu Gln Asp Ile Leu Xaa Xaa Xaa
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: May be N-term Ac
<220> FEATURE:
<221> NAME/KEY: MOD_RES
<222> LOCATION: (1)..(1)
<223> OTHER INFORMATION: Tyr, Dat, or N-Me-Tyr
<220> FEATURE:
<221> NAME/KEY: MOD_RES
<222> LOCATION: (2)..(2)
<223> OTHER INFORMATION: Ala, D-Ala, Abu, or D-Abu
<220> FEATURE:
<221> NAME/KEY: MOD_RES
<222> LOCATION: (6)..(6)
<223> OTHER INFORMATION: Phe or Fpa5
<220> FEATURE:
<221> NAME/KEY: MOD_RES
<222> LOCATION: (8)..(8)
<223> OTHER INFORMATION: Asn, Ala, Gln, or Thr
<220> FEATURE:
<221> NAME/KEY: MOD_RES
<222> LOCATION: (12)..(12)
```

```
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (28)..(28)
<223> OTHER INFORMATION: Ser or Asp
<220> FEATURE:
<221> NAME/KEY: MOD_RES
<222> LOCATION: (29)..(29)
<223> OTHER INFORMATION: Arg, D-Arg, or Agm
<220> FEATURE:
<221> NAME/KEY: MOD_RES
<222> LOCATION: (30)..(30)
<223> OTHER INFORMATION: Arg, Agm, Ada, Amc, Aha, Apa, Har, D-Arg,
      D-Har, Gab, Gln, D-Gln, or is absent
<220> FEATURE:
<223> OTHER INFORMATION: C-term -NH2, -OH, -NHR3, -N(R3)2, or -OR3, in
      which R3 is any of C1-12 alkyl, C2-12 alkenyl, or C2-12 alkinyl,
      provided that if A29 is Agm then A30 and R2 are absent, A1 is
      N-Me-Tyr only, and pharmaceutically acceptable salts thereof

<400> SEQUENCE: 41

Xaa Xaa Asp Ala Ile Xaa Thr Xaa Ser Tyr Arg Xaa Val Leu Xaa Gln
1               5                   10                  15

Leu Ser Ala Arg Xaa Leu Leu Gln Asp Ile Xaa Xaa Xaa Xaa
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Dat or N-Me-Tyr
<220> FEATURE:
<221> NAME/KEY: MOD_RES
<222> LOCATION: (2)..(2)
<223> OTHER INFORMATION: Ala or D-Ala
<220> FEATURE:
<221> NAME/KEY: MOD_RES
<222> LOCATION: (6)..(6)
<223> OTHER INFORMATION: Phe or Fpa5
<220> FEATURE:
<221> NAME/KEY: MOD_RES
<222> LOCATION: (8)..(8)
<223> OTHER INFORMATION: Asn, Gln, or Thr
<220> FEATURE:
<221> NAME/KEY: MOD_RES
<222> LOCATION: (12)..(12)
<223> OTHER INFORMATION: Orn
<220> FEATURE:
<221> NAME/KEY: MOD_RES
<222> LOCATION: (15)..(15)
<223> OTHER INFORMATION: Abu
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (27)..(27)
```

```
<223> OTHER INFORMATION: Nle
<220> FEATURE:
<221> NAME/KEY: MOD_RES
<222> LOCATION: (28)..(28)
<223> OTHER INFORMATION: Ser or Asp
<220> FEATURE:
<221> NAME/KEY: MOD_RES
<222> LOCATION: (29)..(29)
<223> OTHER INFORMATION: Arg, D-Arg, or Agm
<220> FEATURE:
<221> NAME/KEY: MOD_RES
<222> LOCATION: (30)..(30)
<223> OTHER INFORMATION: Arg, Agm, Ada, Amc, Aha, Apa, Har, D-Arg,
      D-Har, Gab, Gln, D-Gln, or is absent
<220> FEATURE:
<223> OTHER INFORMATION: C-term -NH2, -OH, -NHR3, -N(R3)2, or -OR3,
      in which R3 is any of C1-12 alkyl, C2-12 alkenyl, or C2-12
      alkinyl, provided that if A29 is Agm then A30 and R2 are absent,
      A1 is N-Me-Tyr only, and pharmaceutically acceptable salts thereof

<400> SEQUENCE: 42

Xaa Xaa Asp Ala Ile Xaa Thr Xaa Ser Tyr Arg Xaa Val Leu Xaa Gln
1               5                   10                  15

Leu Ser Ala Arg Xaa Leu Leu Gln Asp Ile Xaa Xaa Xaa Xaa
            20                  25                  30
```

We claim:

1. A peptide selected from the group having the formulae:

$$[R_1\text{-}A^1,A^2,A^6,A^8,A^{11},A^{12},A^{15},A^{20},A^{21},A^{22},Nle^{27},A^{28},A^{29},A^{30}]hGH\text{-}RH(1\text{-}30)\text{-}R_2$$

wherein
$R_1$ is Ac, Tfa, or is absent,
$A^1$ is Tyr, Dat, or N-Me-Tyr,
$A^2$ is D-Ala, or D-Abu,
$A^6$ is Phe, or Fpa5,
$A^8$ is Asn, Ala, Gln, Thr, or N-Me-Ala,
$A^{11}$ is Arg, His, or Har,
$A^{12}$ is Orn, or Lys(Me)$_2$,
$A^{15}$ is His, Abu, Aib, Aah, Aap, Ala, or D-Ala,
$A^{20}$ is Arg, His, or Har,
$A^{21}$ is Orn, or Lys(Me)$_2$,
$A^{22}$ is Leu, or Orn,
$A^{28}$ is Ser, or Asp,
$A^{29}$ is Arg, Har, Agm, D-Arg, or D-Har,
$A^{30}$ is Arg, Agm, Ada, Amc, Aha, Apa, Har, D-Arg, D-Har, Gab, Gln, D-Gln, Gln-Gab, D-Gln-Gab, or is absent,
$R_2$ is —NHR$_3$, in which R$_3$ is any of C$_{1-2}$ alkyl, and pharmaceutically acceptable salts thereof.

2. The peptide of claim 1 selected from the group having the formulae:

$$[R_1\text{-}A^1,A^2,A^6,A^8,A^{11},Orn^{12},Abu^{15},A^{20},Orn^{21},A^{22},Nle^{27},A^{28},A^{29},A^{30}]hGH\text{-}RH(1\text{-}30)\text{-}R_2$$

wherein
$R_1$ is Ac, or is absent,
$A^8$ is Asn, Ala, Gln, or Thr,
$A^{11}$ is Arg,
$A^{20}$ is Arg,
$A^{22}$ is Leu,
$A^{29}$ is Arg, D-Arg, or Agm,
$A^{30}$ is Arg, Agm, Ada, Amc, Aha, Apa, Har, D-Arg, D-Har, Gab, Gln, D-Gln, or is absent,
and pharmaceutically acceptable salts thereof.

3. The peptide of claim 2 selected from the group having the formulae:

$$[A^1,A^2,A^6,A^8,A^{11},Orn^{12},Abu^{15},A^{20},Orn^{21},A^{22},Nle^{27},A^{28},A^{29},A^{30}]hGH\text{-}RH(1\text{-}30)\text{-}R_2$$

wherein
$A^1$ is Dat, or N-Me-Tyr,
$A^2$ is D-Ala,
$A^8$ is Asn, Gln, or Thr,
$A^{11}$ is Arg,
$A^{20}$ is Arg,
$A^{22}$ is Leu,
$A^{29}$ is Arg, D-Arg, or Agm,
$A^{30}$ is Arg, Agm, Ada, Amc, Aha, Apa, Har, D-Arg, D-Har, Gab, Gln, D-Gln, or is absent,
and pharmaceutically acceptable salts thereof.

4. The peptide of claim 1 selected from the group having the formulae:

```
P-26803  [N-Me-Tyr¹, D-Ala², Gln⁸, His¹¹, Orn¹², Abu¹⁵, His²⁰, Orn²¹, Nle²⁷,
          Ada³⁰]hGH-RH(1-30)NH-CH₃

P-27400  [Dat¹, D-Ala², Orn¹², Abu¹⁵, Orn²¹, Nle²⁷, Asp²⁸]hGH-RH(1-29)NH-CH₃

P-27401  [Dat¹, D-Ala², Gln⁸, Orn¹², Abu¹⁵, Orn²¹, Nle²⁷, Asp²⁸, D-Arg²⁹]hGH-
          RH(1-29)NH-CH₃

P-27403  [N-Me-Tyr¹, D-Ala², Gln⁸, Orn¹², Abu¹⁵, Orn²¹, Nle²⁷, Asp²⁸]hGH-RH(1-
          29)NH-CH₃

P-27404  [N-Me-Tyr¹, D-Ala², Fpa5⁶, Orn¹², Abu¹⁵, Orn²¹, Nle²⁷, Asp²⁸]hGH-RH(1-
          29)NH-CH₃
```

-continued

P-27408 [Dat$^1$, D-Ala$^2$, Gln$^8$, Orn$^{12}$, Abu$^{15}$, Orn$^{21}$, Nle$^{27}$, Asp$^{28}$]hGH-RH(1-30)NH-CH$_3$

P-27409 [N-Me-Tyr$^1$, D-Ala$^2$, Orn$^{12}$, Abu$^{15}$, Orn$^{21}$, Nle$^{27}$, Asp$^{28}$]hGH-RH(1-29)NH-CH$_3$

P-27410 [N-Me-Tyr$^1$, D-Ala$^2$, Thr$^8$, Orn$^{12}$, Abu$^{15}$, Orn$^{21}$, Nle$^{27}$, Asp$^{28}$]hGH-RH(1-29)NH-CH$_3$

P-27411 [N-Me-Tyr$^1$, D-Ala$^2$, Thr$^8$, Orn$^{12}$, Abu$^{15}$, Orn$^{21}$, Nle$^{27}$]hGH-RH(1-29)NH-CH$_3$

P-27412 [N-Me-Tyr$^1$, D-Ala$^2$, Ala$^8$, Orn$^{12}$, Abu$^{15}$, Orn$^{21}$, Nle$^{27}$, Asp$^{28}$]hGH-RH(1-29)NH-CH$_3$

P-27414 [N-Me-Tyr$^1$, D-Ala$^2$, Fpa5$^6$, Orn$^{12}$, Abu$^{15}$, Orn$^{21}$, Nle$^{27}$, Gab$^{30}$]hGH-RH(1-30)NH-CH$_3$

P-27416 [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGH-RH(1-29)NH-CH$_3$

P-27417 [Ac-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH-CH$_3$

P-27418 [Ac-Tyr$^1$, D-Ala$^2$, Fpa5$^6$, Abu$^{15}$, Orn$^{21}$, Nle$^{27}$, Asp$^{28}$]hGH-RH(1-29)NH-CH$_3$

P-27441 [N-Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGH-RH(1-29)NH-CH$_3$

P-27442 [N-Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGH-RH(1-29)NH-CH$_3$

P-27444 [N-Me-Tyr$^1$, D-Ala$^2$, Orn$^{12}$, Abu$^{15}$, Orn$^{21}$, Nle$^{27}$, Asp$^{28}$, D-Arg$^{29}$]hGH-RH(1-29)NH-CH$_3$

P-27445 [N-Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGH-RH(1-29)NH-CH$_3$

P-27446 [N-Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGH-RH(1-29)NH-CH$_3$

P-27447 [N-Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGH-RH(1-30)NH-CH$_3$

P-27448 [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGH-RH(1-30)NH-CH$_3$

P-27449 [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGH-RH(1-30)NH-CH$_3$

P-27450 [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGH-RH(1-30)NH-CH$_3$

P-27451 [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGH-RH(1-30)NH-CH$_3$

P-28420 [N-Me-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH-CH$_2$-CH$_3$

P-28421 [N-Me-Tyr$^1$, D-Ala$^2$, Orn$^{12}$, Abu$^{15}$, Orn$^{21}$, Nle$^{27}$, Asp$^{28}$]hGH-RH(1-29)NH-CH$_2$-CH$_3$

P-28430 [N-Me-Tyr$^1$, D-Ala$^2$, Gln$^8$, Orn$^{12}$, Abu$^{15}$, Orn$^{21}$, Nle$^{27}$]hGH-RH(1-29)NH-CH$_2$-CH$_3$

P-28431 [N-Me-Tyr$^1$, D-Ala$^2$, Thr$^8$, Orn$^{12}$, Abu$^{15}$, Orn$^{21}$, Nle$^{27}$, Asp$^{28}$]hGH-RH(1-29)NH-CH$_2$-CH$_3$

P-28460 [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGH-RH(1-29)NH-CH$_2$-CH$_3$

P-28461 [N-Me-Tyr$^1$, D-Ala$^2$, Gln$^8$, Orn$^{12}$, Abu$^{15}$, Orn$^{21}$, Nle$^{27}$]hGH-RH(1-29)NH-CH$_2$-CH$_3$

P-28462 [N-Me-Tyr$^1$, D-Ala$^2$, Fpa5$^6$, Orn$^{12}$, Abu$^{15}$, Orn$^{21}$, Nle$^{27}$]hGH-RH(1-29)NH-CH$_2$-CH$_3$

P-28463 [N-Me-Tyr$^1$, D-Ala$^2$, Orn$^{12}$, Abu$^{15}$, Orn$^{21}$, Nle$^{27}$]hGH-RH(1-29)NH-CH$_2$-CH$_3$

P-28464 [N-Me-Tyr$^1$, D-Ala$^2$, Fpa5$^6$, Gln$^8$, Orn$^{12}$, Abu$^{15}$, Orn$^{21}$, Nle$^{27}$]hGH-RH(1-29)NH-CH$_2$-CH$_3$

P-28465 [N-Me-Tyr$^1$, D-Ala$^2$, Gln$^8$, Orn$^{12}$, Abu$^{15}$, Orn$^{21}$, Nle$^{27}$, Asp$^{28}$]hGH-RH(1-29)NH-CH$_2$-CH$_3$

P-28466 [N-Me-Tyr$^1$, D-Ala$^2$, Fpa5$^6$, Orn$^{12}$, Abu$^{15}$, Orn$^{21}$, Nle$^{27}$, Asp$^{28}$]hGH-RH(1-29)NH-CH$_2$-CH$_3$

-continued

P-28467 [N-Me-Tyr¹, D-Ala², Orn¹², Abu¹⁵, Orn²¹, Nle²⁷, Asp²⁸]hGH-RH(1-29)NH-CH₂-CH₃

P-28468 [N-Me-Tyr¹, D-Ala², Fpa5⁶, Gln⁸, Orn¹², Abu¹⁵, Orn²¹, Nle²⁷, Asp²⁸]hGH-RH(1-29)NH-CH₂-CH₃

P-28469 [Dat¹, D-Ala², Gln⁸, Orn¹², Abu¹⁵, Orn²¹, Nle²⁷]hGH-RH(1-29)NH-CH₂-CH₃

P-28470 [Dat¹, D-Ala², Orn¹², Abu¹⁵, Orn²¹, Nle²⁷]hGH-RH(1-29)NH-CH₂-CH₃

P-28471 [Dat¹, D-Ala², Gln⁸, Orn¹², Abu¹⁵, Orn²¹, Nle²⁷, Asp²⁸]hGH-RH(1-29)NH-CH₂-CH₃

P-28472 [Dat¹, D-Ala², Fpa5⁶, Gln⁸, Orn¹², Abu¹⁵, Orn²¹, Nle²⁷, Asp²⁸]hGH-RH(1-29)NH-CH₂-CH₃

P-28473 [Dat¹, D-Ala², Fpa5⁶, Orn¹², Abu¹⁵, Orn²¹, Nle²⁷, Asp²⁸]hGH-RH(1-29)NH-CH₂-CH₃

P-28474 [Dat¹, D-Ala², Orn¹², Abu¹⁵, Orn²¹, Nle²⁷, Asp²⁸]hGH-RH(1-29)NH-CH₂-CH₃

P-28475 [N-Me-Tyr¹, D-Ala², Gln⁸, Orn¹², Abu¹⁵, Orn²¹, Nle²⁷, Asp²⁸, Apa³⁰]hGH-RH(1-30)NH-CH₂-CH₃

P-28476 [N-Me-Tyr¹, D-Ala², Gln⁸, Orn¹², Abu¹⁵, Orn²¹, Nle²⁷, Asp²⁸, Aha³⁰]hGH-RH(1-30)NH-CH₂-CH₃

P-28477 [N-Me-Tyr¹, D-Ala², Gln⁸, Orn¹², Abu¹⁵, Orn²¹, Nle²⁷, Asp²⁸, Amc³⁰]hGH-RH(1-30)NH-CH₂-CH₃

P-28478 [N-Me-Tyr¹, D-Ala², Gln⁸, Orn¹², Abu¹⁵, Orn²¹, Nle²⁷, Asp²⁸, Har³⁰]hGH-RH(1-30)NH-CH₂-CH₃; and P-28479 [N-Me-Tyr¹, D-Ala², Gln⁸, His¹¹, Orn¹², Abu¹⁵, His²⁰, Orn²¹, Nle²⁷, Asp²⁸, Apa³⁰]hGH-RH(1-30)NH-CH₂-CH₃.

5. A GH-RH peptide selected from the group having the formula:

(SEQ ID NO: 35)
P-27413 [Dat¹, Gln⁸, His¹¹, Orn¹², Abu¹⁵, His²⁰, Orn²¹, Nle²⁷, Asp²⁸]hGH-RH(1-29)NH-CH₃;

(SEQ ID NO: 36)
P-27415 [N-Me-Tyr¹, Orn¹², Abu¹⁵, Orn²¹, Nle²⁷, Gab³⁰]hGH-RH(1-30)NH-CH₃;

P-27440 [Dat¹, Gln⁸, Orn¹², Abu¹⁵, Orn²¹, Nle²⁷, Asp²⁸, D-Arg²⁹]hGH-RH(1-29)NH-CH₃;

P-27443 [N-Me-Tyr¹, Orn¹², Abu¹⁵, Orn²¹, Nle²⁷, D-Arg²⁹]hGH-RH(1-29)NH-CH₃;

(SEQ ID NO: 32)
P-27405 [N-Me-Tyr¹, Gln⁸, Orn¹², Abu¹⁵, Orn²¹, Nle²⁷]hGH-RH(1-29)NH-CH₃;

(SEQ ID NO: 33)
P-27406 [N-Me-Tyr¹, Gln⁸, Orn¹², Abu¹⁵, Orn²¹, Nle²⁷, Asp²⁸]hGH-RH(1-29)NH-CH₃;

(SEQ ID NO: 34)
P-27407 [Dat¹, Gln⁸, Orn¹², Abu¹⁵, Orn²¹, Nle²⁷, Asp²⁸]hGH-RH(1-29)NH-CH₃;

P-27422 [N-Me-D-Tyr¹, Gln⁸, Orn¹², Abu¹⁵, Orn²¹, Nle²⁷, Asp²⁸]hGH-RH(1-29)NH-CH₃;

P-27423 [N-Me-D-Tyr¹, D-Ala², Orn¹², Abu¹⁵, Orn²¹, Nle²⁷, Asp²⁸]hGH-RH(1-29)NH-CH₃;

P-27425 [N-Me-D-Tyr¹, D-Ala², Gln⁸, Orn¹², Abu¹⁵, Orn²¹, Nle²⁷, Asp²⁸]hGH-RH(1-29)NH-CH₃;

(SEQ ID NO: 37)
P-27419 [Ac-Tyr¹, Thr⁸, Orn¹², Abu¹⁵, Orn²¹, Nle²⁷]hGH-RH(1-29)NH-CH₃; and (SEQ ID NO: 38)
P-27424 [Dat¹, Thr⁸, Orn¹², Abu¹⁵, Orn²¹, Nle²⁷]hGH-RH(1-29)NH-CH₃.

6. The peptide of claim 1 having the formula:

P-27403 [N-Me-Tyr¹, D-Ala², Gln⁸, Orn¹², Abu¹⁵, Orn²¹, Nle²⁷, Asp²⁸]hGH-RH(1-29)NH-CH₃.

7. The peptide of claim 1 having the formula:

P-27409 [N-Me-Tyr¹, D-Ala², Abu¹⁵, Orn²¹, Nle²⁷, Asp²⁸]hGH-RH(1-29)NH-CH₃.

8. The peptide of claim 1 having the formula:

P-27410 [N-Me-Tyr¹, D-Ala², Thr⁸, Orn¹², Abu¹⁵, Orn²¹, Nle²⁷, Asp²⁸]hGH-RH(1-29)NH-CH₃.

9. The peptide of claim 5 having the formula:

(SEQ ID NO: 33)
P-27406 [N-Me-Tyr¹, Gln⁸, Orn¹², Abu¹⁵, Orn²¹, Nle²⁷, Asp²⁸]hGH-RH(1-29)NH-CH₃.

10. A pharmaceutical composition comprising a therapeutically effective amount of GH-RH peptide having the formula:

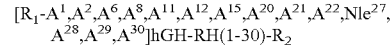

wherein
R₁ is Ac, Tfa, or is absent,
A¹ is Tyr, Dat, or N-Me-Tyr,
A² is D-Ala or D-Abu,
A⁶ is Phe, or Fpa5,
A⁸ is Asn, Ala, Gln, Thr, or N-Me-Ala,
A¹¹ is Arg, His, or Har,
A¹² is Orn, or Lys(Me)₂,
A¹⁵ is His, Abu, Aib, Aah, Aap, Ala, or D-Ala,
A²⁰ is Arg, His, or Har,
A²¹ is Orn, or Lys(Me)₂, A$^{22}$ is Leu, or Orn, A$^{28}$ is Ser, or Asp, A$^{29}$ is Arg, Har, Agm, D-Arg, or D-Har, A$^{30}$ is Arg, Agm, Ada, Amc, Aha, Apa, Har, D-Arg, D-Har, Gab, Gln, D-Gln, Gln-Gab, D-Gln-Gab, or is absent, R$_2$ is —NHR$_3$, in which R$_3$ is any of C$_{1-2}$ alkyl, and pharmaceutically acceptable salts thereof, and a pharmaceutically acceptable excipient.

11. A pharmaceutical composition comprising a therapeutically effective amount of GH-RH peptide selected from the group having the formula:

```
                                        (SEQ ID NO: 35)
P-27413   [Dat¹, Gln⁸, His¹¹, Orn¹², Abu¹⁵, His²⁰,
          Orn²¹, Nle²⁷, Asp²⁸]hGH-RH(1-29)NH-CH₃;

(SEQ ID NO: 36)
P-27415   [N-Me-Tyr¹, Orn¹², Abu¹⁵, Orn²¹, Nle²⁷,
          Gab³⁰]hGH-RH(1-30)NH-CH₃;

P-27440   [Dat¹, Gln⁸, Orn¹², Abu¹⁵, Orn²¹, Nle²⁷,
          Asp²⁸, D-Arg²⁹]hGH-RH(1-29)NH-CH₃;

P-27443   [N-Me-Tyr¹, Orn¹², Abu¹⁵, Orn²¹, Nle²⁷,
          D-Arg²⁹]hGH-RH(1-29)NH-CH₃;

(SEQ ID NO: 32)
P-27405   [N-Me-Tyr¹, Gln⁸, Orn¹², Abu¹⁵, Orn²¹,
          Nle²⁷]hGH-RH(1-29)NH-CH₃;

(SEQ ID NO: 33)
P-27406   [N-Me-Tyr¹, Gln⁸, Orn¹², Abu¹⁵, Orn²¹, Nle²⁷,
          Asp²⁸]hGH-RH(1-29)NH-CH₃;

(SEQ ID NO: 34)
P-27407   [Dat¹, Gln⁸, Orn¹², Abu¹⁵, Orn²¹, Nle²⁷,
          Asp²⁸]hGH-RH(1-29)NH-CH₃;

(SEQ ID NO: 37)
P-27419   [Ac-Tyr¹, Thr⁸, Orn¹², Abu¹⁵, Orn²¹,
          Nle²⁷]hGH-RH(1-29)NH-CH₃; and (SEQ ID NO: 38)
P-27424   [Dat¹, Thr⁸, Orn¹², Abu¹⁵, Orn²¹,
          Nle²⁷]hGH-RH(1-29)NH-CH₃,
``` and a pharmaceutically acceptable excipient.

12. The pharmaceutical composition of claim 10 comprising a therapeutically effective amount of GH-RH peptide having the formula:

```
P-27403   [N-Me-Tyr¹, D-Ala², Gln⁸, Orn¹², Abu¹⁵,
          Orn²¹, Nle²⁷, Asp²⁸]hGH-RH(1-29)NH-CH₃,
``` and a pharmaceutically acceptable excipient.

13. The pharmaceutical composition of claim 10 comprising a therapeutically effective amount of GH-RH peptide having the formula:

```
P-27409   [N-Me-Tyr¹, D-Ala², Orn¹², Abu¹⁵, Orn²¹,
          Nle²⁷, Asp²⁸]hGH-RH(1-29)NH-CH₃,
``` and a pharmaceutically acceptable excipient.

14. The pharmaceutical composition of claim 10 comprising a therapeutically effective amount of GH-RH peptide having the formula:

```
P-27410   [N-Me-Tyr¹, D-Ala², Thr⁸, Orn¹², Abu¹⁵,
          Orn²¹, Nle²⁷, Asp²⁸]hGH-RH(1-29)NH-CH₃,
``` and a pharmaceutically acceptable excipient.

15. The pharmaceutical composition of claim 11 comprising a therapeutically effective amount of GH-RH peptide having the formula:

```
                                        (SEQ ID NO: 33)
P-27406   [N-Me-Tyr¹, Gln⁸, Orn¹², Abu¹⁵, Orn²¹,
          Nle²⁷, Asp²⁸]hGH-RH(1-29)NH-CH₃,
``` and a pharmaceutically acceptable excipient.

* * * * *